US012595481B2

(12) United States Patent
Leventhal et al.

(10) Patent No.: US 12,595,481 B2
(45) Date of Patent: Apr. 7, 2026

(54) METHODS AND COMPOSITIONS FOR NEUROPROTECTION

(71) Applicant: DISARM THERAPEUTICS, INC., Cambridge, MA (US)

(72) Inventors: Liza Leventhal, Lexington, MA (US); Thomas Engber, Cambridge, MA (US); Raul Eduardo Krauss, Chestnut Hill, MA (US); Rajesh Devraj, Chesterfield, MO (US); Robert Owen Hughes, Newtown, CT (US); Todd Bosanac, New Milford, CT (US); Sudhir Agrawal, Shrewsbury, MA (US); Marco A. Passini, Northborough, MA (US)

(73) Assignee: DISARM THERAPEUTICS, INC., Cambridge, MA (US)

( * ) Notice: Subject to any disclaimer, the term of this patent is extended or adjusted under 35 U.S.C. 154(b) by 978 days.

(21) Appl. No.: 17/778,567

(22) PCT Filed: Nov. 25, 2020

(86) PCT No.: PCT/US2020/062289
§ 371 (c)(1),
(2) Date: May 20, 2022

(87) PCT Pub. No.: WO2021/108602
PCT Pub. Date: Jun. 3, 2021

(65) Prior Publication Data
US 2023/0242909 A1 Aug. 3, 2023

Related U.S. Application Data

(60) Provisional application No. 62/940,437, filed on Nov. 26, 2019.

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/11* (2013.01); *C12N 2310/3125* (2013.01); *C12N 2310/314* (2013.01); *C12N 2310/315* (2013.01); *C12N 2310/316* (2013.01); *C12N 2310/531* (2013.01)

(58) Field of Classification Search
CPC .............. C12N 15/113; C12N 2310/11; C12N 2310/3125; C12N 2310/314; C12N 2310/315; C12N 2310/316; C12N 2310/531; C12N 2310/322; C12N 2310/341; C12N 2310/345; C12N 2310/3525; A61K 31/7088
See application file for complete search history.

(56) References Cited

U.S. PATENT DOCUMENTS

| | | | |
|---|---|---|---|
| 2004/0096830 A1 | 5/2004 | Dobie | |
| 2005/0244851 A1* | 11/2005 | Blume | C12Q 1/6876 |
| | | | 435/287.2 |
| 2006/0003322 A1* | 1/2006 | Bentwich | G16B 15/10 |
| | | | 435/6.16 |
| 2007/0050146 A1* | 3/2007 | Bentwich | C12Q 1/6809 |
| | | | 435/6.1 |
| 2007/0243546 A1* | 10/2007 | Cao | C12Q 1/6837 |
| | | | 435/6.12 |
| 2014/0079712 A1 | 3/2014 | Freeman et al. | |

FOREIGN PATENT DOCUMENTS

| | | |
|---|---|---|
| WO | 2012/178022 A2 | 12/2012 |
| WO | 2016/183041 A2 | 11/2016 |
| WO | 2017/164230 A1 | 9/2017 |
| WO | 2018/007980 A1 | 1/2018 |
| WO | 2018/057989 A1 | 3/2018 |
| WO | 2018/154413 A1 | 8/2018 |
| WO | 2019/079572 A1 | 4/2019 |
| WO | 2019079572 * | 4/2019 |
| WO | 2019/236879 A1 | 12/2019 |
| WO | 2019/236884 A1 | 12/2019 |
| WO | 2019/236890 A1 | 12/2019 |

OTHER PUBLICATIONS

Czech VL, O'Connor LC, Philippon B, Norman E, Byrne AB. TIR-1/SARM1 inhibits axon regeneration and promotes axon degeneration. Elife. Apr. 21, 2023.*
Sczakiel, Georg. "Theoretical and experimental approaches to design effective antisense oligonucleotides." Front. Biosci 5 (2000)).*
Watts, Jonathan K., and David R. Corey. "Gene silencing by siRNAs and antisense oligonucleotides in the laboratory and the clinic." The Journal of pathology 226.2 (2011)).*
International Search Report for PCT/US2020/062289.
Written Opinion for PCT/US2020/062289.
Office Action, CA Application No. 3,159,374, dated May 30, 2023, 4 pages.
Notice—Application Found Allowable, CA Application No. 3,159,374, dated Mar. 13, 2025, 1 page.
Notice of Reasons for Refusal, JP Application No. 2022-530807, dated Jul. 25, 2023, 7 pages.
Decision of Rejection, JP Application No. 2022-530807, dated Jan. 9, 2024, 2 pages.
Decision to Grant a Patent, JP Application No. 2022-530807, dated Jul. 9, 2024, 3 pages.
Examination Report, AU Application No. 2020391206, dated Jan. 10, 2024, 4 pages.
Notice of Reasons for Refusal, JP Application No. 2024-075968, dated Jun. 17, 2025, 4 pages.

(Continued)

*Primary Examiner* — Kimberly Chong
(74) *Attorney, Agent, or Firm* — Nielsen IP Law LLC

(57) ABSTRACT

The present invention relates to compositions and methods for treating neurodegeneration and neurodegenerative diseases associated with axonal degeneration. Neurodegeneration and neurodegenerative diseases associated with axonal degeneration are treated with therapies comprising SARM1 inhibitors such as SARM1 antisense oligonucleotides.

18 Claims, 7 Drawing Sheets

Specification includes a Sequence Listing.

(56)  References Cited

OTHER PUBLICATIONS

Geisler, S. et al., Prevention of vincristine-induced peripheral neuropathy by genetic deletion of SARM1 in mice, Brain, 2016, 3092-3108, 139.

Gerdts, J. et al., SARM1 Activation Triggers Axon Degeneration Locally via NAD+ Destruction, Science, Apr. 24, 2015, 453-457, 348, 6233.

Whitmore, A. et al., The Proapoptotic proteins Bax and Bak are not involved in Wallerian degeneration, Cell Death and Differentiation, 2003, 260-261, 10.

Gerdts, J. et al., Axon self destruction: new links among SARM1, MAPKs, and NAD+ metabolism, Neuron, Feb. 3, 2016, 449-460, 89, 3.

Sasaki, Y. et al., Characterization of Leber Congenital Amaurosis-associated NMNAT1 Mutants, The Journal of Biological Chemistry, Jul. 10, 2015, 17228-17238, 290, 28.

Gerdts, J. et al., Sarm1-Mediated Axon Degeneration Requires Both SAM and TIR Interactions, The Journal of Neuroscience, Aug. 14, 2013, 13569-13580, 33, 33.

Osterloh, J.M. et al., dSarm/Sarm1 Is Required for Activation of an Injury-Induced Axon Death Pathway, Science, Jul. 27, 2012, 481-484, 337, 6093.

Henninger, N. et al., Attenuated traumatic axonal injury and improved functional outcome after traumatic brain injury in mice lacking Sarm1, Brain, 2016, 1094-1105, 139.

* cited by examiner

METHODS AND COMPOSITIONS FOR NEUROPROTECTION

CROSS REFERENCE TO RELATED APPLICATIONS

This application claims the benefit of U.S. Provisional Application No. 62/940,437, filed Nov. 26, 2019, which is herein incorporated by reference in its entirety.

SEQUENCE LISTING

The instant application contains a Sequence Listing, which has been submitted electronically in ASCII format and is hereby incorporated by reference in its entirety. The ASCII copy, created Nov. 23, 2020 is named 2012800-0042_SL.txt, and is 652,394 bytes in size.

BACKGROUND

Axonal degeneration is a hallmark of several neurological disorders including peripheral neuropathies, traumatic brain injury, and neurodegenerative diseases (Gerdts et al., Science, 2015, 348:453-457, hereby incorporated by reference in its entirety). Neurodegenerative diseases and injuries are devastating to both patients and caregivers. Costs associated with these diseases currently exceed several hundred billion dollars annually in the Unites States alone. Since the incidence of many of these diseases and disorders increases with age, their incidence is rapidly increasing as demographics change.

SUMMARY OF THE INVENTION

The present invention is based, at least in part, on the insight that, following axonal damage, Sterile Alpha and TIR motif-containing 1 (SARM1) serves as the central executioner in the axonal degeneration pathway. The present invention provides, among other things, the recognition that antisense oligonucleotides that inhibit SARM1 are particularly beneficial for preventing axonal degeneration.

In one aspect, the present disclosure provides antisense oligonucleotides comprising a sequence having at least 80% identity to a sequence selected from a group consisting of SEQ ID NO: 3-21, 23-26, 38 and 39. In some embodiments, an antisense oligonucleotide comprises a sequence having at least 85% identity to a sequence selected from a group consisting of SEQ ID NO: 3-21, 23-26, 38 and 39. In some embodiments, an antisense oligonucleotide comprises a sequence having at least 90% identity to a sequence selected from a group consisting of SEQ ID NO: 3-21, 23-26, 38 and 39. In some embodiments, an antisense oligonucleotide comprises a sequence selected from a group consisting of SEQ ID NO: 3-21, 23-26, 38 and 39. In some embodiments, an antisense oligonucleotide comprises a sequence selected from a group consisting of SEQ ID NO: 3-2412.

In some embodiments, an antisense oligonucleotide comprises one or more modifications. In some embodiments, one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

In another aspect, the present disclosure comprises pharmaceutical compositions comprising antisense oligonucleotides of the present disclosure. In some embodiments, a pharmaceutical composition comprises a pharmaceutically acceptable carrier.

In another aspect, the present disclosure comprises methods for treating and/or preventing axonal degeneration in a subject, comprising: administering to the subject an antisense oligonucleotide is complementary to a target region of a nucleic acid encoding Sterile Alpha and TIR motif-containing 1 (SARM1).

In another aspect, the present disclosure comprises methods comprising administering to a subject at risk of developing a neurodegenerative disease or disorder an antisense oligonucleotide that is complementary to a target region of a nucleic acid encoding SARM1.

In some embodiments, a target nucleic acid encoding SARM1 is a SARM1 mRNA.

In some embodiments, an antisense oligonucleotide comprises a sequence having at least 80% identity to a sequence selected from a group consisting of SEQ ID NO: 3-21, 23-26, 38 and 39. In some embodiments, an antisense oligonucleotide comprises a sequence having at least 85% identity to a sequence selected from a group consisting of SEQ ID NO: 3-21, 23-26, 38 and 39. In some embodiments, an antisense oligonucleotide comprises a sequence having at least 90% identity to a sequence selected from a group consisting of SEQ ID NO: 3-21, 23-26, 38 and 39. In some embodiments, an antisense oligonucleotide comprises a sequence selected from a group consisting of SEQ ID NO: 3-21, 23-26, 38 and 39. In some embodiments, an antisense oligonucleotide comprises a sequence selected from a group consisting of SEQ ID NO: 3-2412.

In some embodiments, an antisense oligonucleotide comprises one or more modifications. In some embodiments, one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

In some embodiments, administering an antisense oligonucleotide decreases levels of SARM1 mRNA in the subject. In some embodiments, administering an antisense oligonucleotide decreases levels of SARM1 protein in the subject.

In some embodiments, a neurodegenerative disease or disorder comprises an acute or chronic disease or disorder of the peripheral nervous system (PNS), an acute or chronic disease or disorder of the central nervous system (CNS), or a disease associated with neurodegeneration.

In some embodiments, a neurodegenerative disease or disorder comprises a chronic disease or disorder of the PNS. In some embodiments, a chronic disease or disorder of the PNS comprises a systemic disorder, a pain disorder, or a metabolic disease or disorder. In some embodiments, a chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies. In some embodiments, a systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa. In some embodiments, a pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes. In some embodiments, a metabolic disease or disorder comprises diabetes mellitus, hypoglycemia, uremia, hypothyroidism, hepatic failure, polycythemia, amyloidosis, acromegaly, *porphyria*, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

In some embodiments, a neurodegenerative disease or disorder comprises an acute disease or disorder of the peripheral nervous system. In some embodiments, an acute disease or disorder of the PNS is the result of a mechanical injury, thermal injury, or injury from a chemical agent or chemotherapy. In some embodiments, a mechanical injury comprises a compression or entrapment injury or a pressure injury. In some embodiments, a compression or entrapment injury comprises carpal tunnel syndrome, direct trauma, a penetrating injury, a contusion, a fracture or a dislocated bone. In some embodiments, a pressure injury comprises pressure involving superficial nerves, pressure from a tumor or increased intraocular pressure. In some embodiments, a chemical agent or chemotherapy comprises a cytotoxic anticancer agent, thalidomide, an epothilone, a taxane, a *vinca* alkaloid, a proteasome inhibitor, a platinum-based drug or an auristatin. In some embodiments, an epothilone is ixabepilone. In some embodiments, a taxane is paclitaxel or docetaxel. In some embodiments, a *vinca* alkaloid is vinblastine, vinorelbine, vincristine, or vindesine. In some embodiments, a proteasome inhibitor is bortezomib. In some embodiments, a platinum-based drug is cisplatin, oxaliplatin, or carboplatin. In some embodiments, an auristatin is conjugated monomethyl auristatin E.

In some embodiments, a neurodegenerative disease or disorder comprises a chronic disease or disorder of the CNS. In some embodiments, a chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

In some embodiments, a chronic disease or disorder of the CNS comprises an optic nerve disorder, a traumatic CNS injury, or a metabolic disease or disorder. In some embodiments, an optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide. In some embodiments, a traumatic CNS injury comprises a traumatic brain injury (TBI), a spinal cord injury, traumatic axonal injury or chronic traumatic encephalopathy (CTE). In some embodiments, a metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

In some embodiments, a neurodegenerative disease or disorder comprises an acute disease or disorder of the CNS. In some embodiments, an acute disease or disorder of the CNS comprises an ischemia, a traumatic CNS injury, injury from a chemical agent, thermal injury, or viral encephalitis. In some embodiments, an ischemia comprises cerebral ischemia, hypoxic demyelination, ischemic demyelination, ischemic optic neuropathy, or non-arteritic anterior ischemic optic neuropathy. In some embodiments, a traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer. In some embodiments, a viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia). In some embodiments, a neurodegenerative disease or disorder results from blood clotting issues, inflammation, obesity, aging, stress, cancer, or diabetes.

In some embodiments, a subject is a human. In some embodiments, a subject is a patient with one or more risk factors for developing a condition involving axonal degeneration. In some embodiments, one or more risk factors for developing a condition involving axonal degeneration comprise age, one or more genetic risk factors for neurodegeneration, family history, engaging in one or more high-risk activities, one or more biomarkers of neurodegeneration, or a combination thereof. In some embodiments, one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof. In some embodiments, engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing. In some embodiments, one or more biomarkers of neurodegeneration comprise: concentration of neurofilament light chain protein (NF-L) in one or more of: a cerebrospinal fluid (CSF) sample, a blood sample, and a plasma sample from the subject; concentration of neurofilament heavy chain protein (NF-H) in one or more of: a cerebrospinal fluid (CSF) sample, a blood sample, and a plasma sample from the subject; concentration of Ubiquitin C-terminal Hydrolase L1 (UCH-L1) in one or more of: a cerebrospinal fluid (CSF) sample, a blood sample, and a plasma sample from the subject; concentration of alpha-synuclein in one or more of: a cerebrospinal fluid (CSF) sample, a blood sample, and a plasma sample from the subject; constitutive NAD+ levels in neurons and/or axons of the subject; constitutive cADPR levels in neurons and/or axons of the subject; levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

BRIEF DESCRIPTION OF THE DRAWING

The foregoing and other features and advantages of the present invention will be more fully understood from the following detailed description of illustrative embodiments taken in conjunction with the accompanying drawings. It should be understood that the present invention is not limited to the precise arrangements and instrumentalities of the embodiments shown in the drawings.

DEFINITIONS

Figure 1:
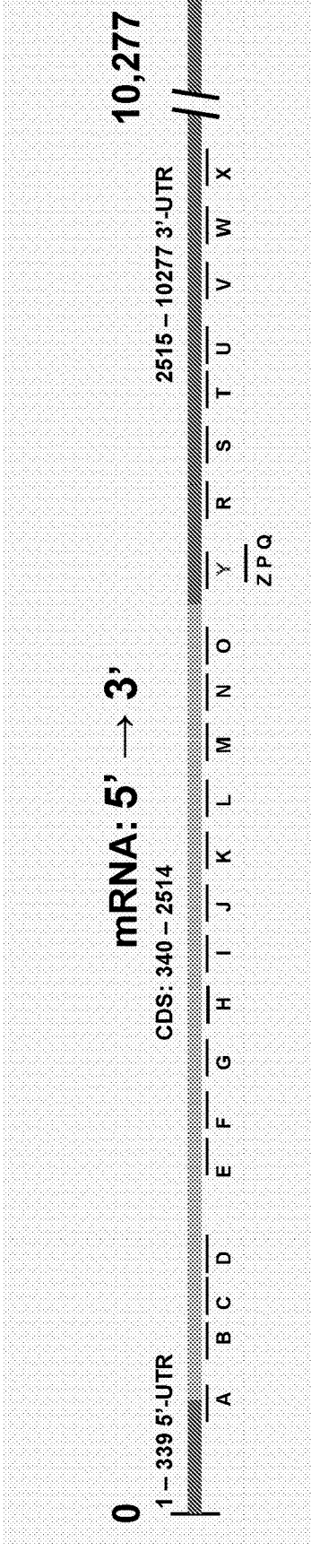
FIG. 1 shows a map of antisense oligonucleotides complementary to human SARM1 mRNA.

Binding: It will be understood that the term "binding", as used herein, typically refers to an association (e.g., a non-covalent or covalent association) between or among two or more entities. "Direct" binding involves physical contact between entities or moieties; indirect binding involves physical interaction by way of physical contact with one or more intermediate entities. Binding between two or more entities can typically be assessed in any of a variety of contexts-including where interacting entities or moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

In some embodiments, a biomarker may be or comprise a marker for neurodegeneration, or for likelihood that a neurodegenerative disease, disorder or condition may develop, occur, or reoccur. In some embodiments, a biomarker may be or comprise a marker of neurodegeneration a therapeutic outcome, or likelihood thereof. Thus, in some embodiments, a biomarker is predictive, in some embodiments, a biomarker is prognostic, and in some embodiments, a biomarker is diagnostic, of a neurodegenerative disease, disorder or condition. In some embodiments changes in biomarker levels can be detected via cerebral spinal fluid (CSF), plasma and/or serum. In some embodiments a biomarker can be a detectable signal produced by medical imaging techniques including, but not limited to, magnetic resonance imaging (MRI), positron emission-tomography (PET), and/or computed tomography (CT). In some embodiments, a biomarker can be a detectable change in electrophysiological properties.

In some embodiments, neurodegeneration may be assessed, for example, by detecting an increase and/or decrease in the concentration of neurofilament light chain protein (NF-L) and/or neurofilament heavy chain protein (NF-H) contained in bodily fluids from a subject including, but not limited to, cerebral spinal fluid, blood, serum and/or plasma. In some embodiments, the incidence and/or progression of neurodegeneration can be assessed via positron emission tomography (PET) with a synaptic vesicle glycoprotein 2a (SV2A) ligand. In some embodiments, a detectable change in constitutive NAD+ and/or cADPR levels in neurons can be used to assess neurodegeneration.

In some embodiments, a detectable change in one or more neurodegeneration associated proteins in a subject, relative to a healthy reference population can be used as a biomarker of neurodegeneration. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, an increase in cytokines and/or chemokines, including, but not limited to, Ccl2, Ccl7, Ccl12, Csf1, and/or Il6, can be used as a biomarker of neurodegeneration.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination: The terms "combination therapy" or "in combination with", as used herein, refer to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially (e.g., all "doses" of a first regimen are administered prior to administration of any doses of a second regimen) such that the agents have simultaneous biologically activity within a subject. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, aa-helix character, ββ-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Neurodegeneration: As used herein, the term "neurodegeneration" refers to a reduction in one or more features, structures, function, or characteristics of a neuron or neuronal tissue. In some embodiments, neurodegeneration is observed as a pathological reduction in an organism. Those skilled in the art will appreciate that neurodegeneration is associated with certain diseases, disorders and conditions, including those that affect humans. In some embodiments, neurodegeneration may be transient (e.g., as sometimes occurs in association with certain infections and/or chemical or mechanical disruptions); in some embodiments, neurodegeneration may be chronic and/or progressive (e.g., as is often associated with certain diseases, disorders or conditions such as, but not limited to, Parkinson's disease, amyotrophic lateral sclerosis, multiple sclerosis, Huntington disease, or Alzheimer's disease). In some embodiments, neurodegeneration may be assessed, for example, by detecting in a subject an increase in a biomarker associated with neurodegeneration. In some embodiments, neurodegeneration may be assessed, for example, by detecting in a subject a decrease in a biomarker associated with neurodegeneration. Alternatively or additionally, in some embodiments, neurodegeneration may be assessed by magnetic resonance imaging (MRI), biomarkers contained in cerebral spinal fluid, or other biomarkers observed in subjects. In some embodiments, neurodegeneration is defined as a score below 24 on the mini-mental state examination. In some embodiments, neurodegeneration refers to loss of synapses. In some embodiments, neurodegeneration refers to a reduction in neural tissue relating to a traumatic injury (e.g. exposure to an external force which disrupts the integrity of the neural tissue). In some embodiments, neurodegeneration refers to a reduction in peripheral neural tissue. In some embodiments, neurodegeneration refers to a reduction in central nervous tissue.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, and are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity. In some embodiments, a nucleic acid comprises a small interfering RNA (siRNA), a short hairpin RNA (shRNA), an antisense oligonucleotide, a microRNA, a gapmer, or an aptamer.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66:1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition. In some embodiments, treatment may be administered to a subject to prevent the risk of developing pathology associated with or resulting from a medical procedure and/or treatment.

DETAILED DESCRIPTION

Axonal Degeneration and SARM1

The present invention may be used to treat a subject who is suffering from or susceptible to axonal degeneration. Axonal degeneration is a major pathological feature of neurological diseases such as, but not limited to, Alzheimer's disease, Parkinson's disease, amyotrophic lateral sclerosis (ALS), multiple sclerosis, diabetic peripheral neuropathy, chemotherapy-induced peripheral neuropathy, inherited neuropathy, traumatic brain injury, and/or glaucoma. Damaged or unhealthy axons are eliminated via an intrinsic self-destruction program known as Wallerian degeneration, which is distinct from traditional cellular death pathways like apoptosis (Gerdts, J., et al., *Neuron,* 2016, 89, 449-460; Whitmore, A. et al., *Cell Death Differ.,* 2003, 10, 260-261, each of which is hereby incorporated by reference in its entirety). During Wallerian degeneration, a nerve undergoes selective breakdown of the axon segment distal to an injury, whereas the proximal axon segment and cell body remain intact. Axonal degeneration following an injury is characterized by the sequential depletion of NMNAT2, $NAD^+$ and ATP, followed by neurofilament proteolysis and axonal fragmentation occurring approximately 8 to 24 hours after the original injury (Gerdts, J., et al., *Neuron,* 2016, 89, 449-460, hereby incorporated by reference in its entirety).

It has recently been discovered that knocking-down or eliminating the expression of SARM1 leads to long-lasting protection of sensory neurons against injury-induced axonal degeneration (Gerdts et al., *J. Neurosci,* 2013, 33, 13569-13580, which is hereby incorporated by reference in its entirety). Following axonal damage, SARM1 serves as the central executioner in the axonal degeneration pathway. Activated SARM1 is a highly effective NADase that depletes local axonal $NAD^+$ reserves within minutes to a few hours after activation, leading to a local bioenergetic crisis, followed by rapid axonal degeneration. Activation of SARM1 via axonal injury or forced dimerization of SARM1-TIR domains promotes rapid and catastrophic depletion of $NAD^+$, followed soon after by axonal degeneration, which highlights the central role of $NAD^+$ homeostasis in axonal integrity (Gerdts, J., et al., *Science,* 2015, 348, 453-457). SARM1 is required for this injury-induced NAD$^+$ depletion both in vitro and in vivo and SARM1 activation triggers axon degeneration locally via NAD$^+$ destruction (Gerdts et al., et al., *Science,* 2015, 348, 452-457; Sasaki et al., *J. Biol. Chem.* 2015, 290, 17228-17238, each of which is hereby incorporated by reference in its entirety).

The protein sequence of wild-type human SARM1 is as follows:

```
                                      (SEQ ID NO: 1)
MVLTLLLSAYKLCRFFAMSGPRPGAERLAVPGPDGGGGTGPWWAAGGRGP

REVSPGAGTEVQDALERALPELQQALSALKQAGGARAVGAGLAEVFQLVE

EAWLLPAVGREVAQGLCDAIRLDGGLDLLLRLLQAPELETRVQAARLLEQ

ILVAENRDRVARIGLGVILNLAKEREPVELARSVAGILEHMFKHSEETCQ

RLVAAGGLDAVLYWCRRTDPALLRHCALALGNCALHGGQAVQRRMVEKRA

AEWLFPLAFSKEDELLRLHACLAVAVLATNKEVEREVERSGTLALVEPLV

ASLDPGRFARCLVDASDTSQGRGPDDLQRLVPLLDSNRLEAQCIGAFYLC

AEAAIKSLQGKTKVFSDIGAIQSLKRLVSYSTNGTKSALAKRALRLLGEE

VPRPILPSVPSWKEAEVQTWLQQIGFSKYCESFREQQVDGDLLLRLTEEE

LQTDLGMKSGITRKRFFRELTELKTFANYSTCDRSNLADWLGSLDPRFRQ

YTYGLVSCGLDRSLLHRVSEQQLLEDCGIHLGVHRARILTAAREMLHSPL

PCTGGKPSGDTPDVFISYRRNSGSQLASLLKVHLQLHGFSVFIDVEKLEA

GKFEDKLIQSVMGARNFVLVLSPGALDKCMQDHDCKDWVHKEIVTALSCG

KNIVPIIDGFEWPEPQVLPEDMQAVLTFNGIKWSHEYQEATIEKIIRFLQ

GRSSRDSSAGSDTSLEGAAPMGPT.
```

Genetic loss-of-function studies indicate that SARM1 serves as the central executioner of the axonal degeneration pathway following an injury. Genetic deletion or knockout of SARM1 allows for preservation of axons for 14 or more days after nerve transection (Osterloh, J. M., et al., *Science,* 2012, 337, 481-484; Gerdts, J., et al. *J. Neurosci.,* 2013, 33, 13569-13580, each of which is hereby incorporated by reference in its entirety) and also improves functional outcomes in mice after traumatic brain injury (Henninger, N. et al., *Brain,* 139, 2016, 1094-1105, which is hereby incorporated by reference in its entirety). In addition to the direct role SARM1 plays in axonal injury, SARM1 is also required for the axonal degeneration observed in chemotherapy-induced peripheral neuropathy (CIPN). Loss of SARM1 prevents CIPN, inhibiting both the axonal degeneration and the heightened pain sensitivity that develops after chemotherapeutic vincristine treatment (Geisler et al, *Brain,* 2016, 139, 3092-3108, which is hereby incorporated by reference in its entirety).

SARM1 Antisense Oligonucleotides

In some embodiments, the present disclosure provides antisense oligonucleotides. In some embodiments, an antisense oligonucleotide is an RNase H-dependent oligonucleotide, wherein the antisense oligonucleotide induces the degradation of mRNA. In some embodiments, an antisense oligonucleotide is a steric-blocker oligonucleotide, wherein the antisense oligonucleotide physically prevents or inhibits the progression of splicing or translational machinery. Antisense oligonucleotides of the present disclosure are capable of hybridizing to a target nucleic acid, resulting in at least one antisense activity. In some embodiments, antisense activity comprises degradation of a target nucleic acid by RNase H. In some embodiments, antisense activity comprises an antisense oligonucleotide physically preventing or inhibiting the progression of splicing or translational machinery.

In some embodiments, antisense oligonucleotides specifically hybridize to one or more target nucleic acids. In some embodiments, a target nucleic acid comprises a full-length mRNA. In some embodiments, a target nucleic acid comprises a region of an mRNA. In some embodiments, antisense oligonucleotides of the present invention hybridize to the same target nucleic acid. In some embodiments, antisense oligonucleotides of the present invention hybridize to different target nucleic acids. In some embodiments, a specifically hybridizing antisense oligonucleotide has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In some embodiments, the present disclosure provides antisense oligonucleotides that are fully complementary to a target nucleic acid over the entire length of the antisense oligonucleotide. In some embodiments, an antisense oligonucleotide is 99% complementary to a target nucleic acid over the entire length of the antisense oligonucleotide. In some embodiments, an antisense oligonucleotide is 95% complementary to a target nucleic acid over the entire length of the antisense oligonucleotide. In some embodiments, an antisense oligonucleotide is 90% complementary to a target nucleic acid over the entire length of the antisense oligonucleotide. In some embodiments, an antisense oligonucleotide is 85% complementary to a target nucleic acid over the entire length of the antisense oligonucleotide. In some embodiments, an antisense oligonucleotide is 80% complementary to a target nucleic acid over the entire length of the antisense oligonucleotide. In some embodiments, an antisense oligonucleotide is between 80% and 99% complementary to a target nucleic acid over the entire length of the antisense oligonucleotide. In some embodiments, an antisense oligonucleotide comprises a region that is fully complementary to a target nucleic acid and is at least 80% complementary to the target nucleic acid over the entire length of the oligonucleotide. In some embodiments, the region of full complementarity is from 6 to 14 nucleobases in length.

In some embodiments, an antisense oligonucleotide comprises a sequence having at least 80% identity to a sequence selected from a group consisting of SEQ ID NO: 3-26. In some embodiments, an antisense oligonucleotide comprises a sequence having at least 85% identity to a sequence selected from a group consisting of SEQ ID NO: 3-26. In some embodiments, an antisense oligonucleotide comprises a sequence having at least 90% identity to a sequence selected from a group consisting of SEQ ID NO: 3-26. In some embodiments, an antisense oligonucleotide comprises a sequence selected from a group consisting of SEQ ID NO: 3-26. In some embodiments, an antisense oligonucleotide comprises a sequence selected from a group consisting of SEQ ID NO: 3-2081.

In some embodiments, an antisense oligonucleotide comprises a sequence having at least 80% identity to a sequence selected from a group consisting of SEQ ID NO: 3-21, 23-26, 38 and 39. In some embodiments, an antisense oligonucleotide comprises a sequence having at least 85% identity to a sequence selected from a group consisting of SEQ ID NO: 3-21, 23-26, 38 and 39. In some embodiments, an antisense oligonucleotide comprises a sequence having at least 90% identity to a sequence selected from a group consisting of SEQ ID NO: 3-21, 23-26, 38 and 39. In some embodiments, an antisense oligonucleotide comprises a sequence selected from a group consisting of SEQ ID NO: 3-21, 23-26, 38 and 39. In some embodiments, an antisense oligonucleotide comprises a sequence selected from a group consisting of SEQ ID NO: 3-2412.

In some embodiments, an antisense oligonucleotide comprises a sequence having at least 80% identity to a sequence selected from a group consisting of SEQ ID NO: 8, 9, 13, 22, 38, and 549. In some embodiments, an antisense oligonucleotide comprises a sequence having at least 85% identity to a sequence selected from a group consisting of SEQ ID NO: 8, 9, 13, 22, 38, and 549. In some embodiments, an antisense oligonucleotide comprises a sequence having at least 90% identity to a sequence selected from a group consisting of SEQ ID NO: 8, 9, 13, 22, 38, and 549. In some embodiments, an antisense oligonucleotide comprises a sequence selected from a group consisting of SEQ ID NO: 8, 9, 13, 22, 38, and 549.

In some embodiments, a target nucleic acid is an endogenous RNA molecule. In some embodiments, a target nucleic acid is an exogenous RNA molecule. In some embodiments, a target nucleic acid is a pre-mRNA. In some embodiments, a target nucleic acid is a mature mRNA. In some embodiments, a target nucleic acid is a SARM1 transcript.

In some embodiments, an antisense oligonucleotide of the present disclosure is complementary to a region of a SARM1 mRNA. In some embodiments, an antisense oligonucleotide is complementary to a region of a 5' untranslated region (UTR) of a SARM1 mRNA. In some embodiments, an antisense oligonucleotide is complementary to a coding region of a SARM1 mRNA. In some embodiments, an antisense oligonucleotide is complementary to a region of a 3' UTR of a SARM1 mRNA. In some embodiments, an antisense oligonucleotide of the present invention is complementary to a region of a SARM1 mRNA as illustrated in FIG. 1 and Table 1. Table 1 includes exemplary SARM1 antisense oligonucleotide sequences, region of complementarity in SAMR1 mRNA (5' UTR, coding region (CDS), or 3' UTR), oligonucleotide starting position (starting position from 5' end of SARM1 mRNA) and code letter corresponding to antisense oligonucleotide in FIG. 1.

TABLE 1

Antisense oligonucleotide sequences, region of complementarity and starting position

| SEQ ID NO: | Antisense Oligonucleotide Sequence (5'-3') | Region | Oligo Start | Code |
|---|---|---|---|---|
| 3 | GGCCTCCTCCACCAGTTGGA | CDS | 626 | B |
| 4 | GCAGGCTCTTGATGGCAGCC | CDS | 1395 | E |
| 5 | GCCATCCACCTGCTGCTCCC | CDS | 1640 | H |
| 6 | TCCCCACTGGGTTTGCCACC | CDS | 1999 | L |
| 7 | ACTTGCCTGCTTCCAGCTTC | CDS | 2127 | M |

TABLE 1-continued

Antisense oligonucleotide sequences, region of complementarity and starting position

| SEQ ID NO: | Antisense Oligonucleotide Sequence (5'-3') | Region | Oligo Start | Code |
|---|---|---|---|---|
| 8 | CTTGTCCAGTGCTCCAGGTG | CDS | 2204 | N |
| 9 | GCACAGCCTGCATGTCCTCA | CDS | 2346 | O |
| 10 | CCCAGGTTGTCTCAGCCCAG | 3'UTR | 2596 | Q |
| 11 | TCCCTTCCCTCTCCAGATAC | 3'UTR | 2688 | R |
| 12 | TGCAGAACCACCCCCACCCC | 3'UTR | 2814 | S |
| 13 | GCCCAGGCCCTTGCTCAGAA | 3'UTR | 2932 | T |
| 14 | GGCACTCATCCCTGGCTGGC | 3'UTR | 2958 | U |
| 15 | CCCCATGCCCAGACCCAGGC | 3'UTR | 3231 | W |
| 16 | GCCTCTTTCCACAGAGCTGC | 3'UTR | 3420 | X |
| 17 | TCTCAGCCACCAGGATCTGC | CDS | 786 | D |
| 18 | GAGCTCCCTAAAGAACCTCT | CDS | 1730 | J |
| 19 | CCAGGTTGTCTCAGCCCAGG | 3'UTR | 2595 | P |
| 20 | GGTGCAGCAGGGAGCGGTCC | CDS | 1869 | K |
| 21 | GCAGCGTCAGGACCATGGGC | 5'UTR | 336 | A |
| 22 | ACCAGGCGTTTCAGGCTCTG | CDS | 1453 | F |
| 23 | CACCTCCTCGCCCAGCAGGC | CDS | 1523 | G |
| 24 | GTCTGGAGTTCCTCCTCCGT | CDS | 1678 | I |
| 25 | CCCTCGCCCTGGATGTGGCA | 3'UTR | 3124 | V |
| 26 | GGCCTGCACACGCGTCTCCA | CDS | 752 | C |
| 38 | AGGTTGTCTCAGCCCAGGGA | 3'UTR | 2593 | Y |
| 39 | CAGGTTGTCTCAGCCCAGGG | 3'UTR | 2594 | Z |

In some embodiments, an antisense oligonucleotide of the present disclosure comprises an oligonucleotide consisting of 8 to 30 linked nucleosides and having a nucleobase sequence comprising a complementary region comprising at least 8 contiguous nucleobases complementary to a target region of equal length of a SARM1 transcript.

In some embodiments, an antisense oligonucleotide comprises RNA. In some embodiments, an antisense oligonucleotide comprises DNA. In some embodiments, an antisense oligonucleotide comprises both RNA and DNA. In some embodiments, an antisense oligonucleotide is between 5 and 100 nucleotides in length. In some embodiments, an antisense oligonucleotide is between 5 and 90 nucleotides in length. In some embodiments, an antisense oligonucleotide is between 5 and 80 nucleotides in length. In some embodiments, an antisense oligonucleotide is between 5 and 70 nucleotides in length. In some embodiments, an antisense oligonucleotide is between 5 and 60 nucleotides in length. In some embodiments, an antisense oligonucleotide is between 5 and 50 nucleotides in length. In some embodiments, an antisense oligonucleotide is between 5 and 40 nucleotides in length. In some embodiments, an antisense oligonucleotide is between 5 and 30 nucleotides in length. In some embodiments, an antisense oligonucleotide is between 5 and 25 nucleotides in length. In some embodiments, an antisense oligonucleotide is between 5 and 20 nucleotides in length. In some embodiments, an antisense oligonucleotide is between 5 and 15 nucleotides in length. In some embodiments, an antisense oligonucleotide is between 5 and 10 nucleotides in length. In some embodiments, an antisense oligonucleotide is between 10 and 100 nucleotides in length. In some embodiments, an antisense oligonucleotide is between 15 and 100 nucleotides in length. In some embodiments, an antisense oligonucleotide is between 20 and 100 nucleotides in length. In some embodiments, an antisense oligonucleotide is between 25 and 100 nucleotides in length. In some embodiments, an antisense oligonucleotide is between 30 and 100 nucleotides in length. In some embodiments, an antisense oligonucleotide is between 40 and 100 nucleotides in length. In some embodiments, an antisense oligonucleotide is between 50 and 100 nucleotides in length. In some embodiments, an antisense oligonucleotide is between 60 and 100 nucleotides in length. In some embodiments, an antisense oligonucleotide is between 70 and 100 nucleotides in length. In some embodiments, an antisense oligonucleotide is between 90 and 100 nucleotides in length. In some embodiments, an antisense oligonucleotide is 10, 11, 12, 13, 14, 15, 16, 17, 18, 19, 20, 21, 22, 23, 24, 25, 26, 27, 28, 29, or 30 nucleotides in length. In some embodiments, an antisense oligonucleotide is 20 nucleotides in length.

In some embodiments, an antisense oligonucleotide comprises one or more modifications. In some embodiments, one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof. In some embodiments, any antisense oligonucleotide described herein comprises internucleotide linkages of the following pattern (5' to 3'): $R_SR_OR_SR_OR_SD_SD_SD_SD_SD_SD_SD_SD_SD_SD_S$-$R_OR_SR_OR_S$, wherein $R_S$ is an RNA (2'-MOE) phosphorothioate bond, $R_O$ is an RNA (2'-MOE) phosphodiester bond and $D_S$ is a DNA phosophorothioate bond. In some embodiments, an antisense oligonucleotide comprises SEQ ID NO: 2410. In some embodiments, an antisense oligonucleotide comprises SEQ ID NO: 2411. In some embodiments, an antisense oligonucleotide comprises SEQ ID NO: 2412.

Methods of Treating Neurodegeneration

Methods described herein include treating and/or preventing axonal degeneration in a subject. In some embodiments, methods described herein include administering to the subject an SARM1 antisense agent. In some embodiments, methods described herein include administering to the subject an SARM1 antisense agent. Methods described herein include administering to a subject at risk of developing a neurodegenerative disease or disorder an SARM1 antisense agent. In some embodiments, an SARM1 antisense agent is an SARM1 antisense oligonucleotide.

Diseases, Disorders, and Conditions

In some embodiments, the present disclosure provides methods for treating subjects suffering from one or more diseases, disorders, or conditions. In some embodiments, the one or more diseases, disorders, or conditions are mediated by SARM1.

In some embodiments, a neurodegenerative disease or disorder comprises an acute or chronic disease or disorder of the peripheral nervous system (PNS), an acute or chronic disease or disorder of the central nervous system (CNS), or a disease associated with neurodegeneration.

In some embodiments, a neurodegenerative disease or disorder comprises an acute disease or disorder of the PNS.

In some embodiments, an acute disease or disorder of the PNS is the result of a mechanical injury, thermal injury, or injury from a chemical agent or chemotherapy. In some embodiments, a mechanical injury comprises a compression or entrapment injury or a pressure injury. In some embodiments, a compression or entrapment injury comprises carpal tunnel syndrome, direct trauma, a penetrating injury, a contusion, a fracture or a dislocated bone. In some embodiments, a pressure injury comprises pressure involving superficial nerves, pressure from a tumor or increased intraocular pressure. In some embodiments, a chemical agent or chemotherapy comprises a cytotoxic anticancer agent, thalidomide, an epothilone, a taxane, a vinca alkaloid, a proteasome inhibitor, a platinum-based drug or an auristatin. In some embodiments, an epothilone is ixabepilone. In some embodiments, a taxane is paclitaxel or docetaxel. In some embodiments, a vinca alkaloid is vinblastine, vinorelbine, vincristine, or vindesine. In some embodiments, a proteasome inhibitor is bortezomib. In some embodiments, a platinum-based drug is cisplatin, oxaliplatin, or carboplatin. In some embodiments, an auristatin is conjugated monomethyl auristatin E.

In some embodiments, a neurodegenerative disease or disorder comprises a chronic disease or disorder of the PNS. In some embodiments, a chronic disease or disorder of the PNS comprises a systemic disorder, a pain disorder, or a metabolic disease or disorder.

In some embodiments, a chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

In some embodiments, a systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

In some embodiments, a pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

In some embodiments, a metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

In some embodiments, a neurodegenerative disease or disorder comprises an acute disease or disorder of the CNS. In some embodiments, an acute disease or disorder of the CNS comprises an ischemia, a traumatic CNS injury, injury from a chemical agent, thermal injury, or viral encephalitis.

In some embodiments, an ischemia comprises cerebral ischemia, hypoxic demyelination, ischemic demyelination, ischemic optic neuropathy, or non-arteritic anterior ischemic optic neuropathy.

In some embodiments, a traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

In some embodiments, a viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

In some embodiments, a neurodegenerative disease or disorder comprises a chronic disease or disorder of the CNS.

In some embodiments, a chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

In some embodiments, a chronic disease or disorder of the CNS comprises an optic nerve disorder, a traumatic CNS injury, or a metabolic disease or disorder.

In some embodiments, an optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

In some embodiments, a traumatic CNS injury comprises a traumatic brain injury (TBI), a spinal cord injury, traumatic axonal injury or chronic traumatic encephalopathy (CTE).

In some embodiments, a metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

In some embodiments, a neurodegenerative disease or disorder comprises a disease associated with neurodegeneration. In some embodiments, a neurodegenerative disease or disorder results from blood clotting issues, inflammation, obesity, aging, stress, cancer, or diabetes.

In some embodiments, a subject is a human. In some embodiments, a subject is at risk of developing a condition characterized by axonal degeneration. In some embodiments, a subject is a patient with one or more risk factors for developing a condition involving axonal degeneration. In some embodiments, one or more risk factors for developing a condition involving axonal degeneration comprise age, one or more genetic risk factors for neurodegeneration, family history, engaging in one or more high-risk activities, one or more biomarkers of neurodegeneration, or a combination thereof.

In some embodiments, one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

In some embodiments, a subject has a condition characterized by axonal degeneration. In some embodiments, a subject has been diagnosed with a condition characterized by axonal degeneration.

In some embodiments, engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

In some embodiments, one or more biomarkers of neurodegeneration comprises: concentration of neurofilament light chain protein (NF-L) in one or more of: a cerebrospinal fluid (CSF) sample, a blood sample, and a plasma sample from the subject; concentration of neurofilament heavy chain protein (NF-H) in one or more of: a cerebrospinal fluid (CSF) sample, a blood sample, and a plasma sample from the subject; concentration of Ubiquitin C-terminal Hydrolase L1 (UCH-L1) in one or more of: a cerebrospinal fluid (CSF) sample, a blood sample, and a plasma sample from the subject; concentration of alpha-synuclein in one or more of: a cerebrospinal fluid (CSF) sample, a blood sample, and a plasma sample from the subject; constitutive $NAD^+$ levels in neurons and/or axons of the subject; constitutive cADPR levels in neurons and/or axons of the subject; levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

In some embodiments, a therapy provided herein is characterized such that, when administered to a population of subjects, the therapy reduces one or more symptoms or features of neurodegeneration. For example, in some embodiments, a relevant symptom or feature may be selected from the group consisting of extent, rate, and/or timing of neuronal disruption.

Subjects

In some embodiments, a composition as described herein is administered to subjects suffering from or susceptible to a disease, disorder or condition as described herein; in some embodiments, such a disease, disorder or condition is characterized by axonal degeneration, such as one of the conditions mentioned herein.

In some embodiments, a subject to whom a composition is administered as described herein exhibits one or more signs or symptoms associated with axonal degeneration; in some embodiments, the subject does not exhibit any signs or symptoms of neurodegeneration.

In some embodiments, provided methods comprise administering a composition to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population of in need thereof. In some embodiments, the population is drawn from individuals who engage in activities where the potential for traumatic neuronal injury is high. In some embodiments, the population is drawn from athletes who engage in contact sports or other high-risk activities.

In some embodiments, the subject is at risk of developing a condition characterized by axonal degeneration. In some embodiments, the subject is identified as being at risk of axonal degeneration, e.g., based on the subject's genotype, a diagnosis of a condition associated with axonal degeneration, and/or exposure to an agent and/or a condition that induces axonal degeneration.

In some embodiments, the patient is at risk of developing a neurodegenerative disorder. In some embodiments the patient is elderly. In some embodiments, the patient is known to have a genetic risk factor for neurodegeneration. In some embodiments, the patient has a family history of neurodegenerative disease. In some embodiments, the patient expresses one or more copies of a known genetic risk factor for neurodegeneration (Lill et al., *Semin Neurol,* 2011, 31:531-541, hereby incorporated by reference in its entirety). In some embodiments, the patient is drawn from a population with a high incidence of neurodegeneration. For example, in some embodiments, the patient has a hexanucleotide repeat expansion in chromosome 9 open reading frame 72. In some embodiments, the patient has one or more copies of the Apolipoprotein E 4 (ApoE4) allele.

In some embodiments, the patient has one or more copies of a disease-causing mutation in APP, PSEN1, or PSEN2. In some embodiments, the patient has one or more copies of a disease-associated polymorphism in or near the following genes: ABCA7, APOE, BIN1, CD2AP, CD33, CLU, CR1, MS4A4E, MS4A6A, and PICALM.

In some embodiments, the patient has one or more copies of a disease-causing mutation in EIF4G1, LRRK2, PARK2, PARK7, PINK1, SNCA, or VPS35. In some embodiments, the patient has one or more copies of a disease-associated polymorphism in or near the following genes: ACMSD/TMEM163, BST1, CCDC62/HIP1R, FAM47E/STBD1, GAK/DGKQ, GBA, GPNMB, QWA_8p22/FGF20, HLA-II, LRRK2, MAPT, MCCC1/LAMP3, PARK16, SETD1A/STX1B, SNCA, SREBF1/RAI1, STK29, and SYT11/RAB25.

In some embodiments, the patient has one or more copies of a disease-causing mutation in C9ORF72, CHMP2B, GRN, MAPT, or VCP. In some embodiments, the patient has one or more copies of a disease-associated polymorphism in or near the TMEM106B gene.

Figure 4:
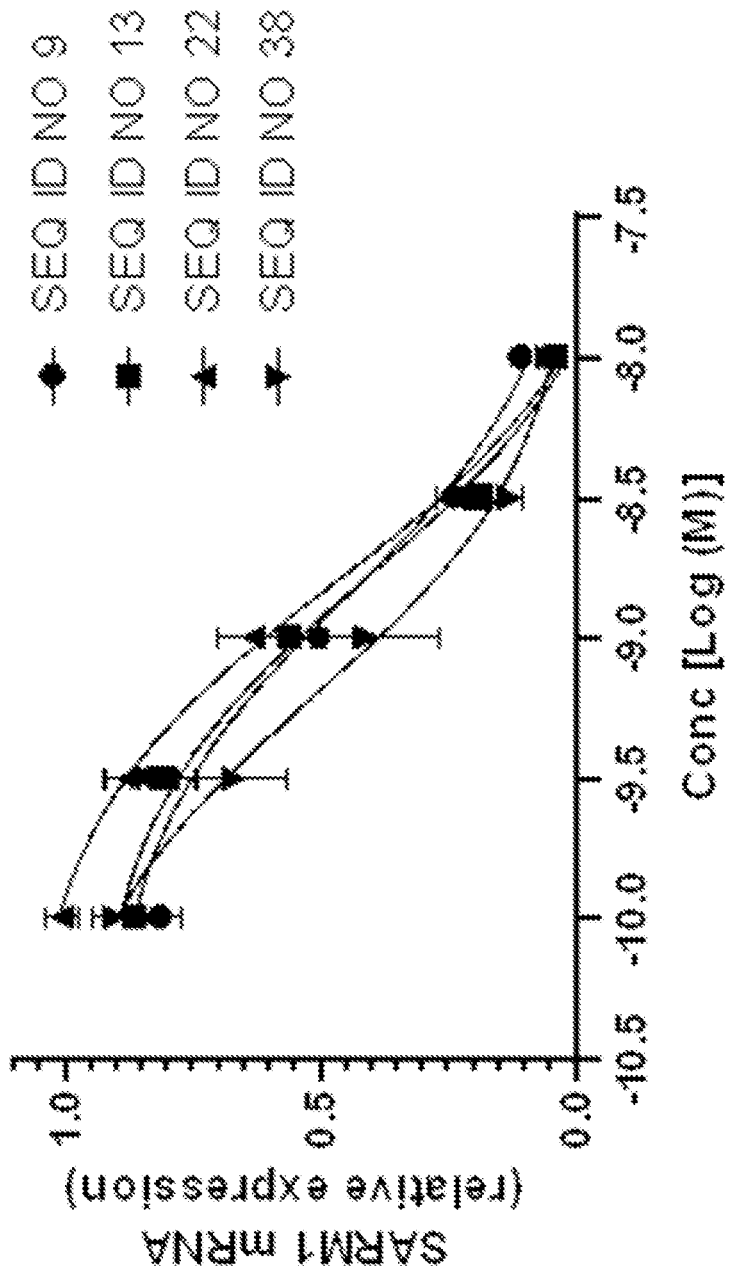
FIG. 4 shows a graph illustrating relative SARM1 mRNA expression in human induced pluripotent stem cells (IPSC)-derived motor neurons following transfection with antisense oligonucleotides targeting the SARM1 transcript.

In some embodiments, the patient has one or more copies of a disease-causing mutation in ANG, ALS2, C9ORF72, FIG. 4, FUS, OPTN, SETX, SOD1, SPG11, TARDBP, UBQLN2, VAPB, or VCP. In some embodiments, the patient has one or more copies of a disease-associated polymorphism in or near the following genes: GWA_9p21.2, UNC13A and ATXN2.

In some embodiments, subjects to which a composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in to the brain cavity or innervated region of the body. In some embodiments, a traumatic neuronal injury is a force which causes the axons to deform, stretch, crush or sheer.

In some embodiments, the subject engages in an activity identified as a risk factor for neuronal degeneration, e.g., a subject that engages in contact sports or occupations with a high chance for traumatic neuronal injury.

For example, the subject may be a patient who is receiving, or is prescribed, a chemotherapy associated with peripheral neuropathy. Examples of chemotherapeutic agents include, but are not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), auristatins (e.g., Auristatin E) and platinum-based drugs (e.g., cisplatin, oxaliplatin, and carboplatin).

In some embodiments, provided methods comprise administering a composition as described herein to a patient or patient population based on the presence or absence of one or more biomarkers. In some embodiments, provided methods further comprise monitoring the level of a biomarker in a patient or patient population and adjusting the dosing regimen accordingly.

Dosing

Those of skill in the art will appreciate that, in some embodiments, the exact amount of a particular SARM1 antisense agent included in and/or delivered by administration of a pharmaceutical composition or regimen as described herein may be selected by a medical practitioner and may be different for different subjects, for example, upon consideration of one or more of species, age, and general condition of the subject, and/or identity of the particular SARM1 antisense agent, its mode of administration, and the like. Alternatively, in some embodiments, the amount of an SARM1 antisense agent included in and/or delivered by administration of a pharmaceutical composition or regimen as described herein may be standardized across a relevant patient population (e.g., all patients, all patients of a particular age or stage of disease or expressing a particular biomarker, etc.).

A provided SARM1 antisense agent or composition of the present disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided SARM1 antisense agent or composition of the present disclosure will be decided by the attending physician within the scope of sound medical judgment. The specific effective dose level for any particular patient or organism will depend upon a variety of factors including the disorder being treated and the severity of the disorder; the clinical condition of the individual patient; the cause of the disorder; the activity of the specific SARM1 antisense agent employed; the specific composition employed; the age, body weight, general health, sex and diet of the patient; the time of administration, delivery site of the agent, route of administration, and rate of degradation of the specific SARM1 antisense agent employed; the duration of the treatment; drugs used in combination or coincidental with the specific SARM1 antisense agent employed, and like factors well known in the medical arts. In some embodiments, the effective amount of the SARM1 antisense agent to be administered will be governed by such considerations, and is the minimum amount necessary to inhibit SARM1 activity, inflammatory activity, necroptosis or immune activity as required to prevent or treat the undesired disease or disorder, such as for example, neurodegeneration or traumatic neural injury.

In some embodiments, compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intradermal, intraocular, intravitreal, intralesional and intracranial injection or infusion techniques. Preferably, the compositions are administered via intrathecal, intraventricular, intracerebroventricular, intracisternal, intraparenchymal or intravitreal injection.

In some embodiments, pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

The daily dose is, in certain embodiments, given as a single daily dose or in divided doses two to six times a day, or in sustained release form. This dosage regimen may be adjusted to provide the optimal therapeutic response. In some embodiments, compositions of the present disclosure can be delivered four times a week, three times a week, twice a week, once a week, every ten days, every two weeks, every three weeks, or more preferably every four weeks, once a month, every six weeks, every eight weeks, every other month, every three months, every four months, every six months, every eight months, every nine months or annually.

Compositions of the present disclosure may be administered in combination with other therapeutic agents. Those additional agents may be administered separately from a provided SARM1 antisense agent or composition thereof, as part of a multiple dosage regimen. Alternatively, those agents may be part of a single dosage form, mixed together with a provided SARM1 antisense agent in a single composition. If administered as part of a multiple dosage regime, the two active agents may be submitted simultaneously, sequentially or within a period of time from one another, normally within five hours from one another.

It should also be understood that a specific dosage and treatment regimen for any particular patient may depend upon a variety of factors, including the activity of the specific SARM1 antisense agent employed, the age, body weight, general health, sex, diet, time of administration, rate of excretion, drug combination, and the judgment of the treating physician and the severity of the particular disease being treated. In some embodiments, the amount of an SARM1 antisense agent of the present disclosure in the composition will also depend upon the particular SARM1 antisense agent in the composition.

In some embodiments, SARM1 antisense agents as described herein may be utilized in combination with one or more other therapies to treat a relevant disease, disorder, or condition. In some embodiments, dosing of an SARM1 antisense agent is altered when utilized in combination therapy as compared with when administered as monotherapy; alternatively or additionally, in some embodiments, a therapy that is administered in combination with an SARM1 antisense agent as described herein is administered according to a regimen or protocol that differs from its regimen or protocol when administered alone or in combination with one or more therapies other than an SARM1 antisense agent of the present disclosure. In some embodiments, compositions which comprise an additional therapeutic agent, that additional therapeutic agent and a provided SARM1 antisense agent may act synergistically. In some embodiments, one or both therapies utilized in a combination regimen are administered at a lower level or less frequently than when they are utilized individually as monotherapies.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder or condition and b) a combination comprising a SARM1 antisense oligonucleotide and a SARM1 inhibitor. In some embodiments, the present disclosure provides a combination therapy comprising a SARM1 antisense oligonucleotide and a SARM1 inhibitor; and ii) administering said combination to said subject under conditions such that said neurodegenerative disease, disorder or condition is reduced. In some embodiments, a SARM1 antisense oligonucleotide and a SARM1 inhibitor act synergistically in treating, preventing, and/or ameliorating a neurodegenerative disease, disorder or condition. In some embodiments, a SARM1 inhibitor is a small molecule.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder or condition and b) a combination comprising a SARM1 antisense oligonucleotide and NAD+ or a NAD+ precursor (e.g., NR, NRH, NA, NaR, NAM, NMN, NaMN, TRP, vitamin $B_3$, or NAAD); and ii) administering said combination to said subject under conditions such that said neurodegenerative disease, disorder or condition is reduced. In some embodiments, the present disclosure provides a combination therapy comprising a SARM1 antisense oligonucleotide and NAD+ or a NAD+ precursor (e.g., NR, NRH, NA, NaR, NAM, NMN, NaMN, TRP, vitamin B3, or NAAD). In some embodiments, a SARM1 antisense oligonucleotide and NAD+ or a NAD+ precursor (e.g., NR, NRH, NA, NaR, NAM, NMN, NaMN, TRP, vitamin $B_3$, or NAAD) act synergistically in treating, preventing, and/or ameliorating a neurodegenerative disease, disorder or condition.

In some embodiments, the present disclosure relates to a method of treating, preventing, and/or ameliorating a neurodegenerative disease, disorder or condition comprising i) providing a) a subject diagnosed with, at risk for, or exhibiting symptoms of, a neurodegenerative disease, disorder or condition and b) a combination comprising a SARM1 antisense oligonucleotide and any biologic agent known in the art (e.g., but not limited to, an antibody, aptamer, trophic factor, or antisense oligonucleotide against a target other than SARM1); and ii) administering said combination to said subject under conditions such that said neurodegenerative disease, disorder or condition is reduced.

In some embodiments, an SARM1 antisense agent and/or compositions comprising a SARM1 agent described herein are administered with a chemotherapeutic agent including, but not limited to, alkylating agents, anthracyclines, taxanes, epothilones, histone deacetylase inhibitors, topoisomerase inhibitors, kinase inhibitors, nucleotide analogs, peptide antibiotics, platinum-based agents, retinoids, vinca alkaloids and derivatives. In some embodiments, an SARM1 antisense agent and/or compositions described herein are administered in combination with PARP inhibitors.

Pharmaceutical Compositions

In some embodiments, the present invention provides pharmaceutical compositions comprising one or more antisense agents. In some embodiments, pharmaceutical compositions comprise a suitable pharmaceutically acceptable diluent or carrier. In some embodiments, pharmaceutical compositions comprise a sterile saline solution and one or more antisense agents. In some embodiments, pharmaceutical compositions consist of a sterile saline solution and one or more antisense agents. In some embodiments, a sterile saline is pharmaceutical grade saline. In some embodiments, pharmaceutical compositions comprise sterile water and one or more antisense agents. In some embodiments, pharmaceutical compositions consist of sterile water and one or more antisense agents. In some embodiments, a sterile saline is pharmaceutical grade water. In some embodiments, pharmaceutical compositions comprise phosphate-buffered saline (PBS) and one or more antisense agents. In some embodiments, pharmaceutical compositions consist of sterile phosphate-buffered saline (PBS) and one or more antisense agents. In some embodiments, a sterile saline is pharmaceutical grade PBS.

In some embodiments, antisense agents may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense agents as disclosed herein encompass any pharmaceutically acceptable salts, esters, or salts of such esters. In some embodiments, pharmaceutical compositions comprising antisense agents comprise one or more oligonucleotides which, upon administration to an animal, including a human, is capable of providing (directly or indirectly) the biologically active metabolite or residue thereof. Accordingly, for example, the disclosure is also drawn to pharmaceutically acceptable salts of antisense agents, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric agent.

Lipid moieties have been used in nucleic acid therapies in a variety of methods. In certain such methods, a nucleic acid is introduced into preformed liposomes or lipoplexes made of mixtures of cationic lipids and neutral lipids. In some methods, DNA complexes with mono- or poly-cationic lipids are formed without the presence of a neutral lipid. In some embodiments, a lipid moiety is selected to increase distribution of a pharmaceutical agent to a particular cell or tissue. In some embodiments, a lipid moiety is selected to increase distribution of a pharmaceutical agent to CNS tissue. In some embodiments, a lipid moiety is selected to increase distribution of a pharmaceutical agent to PNS tissue.

In some embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In some embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In some embodiments, certain organic solvents such as dimethylsulfoxide are used.

In some embodiments, a pharmaceutical composition provided herein comprises one or more tissue-specific delivery molecules designed to deliver the one or more pharmaceutical agents of the present invention to specific tissues or cell types. For example, in some embodiments, pharmaceutical compositions include liposomes coated with a tissue-specific antibody.

In some embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In some embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some embodiments, a pharmaceutical composition provided herein is prepared for oral administration. In some embodiments, pharmaceutical compositions are prepared for buccal administration. In some embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In some embodiments, other ingredients are included (e.g., ingredients that aid in solubility or serve as preservatives). In some embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions. In some embodiments, a pharmaceutical composition is prepared for transmucosal administration. In certain of such embodiments penetrants appropriate to the barrier to be permeated are used in the formulation. Such penetrants are generally known in the art.

In some embodiments, a pharmaceutical composition provided herein comprises an oligonucleotide in a therapeutically effective amount. In some embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In some embodiments, one or more modified oligonucleotides provided herein are formulated as a prodrug. In some embodiments, upon in vivo administration, a prodrug is chemically converted to a biologically, pharmaceutically or therapeutically more active form of an oligonucleotide. In some embodiments, prodrugs are useful because they are easier to administer than the corresponding active form. For example, in certain instances, a prodrug may be more bioavailable (e.g., through oral administration) than is the corresponding active form. In some instances, a prodrug may have improved solubility compared to the corresponding active form. In some embodiments, prodrugs are less water soluble than the corresponding active form. In some instances, such prodrugs possess superior transmittal across cell membranes, where water solubility is detrimental to mobility. In some embodiments, a prodrug is an ester. In certain such embodiments, the ester is metabolically hydrolyzed to carboxylic acid upon administration. In certain instances, the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In some embodiments, the present invention provides compositions and methods for reducing the amount or activity of a target nucleic acid in a cell. In some embodiments, the cell is in an animal. In some embodiments, an animal is a mammal. In some embodiments, an animal is a rodent. In some embodiments, an animal is a primate. In some embodiments, an animal is a non-human primate. In some embodiments, an animal is a human.

In some embodiments, the present invention provides methods of administering a pharmaceutical composition comprising an oligomeric agent of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, intracisternal and parenteral (e.g., intravenous, intramuscular, intramedullary, and subcutaneous). In some embodiments, pharmaceutical intrathecals are administered to achieve local rather than systemic exposures. For example, pharmaceutical compositions may be injected directly in the area of desired effect (e.g., into the eyes, ears).

In some embodiments, a pharmaceutical composition is administered to an animal having at least one symptom associated with a neurodegenerative disease or disorder. In some embodiments, such administration results in amelioration of at least one symptom. In some embodiments, administration of a pharmaceutical composition to an animal results in a decrease of SARM1 mRNA in a cell of the animal. In some embodiments, such administration results in a decrease in SARM1 protein.

Exemplary Embodiments

1. An antisense oligonucleotide comprising a sequence having at least 80% identity to a sequence selected from a group consisting of SEQ ID NO: 3-26.
2. The antisense oligonucleotide of embodiment 1, comprising a sequence having at least 85% identity to a sequence selected from a group consisting of SEQ ID NO: 3-26.
3. The antisense oligonucleotide of embodiment 1 or embodiment 2, comprising a sequence having at least 90% identity to a sequence selected from a group consisting of SEQ ID NO: 3-26.
4. The antisense oligonucleotide of any one of embodiments 1-3, comprising a sequence selected from a group consisting of SEQ ID NO: 3-26.
5. An antisense oligonucleotide comprising a sequence selected from a group consisting of SEQ ID NO: 3-2081.
6. The antisense oligonucleotide of any one of embodiments 1-5, wherein the antisense oligonucleotide comprises one or more modifications.
7. The antisense oligonucleotide of embodiment 6, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.
8. A pharmaceutical composition comprising an antisense oligonucleotide of any one of the previous embodiments.
9. The pharmaceutical composition of embodiment 8, wherein the pharmaceutical composition comprises a pharmaceutically acceptable carrier.
10. A method for treating and/or preventing axonal degeneration in a subject, comprising: administering to the subject an antisense oligonucleotide is complementary to a target region of a nucleic acid encoding Sterile Alpha and TIR motif-containing 1 (SARM1).
11. A method comprising administering to a subject at risk of developing a neurodegenerative disease or disorder an antisense oligonucleotide that is complementary to a target region of a nucleic acid encoding SARM1.
12. The method of embodiment 10 or embodiment 11, wherein the target nucleic acid encoding SARM1 is a SARM1 mRNA.
13. The method of any one of embodiments 10-12, wherein the antisense oligonucleotide comprises a sequence having at least 80% identity to a sequence selected from a group consisting of SEQ ID NO: 3-26.

14. The method of any one of embodiments 10-13, wherein the antisense oligonucleotide comprises a sequence having at least 85% identity to a sequence selected from a group consisting of SEQ ID NO: 3-26.

15. The method of any one of embodiments 10-14, wherein the antisense oligonucleotide comprises a sequence having at least 90% identity to a sequence selected from a group consisting of SEQ ID NO: 3-26.

16. The method of any one of embodiments 10-15, wherein the antisense oligonucleotide comprises a sequence selected from a group consisting of SEQ ID NO: 3-26.

17. The method of any one of embodiments 10-12, wherein the antisense oligonucleotide comprises a sequence selected from a group consisting of SEQ ID NO: 3-2081.

18. The method of any one of embodiments 10-17, wherein the antisense oligonucleotide comprises one or more modifications.

19. The method of embodiment 18, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

20. The method of any one of embodiments 10-19, wherein administering the antisense oligonucleotide decreases levels of SARM1 mRNA in the subject.

21. The method of any one of embodiments 10-19, wherein administering the antisense oligonucleotide decreases levels of SARM1 protein in the subject.

22. The method of any one of embodiments 11-21, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

23. The method of any of embodiments 11-21, wherein the neurodegenerative disease or disorder comprises a chronic disease or disorder of the PNS.

24. The method of embodiment 23, wherein the chronic disease or disorder of the PNS comprises a systemic disorder, a pain disorder, or a metabolic disease or disorder.

25. The method of embodiment 23, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

26. The method of embodiment 24, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

27. The method of embodiment 24, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

28. The method of embodiment 24, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

29. The method of any one of embodiments 11-22, the neurodegenerative disease or disorder comprises an acute disease or disorder of the peripheral nervous system.

30. The method of embodiment 29, wherein the acute disease or disorder of the PNS is the result of a mechanical injury, thermal injury, or injury from a chemical agent or chemotherapy.

31. The method of embodiment 30, wherein the mechanical injury comprises a compression or entrapment injury or a pressure injury.

32. The method of embodiment 31, wherein the compression or entrapment injury comprises carpal tunnel syndrome, direct trauma, a penetrating injury, a contusion, a fracture or a dislocated bone.

33. The method of embodiment 31, wherein the pressure injury comprises pressure involving superficial nerves, pressure from a tumor or increased intraocular pressure.

34. The method of embodiment 30, wherein the chemical agent or chemotherapy comprises a cytotoxic anticancer agent, thalidomide, an epothilone, a taxane, a vinca alkaloid, a proteasome inhibitor, a platinum-based drug or an auristatin.

35. The method of embodiment 34, wherein the epothilone is ixabepilone.

36. The method of embodiment 34, wherein the taxane is paclitaxel or docetaxel.

37. The method of embodiment 34, wherein the vinca alkaloid is vinblastine, vinorelbine, vincristine, or vindesine.

38. The method of embodiment 34, wherein the proteasome inhibitor is bortezomib.

39. The method of embodiment 34, wherein the platinum-based drug is cisplatin, oxaliplatin, or carboplatin.

40. The method of embodiment 34, wherein the auristatin is conjugated monomethyl auristatin E.

41. The method of any one of embodiments 11-22, wherein the neurodegenerative disease or disorder comprises a chronic disease or disorder of the CNS.

42. The method of embodiment 41, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornz-weig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

43. The method of embodiment 41, wherein the chronic disease or disorder of the CNS comprises an optic nerve disorder, a traumatic CNS injury, or a metabolic disease or disorder.

44. The method of embodiment 43, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

45. The method of embodiment 43, wherein the traumatic CNS injury comprises a traumatic brain injury (TBI), a spinal cord injury, traumatic axonal injury or chronic traumatic encephalopathy (CTE).

46. The method of embodiment 43, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

47. The method of any one of embodiments 11-22, wherein the neurodegenerative disease or disorder comprises an acute disease or disorder of the CNS.

48. The method of embodiment 47, wherein the acute disease or disorder of the CNS comprises an ischemia, a traumatic CNS injury, injury from a chemical agent, thermal injury, or viral encephalitis.

49. The method of embodiment 48, wherein the ischemia comprises cerebral ischemia, hypoxic demyelination, ischemic demyelination, ischemic optic neuropathy, or non-arteritic anterior ischemic optic neuropathy.

50. The method of embodiment 48, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

51. The method of embodiment 48, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

52. The method of any one of embodiments 11-22, wherein the neurodegenerative disease or disorder results from blood clotting issues, inflammation, obesity, aging, stress, cancer, or diabetes.

53. The method of any one of embodiments 10-52, wherein the subject is a human.

54. The method of any one of embodiments 10-53, wherein the subject is a patient with one or more risk factors for developing a condition involving axonal degeneration.

55. The method of embodiments 54, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

56. The method of embodiment 55, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

57. The method of embodiment 55, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

58. The method of embodiment 55, wherein the one or more biomarkers of neurodegeneration comprises:
concentration of neurofilament light chain protein (NF-L) in one or more of: a cerebrospinal fluid (CSF) sample, a blood sample, and a plasma sample from the subject;
concentration of neurofilament heavy chain protein (NF-H) in one or more of: a cerebrospinal fluid (CSF) sample, a blood sample, and a plasma sample from the subject;
concentration of Ubiquitin C-terminal Hydrolase L1 (UCH-L1) in one or more of: a cerebrospinal fluid (CSF) sample, a blood sample, and a plasma sample from the subject;
concentration of alpha-synuclein in one or more of: a cerebrospinal fluid (CSF) sample, a blood sample, and a plasma sample from the subject;
constitutive NAD+ levels in neurons and/or axons of the subject;
constitutive cADPR levels in neurons and/or axons of the subject;
levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid biopsy sample from the subject; and
levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

59. An antisense oligonucleotide comprising a sequence having at least 80% identity to a sequence selected from a group consisting of SEQ ID NO: 3-21, 23-26, 38 and 39.

60. The antisense oligonucleotide of embodiment 59, comprising a sequence having at least 85% identity to a sequence selected from a group consisting of SEQ ID NO: 3-21, 23-26, 38 and 39.

61. The antisense oligonucleotide of embodiment 59 or embodiment 60, comprising a sequence having at least 90% identity to a sequence selected from a group consisting of SEQ ID NO: 3-21, 23-26, 38 and 39.

62. The antisense oligonucleotide of any one of embodiments 59-61, comprising a sequence selected from a group consisting of SEQ ID NO: 3-21, 23-26, 38 and 39.

63. An antisense oligonucleotide comprising a sequence having at least 80% identity to a sequence selected from a group consisting of SEQ ID NO: 8, 9, 13, 22, 38, and 549.

64. The antisense oligonucleotide of embodiment 63, comprising a sequence having at least 85% identity to a sequence selected from a group consisting of 8, 9, 13, 22, 38, and 549.

65. The antisense oligonucleotide of embodiment 63 or embodiment 64, comprising a sequence having at least 90% identity to a sequence selected from a group consisting of 8, 9, 13, 22, 38, and 549.

66. The antisense oligonucleotide of any one of embodiments 63-65, comprising a sequence selected from a group consisting of SEQ ID NO: 8, 9, 13, 22, 38, and 549.

67. An antisense oligonucleotide comprising a sequence selected from a group consisting of SEQ ID NO: 3-2412.

68. The antisense oligonucleotide of any one of embodiments 59-66, wherein the antisense oligonucleotide comprises one or more modifications.

69. The antisense oligonucleotide of embodiment 68, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

70. A pharmaceutical composition comprising an antisense oligonucleotide of any one of the previous embodiments.

71. A pharmaceutical composition comprising an antisense oligonucleotide of any one of embodiments 59-70.

72. The pharmaceutical composition of embodiment 70 or 71, wherein the pharmaceutical composition comprises a pharmaceutically acceptable carrier.

73. A method for treating and/or preventing axonal degeneration in a subject, comprising: administering to the subject an antisense oligonucleotide that is complementary to a target region of a nucleic acid encoding Sterile Alpha and TIR motif-containing 1 (SARM1).

74. A method comprising administering to a subject at risk of developing a neurodegenerative disease or disorder an antisense oligonucleotide that is complementary to a target region of a nucleic acid encoding SARM1.

75. The method of embodiment 73 or embodiment 74, wherein the target nucleic acid encoding SARM1 is a SARM1 mRNA.

76. The method of any one of embodiments 73-75, wherein the antisense oligonucleotide comprises a sequence having at least 80% identity to a sequence selected from a group consisting of SEQ ID NO: 3-21, 23-26, 38 and 39.

77. The method of any one of embodiments 73-76, wherein the antisense oligonucleotide comprises a sequence having at least 85% identity to a sequence selected from a group consisting of SEQ ID NO: 3-21, 23-26, 38 and 39.

78. The method of any one of embodiments 73-77, wherein the antisense oligonucleotide comprises a sequence having at least 90% identity to a sequence selected from a group consisting of SEQ ID NO: 3-21, 23-26, 38 and 39.

79. The method of any one of embodiments 73-78, wherein the antisense oligonucleotide comprises a sequence selected from a group consisting of SEQ ID NO: 3-21, 23-26, 38 and 39.

80. The method of any one of embodiments 73-75, wherein the antisense oligonucleotide comprises a sequence having at least 80% identity to a sequence selected from a group consisting of SEQ ID NO: 8, 9, 13, 22, 38, and 549.

81. The method of any one of embodiments 73-75, and 80, wherein the antisense oligonucleotide comprises a sequence having at least 85% identity to a sequence selected from a group consisting of SEQ ID NO: 8, 9, 13, 22, 38, and 549.

82. The method of any one of embodiments 73-75, and 80-81, wherein the antisense oligonucleotide comprises a sequence having at least 90% identity to a sequence selected from a group consisting of SEQ ID NO: 8, 9, 13, 22, 38, and 549.

83. The method of any one of embodiments 73-75, and 80-82, wherein the antisense oligonucleotide comprises a sequence selected from a group consisting of SEQ ID NO: 8, 9, 13, 22, 38, and 549.

84. The method of any one of embodiments 73-75, wherein the antisense oligonucleotide comprises a sequence selected from a group consisting of SEQ ID NO: 3-2412.

85. The method of any one of embodiments 73-84, wherein the antisense oligonucleotide comprises one or more modifications.

86. The method of embodiment 85, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

87. The method of any one of embodiments 73-86, wherein administering the antisense oligonucleotide decreases levels of SARM1 mRNA in the subject.

88. The method of any one of embodiments 73-86, wherein administering the antisense oligonucleotide decreases levels of SARM1 protein in the subject.

89. The method of any one of embodiments 74-88, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

90. The method of any of embodiments 74-88, wherein the neurodegenerative disease or disorder comprises a chronic disease or disorder of the PNS.

91. The method of embodiment 90, wherein the chronic disease or disorder of the PNS comprises a systemic disorder, a pain disorder, or a metabolic disease or disorder.

92. The method of embodiment 90, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

93. The method of embodiment 91, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

94. The method of embodiment 91, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

95. The method of embodiment 91, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

96. The method of any one of embodiments 74-89, the neurodegenerative disease or disorder comprises an acute disease or disorder of the peripheral nervous system.

97. The method of embodiment 96, wherein the acute disease or disorder of the PNS is the result of a mechanical injury, thermal injury, or injury from a chemical agent or chemotherapy.

98. The method of embodiment 97, wherein the mechanical injury comprises a compression or entrapment injury or a pressure injury.

99. The method of embodiment 98, wherein the compression or entrapment injury comprises carpal tunnel syndrome, direct trauma, a penetrating injury, a contusion, a fracture or a dislocated bone.

100. The method of embodiment 98, wherein the pressure injury comprises pressure involving superficial nerves, pressure from a tumor or increased intraocular pressure.

101. The method of embodiment 97, wherein the chemical agent or chemotherapy comprises a cytotoxic anti-cancer agent, thalidomide, an epothilone, a taxane, a vinca alkaloid, a proteasome inhibitor, a platinum-based drug or an auristatin.

102. The method of embodiment 101, wherein the epothilone is ixabepilone.

103. The method of embodiment 101, wherein the taxane is paclitaxel or docetaxel.

104. The method of embodiment 101, wherein the vinca alkaloid is vinblastine, vinorelbine, vincristine, or vindesine.

105. The method of embodiment 101, wherein the proteasome inhibitor is bortezomib.

106. The method of embodiment 101, wherein the platinum-based drug is cisplatin, oxaliplatin, or carboplatin.

107. The method of embodiment 101, wherein the auristatin is conjugated monomethyl auristatin E.

108. The method of any one of embodiments 74-89, wherein the neurodegenerative disease or disorder comprises a chronic disease or disorder of the CNS.

109. The method of embodiment 108, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

110. The method of embodiment 108, wherein the chronic disease or disorder of the CNS comprises an optic nerve disorder, a traumatic CNS injury, or a metabolic disease or disorder.

111. The method of embodiment 110, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

112. The method of embodiment 110, wherein the traumatic CNS injury comprises a traumatic brain injury (TBI), a spinal cord injury, traumatic axonal injury or chronic traumatic encephalopathy (CTE).

113. The method of embodiment 110, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

114. The method of any one of embodiments 74-89, wherein the neurodegenerative disease or disorder comprises an acute disease or disorder of the CNS.

115. The method of embodiment 114, wherein the acute disease or disorder of the CNS comprises an ischemia, a traumatic CNS injury, injury from a chemical agent, thermal injury, or viral encephalitis.

116. The method of embodiment 115, wherein the ischemia comprises cerebral ischemia, hypoxic demyelination, ischemic demyelination, ischemic optic neuropathy, or non-arteritic anterior ischemic optic neuropathy.

117. The method of embodiment 115, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

118. The method of embodiment 115, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

119. The method of any one of embodiments 74-89, wherein the neurodegenerative disease or disorder results from blood clotting issues, inflammation, obesity, aging, stress, cancer, or diabetes.

120. The method of any one of embodiments 73-119, wherein the subject is a human.

121. The method of any one of embodiments 73-120, wherein the subject is a patient with one or more risk factors for developing a condition involving axonal degeneration.

122. The method of embodiment 121, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

123. The method of embodiment 122, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

124. The method of embodiment 122, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

125. The method of embodiment 122, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

126. An antisense oligonucleotide selected from Table 3, for use in the manufacture of a medicament.

127. An antisense oligonucleotide selected from Table 3, for use in treatment of a disease, disorder or injury.

128. The antisense oligonucleotide of embodiment 127, wherein the disease, disorder or injury comprises inherited neuropathies, Charcot-Marie-Tooth disease, hereditary sensory and autonomic neuropathy (HSAN), chronic inflammatory demyelinating polyneuropathy (CIDP), idiopathic neuropathies, other peripheral neuropathies, diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, polyarteritis nodosa, chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, diabetes, diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, a mitochondrial disorder, carpal tunnel syndrome, direct trauma, a penetrating injury, a contusion, a fracture, a dislocated bone, pressure involving superficial nerves, pressure from a tumor, increased intraocular pressure, injury from a chemical agent or chemo-therapy, Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leuko-encephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, spinal cord injury, an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, exposure to cyanide, a traumatic brain injury (TBI), a spinal cord injury, traumatic axonal injury, chronic traumatic encephalopathy (CTE), diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, mitochondrial disorders, cerebral ischemia, hypoxic demyelination, ischemic demyelination, ischemic optic neuropathy, or non-arteritic anterior ischemic optic neuropathy, a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, damage from a force which causes axons to deform, stretch, crush or sheer, enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

129. An antisense oligonucleotide comprising a sequence having at least 80% identity to SEQ ID NO: 8.

130. The antisense oligonucleotide of embodiment 129, comprising a sequence having at least 85% identity to SEQ ID NO: 8.

131. The antisense oligonucleotide of embodiment 129 or embodiment 130, comprising a sequence having at least 90% identity to SEQ ID NO: 8.

132. The antisense oligonucleotide of any one of embodiments 129-131, comprising SEQ ID NO: 8.

133. The antisense oligonucleotide of any one of embodiments 129-132, wherein the antisense oligonucleotide comprises one or more modifications.

134. The antisense oligonucleotide of embodiment 133, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

135. A pharmaceutical composition comprising an antisense oligonucleotide of any one of embodiments 129-134.

136. The pharmaceutical composition of embodiment 135, wherein the pharmaceutical composition comprises a pharmaceutically acceptable carrier.

137. An antisense oligonucleotide comprising a sequence having at least 80% identity to SEQ ID NO: 9.

138. The antisense oligonucleotide of embodiment 137, comprising a sequence having at least 85% identity to SEQ ID NO: 9.

139. The antisense oligonucleotide of embodiment 137 or embodiment 138, comprising a sequence having at least 90% identity to SEQ ID NO: 9.

140. The antisense oligonucleotide of any one of embodiments 137-139, comprising SEQ ID NO: 9.

141. The antisense oligonucleotide of any one of embodiments 137-140, wherein the antisense oligonucleotide comprises one or more modifications.

142. The antisense oligonucleotide of embodiment 141, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

143. A pharmaceutical composition comprising an antisense oligonucleotide of any one of embodiments 137-142.

144. The pharmaceutical composition of embodiment 143, wherein the pharmaceutical composition comprises a pharmaceutically acceptable carrier.

145. An antisense oligonucleotide comprising a sequence having at least 80% identity to SEQ ID NO: 13.

146. The antisense oligonucleotide of embodiment 145, comprising a sequence having at least 85% identity to SEQ ID NO: 13.

147. The antisense oligonucleotide of embodiment 145 or embodiment 146, comprising a sequence having at least 90% identity to SEQ ID NO: 13.

148. The antisense oligonucleotide of any one of embodiments 145-147, comprising SEQ ID NO: 13.

149. The antisense oligonucleotide of any one of embodiments 145-148, wherein the antisense oligonucleotide comprises one or more modifications.

150. The antisense oligonucleotide of embodiment 149, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

151. A pharmaceutical composition comprising an antisense oligonucleotide of any one of embodiments 145-150.

152. The pharmaceutical composition of embodiment 151, wherein the pharmaceutical composition comprises a pharmaceutically acceptable carrier.

153. An antisense oligonucleotide comprising a sequence having at least 80% identity to SEQ ID NO: 22.

154. The antisense oligonucleotide of embodiment 153, comprising a sequence having at least 85% identity to SEQ ID NO: 22.

155. The antisense oligonucleotide of embodiment 153 or embodiment 154, comprising a sequence having at least 90% identity to SEQ ID NO: 22.

156. The antisense oligonucleotide of any one of embodiments 153-155, comprising SEQ ID NO: 22.

157. The antisense oligonucleotide of any one of embodiments 153-156, wherein the antisense oligonucleotide comprises one or more modifications.

158. The antisense oligonucleotide of embodiment 157, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

159. A pharmaceutical composition comprising an antisense oligonucleotide of any one of embodiments 153-158.

160. The pharmaceutical composition of embodiment 159, wherein the pharmaceutical composition comprises a pharmaceutically acceptable carrier.

161. An antisense oligonucleotide comprising a sequence having at least 80% identity to SEQ ID NO: 38.

162. The antisense oligonucleotide of embodiment 161, comprising a sequence having at least 85% identity to SEQ ID NO: 38.

163. The antisense oligonucleotide of embodiment 161 or embodiment 162, comprising a sequence having at least 90% identity to SEQ ID NO: 38.

164. The antisense oligonucleotide of any one of embodiments 161-163, comprising SEQ ID NO: 38.

165. The antisense oligonucleotide of any one of embodiments 161-164, wherein the antisense oligonucleotide comprises one or more modifications.

166. The antisense oligonucleotide of embodiment 165, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

167. A pharmaceutical composition comprising an antisense oligonucleotide of any one of embodiments 161-166.

168. The pharmaceutical composition of embodiment 167, wherein the pharmaceutical composition comprises a pharmaceutically acceptable carrier.

169. An antisense oligonucleotide comprising a sequence having at least 80% identity to SEQ ID NO: 549.

170. The antisense oligonucleotide of embodiment 169, comprising a sequence having at least 85% identity to SEQ ID NO: 549.

171. The antisense oligonucleotide of embodiment 169 or embodiment 170, comprising a sequence having at least 90% identity to SEQ ID NO: 549.

172. The antisense oligonucleotide of any one of embodiments 169-171, comprising SEQ ID NO: 549.

173. The antisense oligonucleotide of any one of embodiments 169-172, wherein the antisense oligonucleotide comprises one or more modifications.

174. The antisense oligonucleotide of embodiment 173, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

175. A pharmaceutical composition comprising an antisense oligonucleotide of any one of embodiments 169-174.

176. The pharmaceutical composition of embodiment 175, wherein the pharmaceutical composition comprises a pharmaceutically acceptable carrier.

177. A method for treating and/or preventing axonal degeneration in a subject, comprising: administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 8.

178. The method of embodiment 177, wherein the antisense oligonucleotide comprises a sequence having at least 85% identity to SEQ ID NO: 8.

179. The method of embodiment 177 or embodiment 178, wherein the antisense oligonucleotide comprises a sequence having at least 90% identity to SEQ ID NO: 8.

180. The method of any one of embodiments 177-179, wherein the antisense oligonucleotide comprises SEQ ID NO: 8.

181. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 8.

182. The method of embodiment 181, wherein the antisense oligonucleotide comprises a sequence having at least 85% identity to SEQ ID NO: 8.

183. The method of embodiment 181 or embodiment 182, wherein the antisense oligonucleotide comprises a sequence having at least 90% identity to SEQ ID NO: 8.

184. The method of any one of embodiments 181-183, wherein the antisense oligonucleotide comprises SEQ ID NO: 8.

185. The method of any one of embodiments 177-184, wherein the target nucleic acid encoding SARM1 is a SARM1 mRNA.

186. The method of any one of embodiments 177-185, wherein the antisense oligonucleotide comprises one or more modifications.

187. The method of embodiment 186, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

188. The method of any one of embodiments 177-187, wherein administering the antisense oligonucleotide decreases levels of SARM1 mRNA in the subject.

189. The method of any one of embodiments 177-187, wherein administering the antisense oligonucleotide decreases levels of SARM1 protein in the subject.

190. The method of any one of embodiments 181-189, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

191. The method of any of embodiments 181-189, wherein the neurodegenerative disease or disorder comprises a chronic disease or disorder of the PNS.

192. The method of embodiment 191, wherein the chronic disease or disorder of the PNS comprises a systemic disorder, a pain disorder, or a metabolic disease or disorder.

193. The method of embodiment 191, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

194. The method of embodiment 192, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

195. The method of embodiment 192, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

196. The method of embodiment 192, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/ glycolipid metabolism, a nutritional deficiency, a vitamin deficiency, or a mitochondrial disorder.

197. The method of any one of embodiments 181-190, the neurodegenerative disease or disorder comprises an acute disease or disorder of the peripheral nervous system.

198. The method of embodiment 197, wherein the acute disease or disorder of the PNS is the result of a mechanical injury, thermal injury, or injury from a chemical agent or chemotherapy.

199. The method of embodiment 198, wherein the mechanical injury comprises a compression or entrapment injury or a pressure injury.

200. The method of embodiment 199, wherein the compression or entrapment injury comprises carpal tunnel syndrome, direct trauma, a penetrating injury, a contusion, a fracture or a dislocated bone.

201. The method of embodiment 199, wherein the pressure injury comprises pressure involving superficial nerves, pressure from a tumor or increased intraocular pressure.

202. The method of embodiment 198, wherein the chemical agent or chemotherapy comprises a cytotoxic anticancer agent, thalidomide, an epothilone, a taxane, a vinca alkaloid, a proteasome inhibitor, a platinum-based drug or an auristatin.

203. The method of embodiment 202, wherein the epothilone is ixabepilone.

204. The method of embodiment 202, wherein the taxane is paclitaxel or docetaxel.

205. The method of embodiment 202, wherein the vinca alkaloid is vinblastine, vinorelbine, vincristine, or vindesine.

206. The method of embodiment 202, wherein the proteasome inhibitor is bortezomib.

207. The method of embodiment 202, wherein the platinum-based drug is cisplatin, oxaliplatin, or carboplatin.

208. The method of embodiment 202, wherein the auristatin is conjugated monomethyl auristatin E.

209. The method of any one of embodiments 181-190, wherein the neurodegenerative disease or disorder comprises a chronic disease or disorder of the CNS.

210. The method of embodiment 209, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

211. The method of embodiment 209, wherein the chronic disease or disorder of the CNS comprises an optic nerve disorder, a traumatic CNS injury, or a metabolic disease or disorder.

212. The method of embodiment 211, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

213. The method of embodiment 211, wherein the traumatic CNS injury comprises a traumatic brain injury (TBI), a spinal cord injury, traumatic axonal injury or chronic traumatic encephalopathy (CTE).

214. The method of embodiment 211, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

215. The method of any one of embodiments 181-190, wherein the neurodegenerative disease or disorder comprises an acute disease or disorder of the CNS.

216. The method of embodiment 215, wherein the acute disease or disorder of the CNS comprises an ischemia, a traumatic CNS injury, injury from a chemical agent, thermal injury, or viral encephalitis.

217. The method of embodiment 216, wherein the ischemia comprises cerebral ischemia, hypoxic demyelination, ischemic demyelination, ischemic optic neuropathy, or non-arteritic anterior ischemic optic neuropathy.

218. The method of embodiment 216, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

219. The method of embodiment 216, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

220. The method of any one of embodiments 181-190, wherein the neurodegenerative disease or disorder results from blood clotting issues, inflammation, obesity, aging, stress, cancer, or diabetes.

221. The method of any one of embodiments 177-220, wherein the subject is a human.

222. The method of any one of embodiments 177-221, wherein the subject is a patient with one or more risk factors for developing a condition involving axonal degeneration.

223. The method of embodiments 222, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

224. The method of embodiment 223, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

225. The method of embodiment 223, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

226. The method of embodiment 223, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

227. A method for treating and/or preventing axonal degeneration in a subject, comprising:

administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 9.

228. The method of embodiment 227, wherein the antisense oligonucleotide comprises a sequence having at least 85% identity to SEQ ID NO: 9.

229. The method of embodiment 227 or embodiment 228, wherein the antisense oligonucleotide comprises a sequence having at least 90% identity to SEQ ID NO: 9.

230. The method of any one of embodiments 227-229, wherein the antisense oligonucleotide comprises SEQ ID NO: 9.

231. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 9.

232. The method of embodiment 231, wherein the antisense oligonucleotide comprises a sequence having at least 85% identity to SEQ ID NO: 9.

233. The method of embodiment 231 or embodiment 232, wherein the antisense oligonucleotide comprises a sequence having at least 90% identity to SEQ ID NO: 9.

234. The method of any one of embodiments 231-233, wherein the antisense oligonucleotide comprises SEQ ID NO: 9.

235. The method of any one of embodiments 227-234, wherein the target nucleic acid encoding SARM1 is a SARM1 mRNA.

236. The method of any one of embodiments 227-235, wherein the antisense oligonucleotide comprises one or more modifications.

237. The method of embodiment 236, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

238. The method of any one of embodiments 227-237, wherein administering the antisense oligonucleotide decreases levels of SARM1 mRNA in the subject.

239. The method of any one of embodiments 227-237, wherein administering the antisense oligonucleotide decreases levels of SARM1 protein in the subject.

240. The method of any one of embodiments 231-239, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

241. The method of any of embodiments 231-239, wherein the neurodegenerative disease or disorder comprises a chronic disease or disorder of the PNS.

242. The method of embodiment 241, wherein the chronic disease or disorder of the PNS comprises a systemic disorder, a pain disorder, or a metabolic disease or disorder.

243. The method of embodiment 241, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

244. The method of embodiment 242, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

245. The method of embodiment 242, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

246. The method of embodiment 242, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

247. The method of any one of embodiments 231-240, the neurodegenerative disease or disorder comprises an acute disease or disorder of the peripheral nervous system.

248. The method of embodiment 247, wherein the acute disease or disorder of the PNS is the result of a mechanical injury, thermal injury, or injury from a chemical agent or chemotherapy.

249. The method of embodiment 248, wherein the mechanical injury comprises a compression or entrapment injury or a pressure injury.

250. The method of embodiment 249, wherein the compression or entrapment injury comprises carpal tunnel syndrome, direct trauma, a penetrating injury, a contusion, a fracture or a dislocated bone.

251. The method of embodiment 249, wherein the pressure injury comprises pressure involving superficial nerves, pressure from a tumor or increased intraocular pressure.

252. The method of embodiment 248, wherein the chemical agent or chemotherapy comprises a cytotoxic anticancer agent, thalidomide, an epothilone, a taxane, a vinca alkaloid, a proteasome inhibitor, a platinum-based drug or an auristatin.

253. The method of embodiment 252, wherein the epothilone is ixabepilone.

254. The method of embodiment 252, wherein the taxane is paclitaxel or docetaxel.

255. The method of embodiment 252, wherein the vinca alkaloid is vinblastine, vinorelbine, vincristine, or vindesine.

256. The method of embodiment 252, wherein the proteasome inhibitor is bortezomib.

257. The method of embodiment 252, wherein the platinum-based drug is cisplatin, oxaliplatin, or carboplatin.

258. The method of embodiment 252, wherein the auristatin is conjugated monomethyl auristatin E.

259. The method of any one of embodiments 231-240, wherein the neurodegenerative disease or disorder comprises a chronic disease or disorder of the CNS.

260. The method of embodiment 259, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

261. The method of embodiment 259, wherein the chronic disease or disorder of the CNS comprises an optic nerve disorder, a traumatic CNS injury, or a metabolic disease or disorder.

262. The method of embodiment 261, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

263. The method of embodiment 261, wherein the traumatic CNS injury comprises a traumatic brain injury (TBI), a spinal cord injury, traumatic axonal injury or chronic traumatic encephalopathy (CTE).

264. The method of embodiment 261, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

265. The method of any one of embodiments 231-240, wherein the neurodegenerative disease or disorder comprises an acute disease or disorder of the CNS.

266. The method of embodiment 215, wherein the acute disease or disorder of the CNS comprises an ischemia, a traumatic CNS injury, injury from a chemical agent, thermal injury, or viral encephalitis.

267. The method of embodiment 266, wherein the ischemia comprises cerebral ischemia, hypoxic demyelination, ischemic demyelination, ischemic optic neuropathy, or non-arteritic anterior ischemic optic neuropathy.

268. The method of embodiment 266, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

269. The method of embodiment 266, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

270. The method of any one of embodiments 231-240, wherein the neurodegenerative disease or disorder results from blood clotting issues, inflammation, obesity, aging, stress, cancer, or diabetes.

271. The method of any one of embodiments 227-270, wherein the subject is a human.

272. The method of any one of embodiments 227-271, wherein the subject is a patient with one or more risk factors for developing a condition involving axonal degeneration.

273. The method of embodiments 272, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

274. The method of embodiment 273, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a 275. The method of embodiment 273, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

276. The method of embodiment 273, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

277. A method for treating and/or preventing axonal degeneration in a subject, comprising: administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 13.

278. The method of embodiment 277, wherein the antisense oligonucleotide comprises a sequence having at least 85% identity to SEQ ID NO: 13.

279. The method of embodiment 277 or embodiment 278, wherein the antisense oligonucleotide comprises a sequence having at least 90% identity to SEQ ID NO: 13.

280. The method of any one of embodiments 277-279, wherein the antisense oligonucleotide comprises SEQ ID NO: 13.

281. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 13.

282. The method of embodiment 281, wherein the antisense oligonucleotide comprises a sequence having at least 85% identity to SEQ ID NO: 13.

283. The method of embodiment 281 or embodiment 282, wherein the antisense oligonucleotide comprises a sequence having at least 90% identity to SEQ ID NO: 13.

284. The method of any one of embodiments 281-283, wherein the antisense oligonucleotide comprises SEQ ID NO: 13.

285. The method of any one of embodiments 277-284, wherein the target nucleic acid encoding SARM1 is a SARM1 mRNA.

286. The method of any one of embodiments 277-285, wherein the antisense oligonucleotide comprises one or more modifications.

287. The method of embodiment 286, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

288. The method of any one of embodiments 277-287, wherein administering the antisense oligonucleotide decreases levels of SARM1 mRNA in the subject.

289. The method of any one of embodiments 277-287, wherein administering the antisense oligonucleotide decreases levels of SARM1 protein in the subject.

290. The method of any one of embodiments 281-289, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

291. The method of any of embodiments 281-289, wherein the neurodegenerative disease or disorder comprises a chronic disease or disorder of the PNS.

292. The method of embodiment 291, wherein the chronic disease or disorder of the PNS comprises a systemic disorder, a pain disorder, or a metabolic disease or disorder.

293. The method of embodiment 291, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

294. The method of embodiment 292, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

295. The method of embodiment 292, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

296. The method of embodiment 292, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/ glycolipid metabolism, a nutritional deficiency, a vitamin deficiency, or a mitochondrial disorder.

297. The method of any one of embodiments 281-290, the neurodegenerative disease or disorder comprises an acute disease or disorder of the peripheral nervous system.

298. The method of embodiment 297, wherein the acute disease or disorder of the PNS is the result of a mechanical injury, thermal injury, or injury from a chemical agent or chemotherapy.

299. The method of embodiment 298, wherein the mechanical injury comprises a compression or entrapment injury or a pressure injury.

300. The method of embodiment 298, wherein the compression or entrapment injury comprises carpal tunnel syndrome, direct trauma, a penetrating injury, a contusion, a fracture or a dislocated bone.

301. The method of embodiment 298, wherein the pressure injury comprises pressure involving superficial nerves, pressure from a tumor or increased intraocular pressure.

302. The method of embodiment 298, wherein the chemical agent or chemotherapy comprises a cytotoxic anticancer agent, thalidomide, an epothilone, a taxane, a vinca alkaloid, a proteasome inhibitor, a platinum-based drug or an auristatin.

303. The method of embodiment 302, wherein the epothilone is ixabepilone.

304. The method of embodiment 302, wherein the taxane is paclitaxel or docetaxel.

305. The method of embodiment 302, wherein the vinca alkaloid is vinblastine, vinorelbine, vincristine, or vindesine.

306. The method of embodiment 302, wherein the proteasome inhibitor is bortezomib.

307. The method of embodiment 302, wherein the platinum-based drug is cisplatin, oxaliplatin, or carboplatin.

308. The method of embodiment 302, wherein the auristatin is conjugated monomethyl auristatin E.

309. The method of any one of embodiments 281-290, wherein the neurodegenerative disease or disorder comprises a chronic disease or disorder of the CNS.

310. The method of embodiment 309, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

311. The method of embodiment 309, wherein the chronic disease or disorder of the CNS comprises an optic nerve disorder, a traumatic CNS injury, or a metabolic disease or disorder.

312. The method of embodiment 311, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

313. The method of embodiment 311, wherein the traumatic CNS injury comprises a traumatic brain injury (TBI), a spinal cord injury, traumatic axonal injury or chronic traumatic encephalopathy (CTE).

314. The method of embodiment 311, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

315. The method of any one of embodiments 281-290, wherein the neurodegenerative disease or disorder comprises an acute disease or disorder of the CNS.

316. The method of embodiment 315, wherein the acute disease or disorder of the CNS comprises an ischemia, a traumatic CNS injury, injury from a chemical agent, thermal injury, or viral encephalitis.

317. The method of embodiment 316, wherein the ischemia comprises cerebral ischemia, hypoxic demyelination, ischemic demyelination, ischemic optic neuropathy, or non-arteritic anterior ischemic optic neuropathy.

318. The method of embodiment 316, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

319. The method of embodiment 316, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

320. The method of any one of embodiments 281-290, wherein the neurodegenerative disease or disorder results from blood clotting issues, inflammation, obesity, aging, stress, cancer, or diabetes.

321. The method of any one of embodiments 277-320, wherein the subject is a human.

322. The method of any one of embodiments 277-321, wherein the subject is a patient with one or more risk factors for developing a condition involving axonal degeneration.

323. The method of embodiments 322, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

324. The method of embodiment 323, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

325. The method of embodiment 323, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

326. The method of embodiment 323, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

327. A method for treating and/or preventing axonal degeneration in a subject, comprising:

administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 22.

328. The method of embodiment 327, wherein the antisense oligonucleotide comprises a sequence having at least 85% identity to SEQ ID NO: 22.

329. The method of embodiment 327 or embodiment 328, wherein the antisense oligonucleotide comprises a sequence having at least 90% identity to SEQ ID NO: 22.

330. The method of any one of embodiments 327-329, wherein the antisense oligonucleotide comprises SEQ ID NO: 22.

331. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 22.

332. The method of embodiment 331, wherein the antisense oligonucleotide comprises a sequence having at least 85% identity to SEQ ID NO: 22.

333. The method of embodiment 331 or embodiment 332, wherein the antisense oligonucleotide comprises a sequence having at least 90% identity to SEQ ID NO: 22.

334. The method of any one of embodiments 331-333, wherein the antisense oligonucleotide comprises SEQ ID NO: 22.

335. The method of any one of embodiments 327-334, wherein the target nucleic acid encoding SARM1 is a SARM1 mRNA.

336. The method of any one of embodiments 327-335, wherein the antisense oligonucleotide comprises one or more modifications.

337. The method of embodiment 336, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

338. The method of any one of embodiments 327-337, wherein administering the antisense oligonucleotide decreases levels of SARM1 mRNA in the subject.

339. The method of any one of embodiments 327-337, wherein administering the antisense oligonucleotide decreases levels of SARM1 protein in the subject.

340. The method of any one of embodiments 331-339, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

341. The method of any of embodiments 331-339, wherein the neurodegenerative disease or disorder comprises a chronic disease or disorder of the PNS.

342. The method of embodiment 341, wherein the chronic disease or disorder of the PNS comprises a systemic disorder, a pain disorder, or a metabolic disease or disorder.

343. The method of embodiment 341, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

344. The method of embodiment 342, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

345. The method of embodiment 342, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

346. The method of embodiment 342, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/ glycolipid metabolism, a nutritional deficiency, a vitamin deficiency, or a mitochondrial disorder.

347. The method of any one of embodiments 331-340, the neurodegenerative disease or disorder comprises an acute disease or disorder of the peripheral nervous system.

348. The method of embodiment 347, wherein the acute disease or disorder of the PNS is the result of a mechanical injury, thermal injury, or injury from a chemical agent or chemotherapy.

349. The method of embodiment 348, wherein the mechanical injury comprises a compression or entrapment injury or a pressure injury.

350. The method of embodiment 348, wherein the compression or entrapment injury comprises carpal tunnel syndrome, direct trauma, a penetrating injury, a contusion, a fracture or a dislocated bone.

351. The method of embodiment 348, wherein the pressure injury comprises pressure involving superficial nerves, pressure from a tumor or increased intraocular pressure.

352. The method of embodiment 348, wherein the chemical agent or chemotherapy comprises a cytotoxic anti-cancer agent, thalidomide, an epothilone, a taxane, a vinca alkaloid, a proteasome inhibitor, a platinum-based drug or an auristatin.

353. The method of embodiment 352, wherein the epothilone is ixabepilone.

354. The method of embodiment 352, wherein the taxane is paclitaxel or docetaxel.

355. The method of embodiment 352, wherein the vinca alkaloid is vinblastine, vinorelbine, vincristine, or vindesine.

356. The method of embodiment 352, wherein the proteasome inhibitor is bortezomib.

357. The method of embodiment 352, wherein the platinum-based drug is cisplatin, oxaliplatin, or carboplatin.

358. The method of embodiment 352, wherein the auristatin is conjugated monomethyl auristatin E.

359. The method of any one of embodiments 331-340, wherein the neurodegenerative disease or disorder comprises a chronic disease or disorder of the CNS.

360. The method of embodiment 359, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

361. The method of embodiment 359, wherein the chronic disease or disorder of the CNS comprises an optic nerve disorder, a traumatic CNS injury, or a metabolic disease or disorder.

362. The method of embodiment 361, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

363. The method of embodiment 361, wherein the traumatic CNS injury comprises a traumatic brain injury (TBI), a spinal cord injury, traumatic axonal injury or chronic traumatic encephalopathy (CTE).

364. The method of embodiment 361, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

365. The method of any one of embodiments 331-340, wherein the neurodegenerative disease or disorder comprises an acute disease or disorder of the CNS.

366. The method of embodiment 365, wherein the acute disease or disorder of the CNS comprises an ischemia, a traumatic CNS injury, injury from a chemical agent, thermal injury, or viral encephalitis.

367. The method of embodiment 366, wherein the ischemia comprises cerebral ischemia, hypoxic demyelination, ischemic demyelination, ischemic optic neuropathy, or non-arteritic anterior ischemic optic neuropathy.

368. The method of embodiment 366, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

369. The method of embodiment 366, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

370. The method of any one of embodiments 331-340, wherein the neurodegenerative disease or disorder results from blood clotting issues, inflammation, obesity, aging, stress, cancer, or diabetes.

371. The method of any one of embodiments 327-370, wherein the subject is a human.

372. The method of any one of embodiments 327-371, wherein the subject is a patient with one or more risk factors for developing a condition involving axonal degeneration.

373. The method of embodiments 372, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

374. The method of embodiment 373, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

375. The method of embodiment 373, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

376. The method of embodiment 373, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

377. A method for treating and/or preventing axonal degeneration in a subject, comprising: administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 38.

378. The method of embodiment 377, wherein the antisense oligonucleotide comprises a sequence having at least 85% identity to SEQ ID NO: 38.

379. The method of embodiment 377 or embodiment 378, wherein the antisense oligonucleotide comprises a sequence having at least 90% identity to SEQ ID NO: 38.

380. The method of any one of embodiments 377-379, wherein the antisense oligonucleotide comprises SEQ ID NO: 38.

381. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 38.

382. The method of embodiment 381, wherein the antisense oligonucleotide comprises a sequence having at least 85% identity to SEQ ID NO: 38.

383. The method of embodiment 381 or embodiment 382, wherein the antisense oligonucleotide comprises a sequence having at least 90% identity to SEQ ID NO: 38.

384. The method of any one of embodiments 381-383, wherein the antisense oligonucleotide comprises SEQ ID NO: 38.

385. The method of any one of embodiments 377-384, wherein the target nucleic acid encoding SARM1 is a SARM1 mRNA.

386. The method of any one of embodiments 377-385, wherein the antisense oligonucleotide comprises one or more modifications.

387. The method of embodiment 386, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

388. The method of any one of embodiments 377-387, wherein administering the antisense oligonucleotide decreases levels of SARM1 mRNA in the subject.

389. The method of any one of embodiments 377-387, wherein administering the antisense oligonucleotide decreases levels of SARM1 protein in the subject.

390. The method of any one of embodiments 381-389, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

391. The method of any of embodiments 381-389, wherein the neurodegenerative disease or disorder comprises a chronic disease or disorder of the PNS.

392. The method of embodiment 391, wherein the chronic disease or disorder of the PNS comprises a systemic disorder, a pain disorder, or a metabolic disease or disorder.

393. The method of embodiment 391, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

394. The method of embodiment 392, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

395. The method of embodiment 392, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

396. The method of embodiment 392, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

397. The method of any one of embodiments 381-390, the neurodegenerative disease or disorder comprises an acute disease or disorder of the peripheral nervous system.

398. The method of embodiment 397, wherein the acute disease or disorder of the PNS is the result of a mechanical injury, thermal injury, or injury from a chemical agent or chemotherapy.

399. The method of embodiment 398, wherein the mechanical injury comprises a compression or entrapment injury or a pressure injury.

400. The method of embodiment 398, wherein the compression or entrapment injury comprises carpal tunnel syndrome, direct trauma, a penetrating injury, a contusion, a fracture or a dislocated bone.

401. The method of embodiment 398, wherein the pressure injury comprises pressure involving superficial nerves, pressure from a tumor or increased intraocular pressure.

402. The method of embodiment 398, wherein the chemical agent or chemotherapy comprises a cytotoxic anti-cancer agent, thalidomide, an epothilone, a taxane, a vinca alkaloid, a proteasome inhibitor, a platinum-based drug or an auristatin.

403. The method of embodiment 402, wherein the epothilone is ixabepilone.

404. The method of embodiment 402, wherein the taxane is paclitaxel or docetaxel.

405. The method of embodiment 402, wherein the vinca alkaloid is vinblastine, vinorelbine, vincristine, or vindesine.

406. The method of embodiment 402, wherein the proteasome inhibitor is bortezomib.

407. The method of embodiment 402, wherein the platinum-based drug is cisplatin, oxaliplatin, or carboplatin.

408. The method of embodiment 402, wherein the auristatin is conjugated monomethyl auristatin E.

409. The method of any one of embodiments 381-390, wherein the neurodegenerative disease or disorder comprises a chronic disease or disorder of the CNS.

410. The method of embodiment 409, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

411. The method of embodiment 409, wherein the chronic disease or disorder of the CNS comprises an optic nerve disorder, a traumatic CNS injury, or a metabolic disease or disorder.

412. The method of embodiment 411, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

413. The method of embodiment 411, wherein the traumatic CNS injury comprises a traumatic brain injury (TBI), a spinal cord injury, traumatic axonal injury or chronic traumatic encephalopathy (CTE).

414. The method of embodiment 411, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

415. The method of any one of embodiments 381-390, wherein the neurodegenerative disease or disorder comprises an acute disease or disorder of the CNS.

416. The method of embodiment 415, wherein the acute disease or disorder of the CNS comprises an ischemia, a traumatic CNS injury, injury from a chemical agent, thermal injury, or viral encephalitis.

417. The method of embodiment 416, wherein the ischemia comprises cerebral ischemia, hypoxic demyelination, ischemic demyelination, ischemic optic neuropathy, or non-arteritic anterior ischemic optic neuropathy.

418. The method of embodiment 416, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

419. The method of embodiment 416, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

420. The method of any one of embodiments 381-390, wherein the neurodegenerative disease or disorder results from blood clotting issues, inflammation, obesity, aging, stress, cancer, or diabetes.

421. The method of any one of embodiments 377-420, wherein the subject is a human.

422. The method of any one of embodiments 377-421, wherein the subject is a patient with one or more risk factors for developing a condition involving axonal degeneration.

423. The method of embodiments 422, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

424. The method of embodiment 423, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

425. The method of embodiment 423, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

426. The method of embodiment 423, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

427. A method for treating and/or preventing axonal degeneration in a subject, comprising:

administering to the subject an antisense oligonucleotide that is complementary to a target region of a nucleic acid encoding Sterile Alpha and TIR motif-containing 1 (SARM1), wherein the antisense oligonucleotide comprises a sequence having at least 80% identity SEQ ID NO: 549.

428. The method of embodiment 427, wherein the antisense oligonucleotide comprises a sequence having at least 85% identity to SEQ ID NO: 549.

429. The method of embodiment 427 or embodiment 428, wherein the antisense oligonucleotide comprises a sequence having at least 90% identity to SEQ ID NO: 549.

430. The method of any one of embodiments 427-429, wherein the antisense oligonucleotide comprises SEQ ID NO: 549.

431. A method comprising administering to a subject at risk of developing a neurodegenerative disease or disorder an antisense oligonucleotide that is complementary to a target region of a nucleic acid encoding SARM1, wherein the antisense oligonucleotide comprises a sequence having at least 80% identity SEQ ID NO: 549.

432. The method of embodiment 431, wherein the antisense oligonucleotide comprises a sequence having at least 85% identity to SEQ ID NO: 549.

433. The method of embodiment 431 or embodiment 432, wherein the antisense oligonucleotide comprises a sequence having at least 90% identity to SEQ ID NO: 549.

434. The method of any one of embodiments 431-433, wherein the antisense oligonucleotide comprises SEQ ID NO: 549.

435. The method of any one of embodiments 427-434, wherein the target nucleic acid encoding SARM1 is a SARM1 mRNA.

436. The method of any one of embodiments 427-425, wherein the antisense oligonucleotide comprises one or more modifications.

437. The method of embodiment 436, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

438. The method of any one of embodiments 427-437, wherein administering the antisense oligonucleotide decreases levels of SARM1 mRNA in the subject.

439. The method of any one of embodiments 427-437, wherein administering the antisense oligonucleotide decreases levels of SARM1 protein in the subject.

440. The method of any one of embodiments 431-439, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

441. The method of any of embodiments 431-439, wherein the neurodegenerative disease or disorder comprises a chronic disease or disorder of the PNS.

442. The method of embodiment 441, wherein the chronic disease or disorder of the PNS comprises a systemic disorder, a pain disorder, or a metabolic disease or disorder.

443. The method of embodiment 441, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

444. The method of embodiment 442, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

445. The method of embodiment 442, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

446. The method of embodiment 442, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

447. The method of any one of embodiments 431-440, the neurodegenerative disease or disorder comprises an acute disease or disorder of the peripheral nervous system.

448. The method of embodiment 447, wherein the acute disease or disorder of the PNS is the result of a mechanical injury, thermal injury, or injury from a chemical agent or chemotherapy.

449. The method of embodiment 448, wherein the mechanical injury comprises a compression or entrapment injury or a pressure injury.

450. The method of embodiment 448, wherein the compression or entrapment injury comprises carpal tunnel syndrome, direct trauma, a penetrating injury, a contusion, a fracture or a dislocated bone.

451. The method of embodiment 448, wherein the pressure injury comprises pressure involving superficial nerves, pressure from a tumor or increased intraocular pressure.

452. The method of embodiment 448, wherein the chemical agent or chemotherapy comprises a cytotoxic anti-cancer agent, thalidomide, an epothilone, a taxane, a vinca alkaloid, a proteasome inhibitor, a platinum-based drug or an auristatin.

453. The method of embodiment 452, wherein the epothilone is ixabepilone.

454. The method of embodiment 452, wherein the taxane is paclitaxel or docetaxel.

455. The method of embodiment 452, wherein the vinca alkaloid is vinblastine, vinorelbine, vincristine, or vindesine.

456. The method of embodiment 452, wherein the proteasome inhibitor is bortezomib.

457. The method of embodiment 452, wherein the platinum-based drug is cisplatin, oxaliplatin, or carboplatin.

458. The method of embodiment 452, wherein the auristatin is conjugated monomethyl auristatin E.

459. The method of any one of embodiments 431-440, wherein the neurodegenerative disease or disorder comprises a chronic disease or disorder of the CNS.

460. The method of embodiment 459, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

461. The method of embodiment 459, wherein the chronic disease or disorder of the CNS comprises an optic nerve disorder, a traumatic CNS injury, or a metabolic disease or disorder.

462. The method of embodiment 461, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

463. The method of embodiment 461, wherein the traumatic CNS injury comprises a traumatic brain injury (TBI), a spinal cord injury, traumatic axonal injury or chronic traumatic encephalopathy (CTE).

464. The method of embodiment 461, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

465. The method of any one of embodiments 431-440, wherein the neurodegenerative disease or disorder comprises an acute disease or disorder of the CNS.

466. The method of embodiment 465, wherein the acute disease or disorder of the CNS comprises an ischemia, a traumatic CNS injury, injury from a chemical agent, thermal injury, or viral encephalitis.

467. The method of embodiment 465, wherein the ischemia comprises cerebral ischemia, hypoxic demyelination, ischemic demyelination, ischemic optic neuropathy, or non-arteritic anterior ischemic optic neuropathy.

468. The method of embodiment 465, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

469. The method of embodiment 465, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

470. The method of any one of embodiments 431-440, wherein the neurodegenerative disease or disorder results from blood clotting issues, inflammation, obesity, aging, stress, cancer, or diabetes.

471. The method of any one of embodiments 427-470, wherein the subject is a human.

472. The method of any one of embodiments 427-471, wherein the subject is a patient with one or more risk factors for developing a condition involving axonal degeneration.

473. The method of embodiments 472, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

474. The method of embodiment 473, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

475. The method of embodiment 473, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

476. The method of embodiment 473, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

477. An antisense oligonucleotide comprising a sequence having at least 80% identity to SEQ ID NO: 2410.

478. The antisense oligonucleotide of embodiment 477, comprising a sequence having at least 85% identity to SEQ ID NO: 2410.

479. The antisense oligonucleotide of embodiment 477 or embodiment 478, comprising a sequence having at least 90% identity to SEQ ID NO: 2410.

480. The antisense oligonucleotide of any one of embodiments 477-479, comprising SEQ ID NO: 2410.

481. The antisense oligonucleotide of any one of embodiments 477-480, wherein the antisense oligonucleotide comprises one or more modifications.

482. The antisense oligonucleotide of embodiment 481, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

483. A pharmaceutical composition comprising an antisense oligonucleotide of any one embodiments 477-482.

484. The pharmaceutical composition of embodiment 483, wherein the pharmaceutical composition comprises a pharmaceutically acceptable carrier.

485. A method for treating and/or preventing axonal degeneration in a subject, comprising:
   administering to the subject an antisense oligonucleotide is complementary to a target region of a nucleic acid encoding Sterile Alpha and TIR motif-containing 1 (SARM1).

486. A method comprising administering to a subject at risk of developing a neurodegenerative disease or disorder an antisense oligonucleotide that is complementary to a target region of a nucleic acid encoding SARM1.

487. The method of embodiment 485 or embodiment 486, wherein the target nucleic acid encoding SARM1 is a SARM1 mRNA.

488. The method of any one of embodiments 485-487, wherein the antisense oligonucleotide comprises a sequence having at least 80% identity to SEQ ID NO: 2410.

489. The method of any one of embodiments 485-488, wherein the antisense oligonucleotide comprises a sequence having at least 85% identity to SEQ ID NO: 2410.

490. The method of any one of embodiments 485-489, wherein the antisense oligonucleotide comprises a sequence having at least 90% identity to SEQ ID NO: 2410.

491. The method of any one of embodiments 485-490, wherein the antisense oligonucleotide comprises SEQ ID NO: 2410.

492. The method of any one of embodiments 485-491, wherein the antisense oligonucleotide comprises one or more modifications.

493. The method of embodiment 492, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

494. The method of any one of embodiments 485-493, wherein administering the antisense oligonucleotide decreases levels of SARM1 mRNA in the subject.

495. The method of any one of embodiments 485-493, wherein administering the antisense oligonucleotide decreases levels of SARM1 protein in the subject.

496. The method of any one of embodiments 486-495, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

497. The method of any of embodiments 486-495, wherein the neurodegenerative disease or disorder comprises a chronic disease or disorder of the PNS.

498. The method of embodiment 497, wherein the chronic disease or disorder of the PNS comprises a systemic disorder, a pain disorder, or a metabolic disease or disorder.

499. The method of embodiment 497, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

500. The method of embodiment 498, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

501. The method of embodiment 498, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

502. The method of embodiment 498, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

503. The method of any one of embodiments 486-496, the neurodegenerative disease or disorder comprises an acute disease or disorder of the peripheral nervous system.

504. The method of embodiment 503, wherein the acute disease or disorder of the PNS is the result of a mechanical injury, thermal injury, or injury from a chemical agent or chemotherapy.

505. The method of embodiment 504, wherein the mechanical injury comprises a compression or entrapment injury or a pressure injury.

506. The method of embodiment 505, wherein the compression or entrapment injury comprises carpal tunnel syndrome, direct trauma, a penetrating injury, a contusion, a fracture or a dislocated bone.

507. The method of embodiment 505, wherein the pressure injury comprises pressure involving superficial nerves, pressure from a tumor or increased intraocular pressure.

508. The method of embodiment 504, wherein the chemical agent or chemotherapy comprises a cytotoxic anticancer agent, thalidomide, an epothilone, a taxane, a vinca alkaloid, a proteasome inhibitor, a platinum-based drug or an auristatin.

509. The method of embodiment 508, wherein the epothilone is ixabepilone.

510. The method of embodiment 508, wherein the taxane is paclitaxel or docetaxel.

511. The method of embodiment 508, wherein the vinca alkaloid is vinblastine, vinorelbine, vincristine, or vindesine.

512. The method of embodiment 508, wherein the proteasome inhibitor is bortezomib.

513. The method of embodiment 508, wherein the platinum-based drug is cisplatin, oxaliplatin, or carboplatin.

514. The method of embodiment 508, wherein the auristatin is conjugated monomethyl auristatin E.

515. The method of any one of embodiments 486-496, wherein the neurodegenerative disease or disorder comprises a chronic disease or disorder of the CNS.

516. The method of embodiment 515, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

517. The method of embodiment 515, wherein the chronic disease or disorder of the CNS comprises an optic nerve disorder, a traumatic CNS injury, or a metabolic disease or disorder.

518. The method of embodiment 517, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

519. The method of embodiment 517, wherein the traumatic CNS injury comprises a traumatic brain injury (TBI), a spinal cord injury, traumatic axonal injury or chronic traumatic encephalopathy (CTE).

520. The method of embodiment 517, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

521. The method of any one of embodiments 486-496, wherein the neurodegenerative disease or disorder comprises an acute disease or disorder of the CNS.

522. The method of embodiment 521, wherein the acute disease or disorder of the CNS comprises an ischemia, a traumatic CNS injury, injury from a chemical agent, thermal injury, or viral encephalitis.

523. The method of embodiment 522, wherein the ischemia comprises cerebral ischemia, hypoxic demyelination, ischemic demyelination, ischemic optic neuropathy, or non-arteritic anterior ischemic optic neuropathy.

524. The method of embodiment 522, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

525. The method of embodiment 522, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

526. The method of any one of embodiments 486-496, wherein the neurodegenerative disease or disorder results from blood clotting issues, inflammation, obesity, aging, stress, cancer, or diabetes.

527. The method of any one of embodiments 485-526, wherein the subject is a human.

528. The method of any one of embodiments 485-527, wherein the subject is a patient with one or more risk factors for developing a condition involving axonal degeneration.

529. The method of embodiments 528, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

530. The method of embodiment 529, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

531. The method of embodiment 529, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

532. The method of embodiment 529, wherein the one or more biomarkers of neurodegeneration comprises:
    concentration of neurofilament light chain protein (NF-L) in one or more of: a cerebrospinal fluid (CSF) sample, a blood sample, and a plasma sample from the subject;
    concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

533. An antisense oligonucleotide comprising a sequence having at least 80% identity to SEQ ID NO: 2411.

534. The antisense oligonucleotide of embodiment 533, comprising a sequence having at least 85% identity to SEQ ID NO: 2411.

535. The antisense oligonucleotide of embodiment 533 or embodiment 534, comprising a sequence having at least 90% identity to SEQ ID NO: 2411.

536. The antisense oligonucleotide of any one of embodiments 533-535, comprising SEQ ID NO: 2411.

537. The antisense oligonucleotide of any one of embodiments 533-536, wherein the antisense oligonucleotide comprises one or more modifications.

538. The antisense oligonucleotide of embodiment 537, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

539. A pharmaceutical composition comprising an antisense oligonucleotide of any one embodiments 533-538.

540. The pharmaceutical composition of embodiment 539, wherein the pharmaceutical composition comprises a pharmaceutically acceptable carrier.

541. A method for treating and/or preventing axonal degeneration in a subject, comprising:

administering to the subject an antisense oligonucleotide is complementary to a target region of a nucleic acid encoding Sterile Alpha and TIR motif-containing 1 (SARM1).

542. A method comprising administering to a subject at risk of developing a neurodegenerative disease or disorder an antisense oligonucleotide that is complementary to a target region of a nucleic acid encoding SARM1.

543. The method of embodiment 541 or embodiment 542, wherein the target nucleic acid encoding SARM1 is a SARM1 mRNA.

544. The method of any one of embodiments 541-543, wherein the antisense oligonucleotide comprises a sequence having at least 80% identity to SEQ ID NO: 2411.

545. The method of any one of embodiments 541-544, wherein the antisense oligonucleotide comprises a sequence having at least 85% identity to SEQ ID NO: 2411.

546. The method of any one of embodiments 541-545, wherein the antisense oligonucleotide comprises a sequence having at least 90% identity to SEQ ID NO: 2411.

547. The method of any one of embodiments 541-546, wherein the antisense oligonucleotide comprises SEQ ID NO: 2411.

548. The method of any one of embodiments 541-547, wherein the antisense oligonucleotide comprises one or more modifications.

549. The method of embodiment 548, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

550. The method of any one of embodiments 541-549, wherein administering the antisense oligonucleotide decreases levels of SARM1 mRNA in the subject.

551. The method of any one of embodiments 541-549, wherein administering the antisense oligonucleotide decreases levels of SARM1 protein in the subject.

552. The method of any one of embodiments 542-551, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

553. The method of any of embodiments 542-551, wherein the neurodegenerative disease or disorder comprises a chronic disease or disorder of the PNS.

554. The method of embodiment 553, wherein the chronic disease or disorder of the PNS comprises a systemic disorder, a pain disorder, or a metabolic disease or disorder.

555. The method of embodiment 553, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

556. The method of embodiment 554, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

557. The method of embodiment 554, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

558. The method of embodiment 554, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

559. The method of any one of embodiments 542-552, the neurodegenerative disease or disorder comprises an acute disease or disorder of the peripheral nervous system.

560. The method of embodiment 559, wherein the acute disease or disorder of the PNS is the result of a mechanical injury, thermal injury, or injury from a chemical agent or chemotherapy.

561. The method of embodiment 560, wherein the mechanical injury comprises a compression or entrapment injury or a pressure injury.

562. The method of embodiment 561, wherein the compression or entrapment injury comprises carpal tunnel syndrome, direct trauma, a penetrating injury, a contusion, a fracture or a dislocated bone.

563. The method of embodiment 561, wherein the pressure injury comprises pressure involving superficial nerves, pressure from a tumor or increased intraocular pressure.

564. The method of embodiment 560, wherein the chemical agent or chemotherapy comprises a cytotoxic anticancer agent, thalidomide, an epothilone, a taxane, a vinca alkaloid, a proteasome inhibitor, a platinumbased drug or an auristatin.

565. The method of embodiment 564, wherein the epothilone is ixabepilone.

566. The method of embodiment 564, wherein the taxane is paclitaxel or docetaxel.

567. The method of embodiment 564, wherein the vinca alkaloid is vinblastine, vinorelbine, vincristine, or vindesine.

568. The method of embodiment 564, wherein the proteasome inhibitor is bortezomib.

569. The method of embodiment 564, wherein the platinum-based drug is cisplatin, oxaliplatin, or carboplatin.

570. The method of embodiment 564, wherein the auristatin is conjugated monomethyl auristatin E.

571. The method of any one of embodiments 542-552, wherein the neurodegenerative disease or disorder comprises a chronic disease or disorder of the CNS.

572. The method of embodiment 571, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

573. The method of embodiment 571, wherein the chronic disease or disorder of the CNS comprises an optic nerve disorder, a traumatic CNS injury, or a metabolic disease or disorder.

574. The method of embodiment 573, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

575. The method of embodiment 573, wherein the traumatic CNS injury comprises a traumatic brain injury (TBI), a spinal cord injury, traumatic axonal injury or chronic traumatic encephalopathy (CTE).

576. The method of embodiment 573, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

577. The method of any one of embodiments 542-552, wherein the neurodegenerative disease or disorder comprises an acute disease or disorder of the CNS.

578. The method of embodiment 577, wherein the acute disease or disorder of the CNS comprises an ischemia, a traumatic CNS injury, injury from a chemical agent, thermal injury, or viral encephalitis.

579. The method of embodiment 578, wherein the ischemia comprises cerebral ischemia, hypoxic demyelination, ischemic demyelination, ischemic optic neuropathy, or non-arteritic anterior ischemic optic neuropathy.

580. The method of embodiment 578, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

581. The method of embodiment 578, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

581. The method of any one of embodiments 542-552, wherein the neurodegenerative disease or disorder results from blood clotting issues, inflammation, obesity, aging, stress, cancer, or diabetes.

582. The method of any one of embodiments 541-581, wherein the subject is a human.

583. The method of any one of embodiments 541-582, wherein the subject is a patient with one or more risk factors for developing a condition involving axonal degeneration.

584. The method of embodiments 583, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

585. The method of embodiment 584, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

586. The method of embodiment 584, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

587. The method of embodiment 584, wherein the one or more biomarkers of neurodegeneration comprises:

concentration of neurofilament light chain protein (NF-L) in one or more of: a cerebrospinal fluid (CSF) sample, a blood sample, and a plasma sample from the subject;

concentration of neurofilament heavy chain protein (NF-H) in one or more of: a cerebrospinal fluid (CSF) sample, a blood sample, and a plasma sample from the subject;

concentration of Ubiquitin C-terminal Hydrolase L1 (UCH-L1) in one or more of: a cerebrospinal fluid (CSF) sample, a blood sample, and a plasma sample from the subject;

concentration of alpha-synuclein in one or more of: a cerebrospinal fluid (CSF) sample, a blood sample, and a plasma sample from the subject;

constitutive NAD+ levels in neurons and/or axons of the subject;

constitutive cADPR levels in neurons and/or axons of the subject;

levels of albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

588. An antisense oligonucleotide comprising a sequence having at least 80% identity to SEQ ID NO: 2412.

589. The antisense oligonucleotide of embodiment 588, comprising a sequence having at least 85% identity to SEQ ID NO: 2412.

590. The antisense oligonucleotide of embodiment 588 or embodiment 589, comprising a sequence having at least 90% identity to SEQ ID NO: 2412.

591. The antisense oligonucleotide of any one of embodiments 588-590, comprising SEQ ID NO: 2412.

592. The antisense oligonucleotide of any one of embodiments 588-591, wherein the antisense oligonucleotide comprises one or more modifications.

593. The antisense oligonucleotide of embodiment 592, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

594. A pharmaceutical composition comprising an antisense oligonucleotide of any one embodiments 588-593.

595. The pharmaceutical composition of embodiment 594, wherein the pharmaceutical composition comprises a pharmaceutically acceptable carrier.

596. A method for treating and/or preventing axonal degeneration in a subject, comprising:

administering to the subject an antisense oligonucleotide is complementary to a target region of a nucleic acid encoding Sterile Alpha and TIR motif-containing 1 (SARM1).

597. A method comprising administering to a subject at risk of developing a neurodegenerative disease or disorder an antisense oligonucleotide that is complementary to a target region of a nucleic acid encoding SARM1.

598. The method of embodiment 596 or embodiment 597, wherein the target nucleic acid encoding SARM1 is a SARM1 mRNA.

599. The method of any one of embodiments 596-598, wherein the antisense oligonucleotide comprises a sequence having at least 80% identity to SEQ ID NO: 2412.

600. The method of any one of embodiments 596-599, wherein the antisense oligonucleotide comprises a sequence having at least 85% identity to SEQ ID NO: 2412.

601. The method of any one of embodiments 596-600, wherein the antisense oligonucleotide comprises a sequence having at least 90% identity to SEQ ID NO: 2412.

602. The method of any one of embodiments 596-601, wherein the antisense oligonucleotide comprises SEQ ID NO: 2412.

603. The method of any one of embodiments 596-602, wherein the antisense oligonucleotide comprises one or more modifications.

604. The method of embodiment 603, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

605. The method of any one of embodiments 596-604, wherein administering the antisense oligonucleotide decreases levels of SARM1 mRNA in the subject.

606. The method of any one of embodiments 596-604, wherein administering the antisense oligonucleotide decreases levels of SARM1 protein in the subject.

607. The method of any one of embodiments 597-606, wherein the neurodegenerative disease or disorder comprises an acute or chronic disease or disorder of the peripheral nervous system (PNS), an acute or chronic disease or disorder of the central nervous system (CNS), or a disease associated with neurodegeneration.

608. The method of any of embodiments 597-606, wherein the neurodegenerative disease or disorder comprises a chronic disease or disorder of the PNS.

609. The method of embodiment 608, wherein the chronic disease or disorder of the PNS comprises a systemic disorder, a pain disorder, or a metabolic disease or disorder.

610. The method of embodiment 608, wherein the chronic disease or disorder of the PNS comprises inherited neuropathies, Charcot-Marie-Tooth disease, hereditary sensory and autonomic neuropathy (HSAN), chronic inflammatory demyelinating polyneuropathy (CIDP), idiopathic neuropathies or other peripheral neuropathies.

611. The method of embodiment 609, wherein the systemic disorder comprises diabetes, uremia, AIDS, leprosy, a nutritional deficiency, atherosclerosis, an enteric neuropathy, an axonopathy, Guillain-Barre syndrome, severe acute motor axonal neuropathy (AMAN), systemic lupus erythematosus, scleroderma, sarcoidosis, rheumatoid arthritis, or polyarteritis nodosa.

612. The method of embodiment 609, wherein the pain disorder comprises chronic pain, fibromyalgia, spinal pain, carpal tunnel syndrome, pain from cancer, arthritis, sciatica, headaches, pain from surgery, muscle spasms, back pain, visceral pain, pain from injury, dental pain, neurogenic pain, neuropathic pain, nerve inflammation, nerve damage, shingles, herniated disc, torn ligament, or diabetes.

613. The method of embodiment 609, wherein the metabolic disease or disorder comprises diabetes mellitus, hypoglycemia, uremia, hypothyroidism, hepatic failure, polycythemia, amyloidosis, acromegaly, porphyria, nonalcoholic fatty liver disease (NAFLD), nonalcoholic steatohepatitis (NASH), disorders of lipid/glycolipid metabolism, a nutritional deficiency, a vitamin deficiency, or a mitochondrial disorder.

614. The method of any one of embodiments 597-607, the neurodegenerative disease or disorder comprises an acute disease or disorder of the peripheral nervous system.

615. The method of embodiment 614, wherein the acute disease or disorder of the PNS is the result of a mechanical injury, thermal injury, or injury from a chemical agent or chemotherapy.

616. The method of embodiment 615, wherein the mechanical injury comprises a compression or entrapment injury or a pressure injury.

617. The method of embodiment 616, wherein the compression or entrapment injury comprises carpal tunnel syndrome, direct trauma, a penetrating injury, a contusion, a fracture or a dislocated bone.

618. The method of embodiment 616, wherein the pressure injury comprises pressure involving superficial nerves, pressure from a tumor or increased intraocular pressure.

619. The method of embodiment 615, wherein the chemical agent or chemotherapy comprises a cytotoxic anti-cancer agent, thalidomide, an epothilone, a taxane, a vinca alkaloid, a proteasome inhibitor, a platinum-based drug or an auristatin.

620. The method of embodiment 619, wherein the epothilone is ixabepilone.

621. The method of embodiment 619, wherein the taxane is paclitaxel or docetaxel.

622. The method of embodiment 619, wherein the vinca alkaloid is vinblastine, vinorelbine, vincristine, or vindesine.

623. The method of embodiment 619, wherein the proteasome inhibitor is bortezomib.

624. The method of embodiment 619, wherein the platinum-based drug is cisplatin, oxaliplatin, or carboplatin.

625. The method of embodiment 619, wherein the auristatin is conjugated monomethyl auristatin E.

626. The method of any one of embodiments 597-607, wherein the neurodegenerative disease or disorder comprises a chronic disease or disorder of the CNS.

627. The method of embodiment 626, wherein the chronic disease or disorder of the CNS comprises Alzheimer's disease, Parkinson's disease, amyotrophic lateral sclerosis (ALS, Lou Gehrig's disease), multiple sclerosis (MS), Huntington's disease (HD), senile dementia, Pick's disease, Gaucher's disease, Hurler syndrome, progressive multifocal leukoencephalopathy, Alexander's disease, congenital hypomyelination, encephalomyelitis, acute disseminated encephalomyelitis, central pontine myelolysis, osmotic hyponatremia, Tay-Sachs disease, motor neuron disease, ataxia, spinal muscular atrophy (SMA), Niemann-Pick disease, acute hemorrhagic leukoencephalitis, trigeminal neuralgia, Bell's palsy, cerebral ischemia, multiple system atrophy, Pelizaeus Merzbacher disease, periventricular leukomalacia, a hereditary ataxia, noise-induced hearing loss, congenital hearing loss, age-related hearing loss, Creutzfeldt-Jakob disease, transmissible spongiform encephalopathy, Lewy Body Dementia, frontotemporal dementia, amyloidosis, diabetic neuropathy, globoid cell leukodystrophy (Krabbe's disease), Bassen-Kornzweig syndrome, transverse myelitis, motor neuron disease, a spinocerebellar ataxia, pre-eclampsia, hereditary spastic paraplegias, spastic paraparesis, familial spastic paraplegia, French settlement disease, Strumpell-Lorrain disease, non-alcoholic steatohepatitis (NASH), adrenomyeloneuropathy, progressive supra nuclear palsy (PSP), Friedrich's ataxia, or spinal cord injury.

628. The method of embodiment 626, wherein the chronic disease or disorder of the CNS comprises an optic nerve disorder, a traumatic CNS injury, or a metabolic disease or disorder.

629. The method of embodiment 628, wherein the optic nerve disorder comprises an acute optic neuropathy (AON), a genetic or idiopathic retinal condition, Leber congenital amaurosis (LCA), Leber hereditary optic neuropathy (LHON), primary open-angle glaucoma (POAG), acute angle-closure glaucoma (AACG), autosomal dominant optic atrophy, retinal ganglion degeneration, retinitis pigmentosa, an outer retinal neuropathy, optic nerve neuritis, optic nerve degeneration associated with multiple sclerosis, Kjer's optic neuropathy, an ischemic optic neuropathy, a deficiency in vitamin B12, a deficiency in folic acid (vitamin B9), isolated vitamin E deficiency syndrome, non-arteritic anterior ischemic optic neuropathy, exposure to ethambutol, or exposure to cyanide.

630. The method of embodiment 628, wherein the traumatic CNS injury comprises a traumatic brain injury (TBI), a spinal cord injury, traumatic axonal injury or chronic traumatic encephalopathy (CTE).

631. The method of embodiment 628, wherein the metabolic disease or disorder comprises diabetes mellitus, hypoglycemia, Bassen-Kornzweig syndrome, uremia, hypothyroidism, hepatic failure, polycythemia, amyloidosis, acromegaly, porphyria, disorders of lipid/glycolipid metabolism, nutritional/vitamin deficiencies, and mitochondrial disorders.

632. The method of any one of embodiments 597-607, wherein the neurodegenerative disease or disorder comprises an acute disease or disorder of the CNS.

633. The method of embodiment 632, wherein the acute disease or disorder of the CNS comprises an ischemia, a traumatic CNS injury, injury from a chemical agent, thermal injury, or viral encephalitis.

634. The method of embodiment 633, wherein the ischemia comprises cerebral ischemia, hypoxic demyelination, ischemic demyelination, ischemic optic neuropathy, or non-arteritic anterior ischemic optic neuropathy.

635. The method of embodiment 633, wherein the traumatic CNS injury comprises a spinal cord injury, a TBI, a mechanical injury to the head and/or spine, a traumatic injury to the head and/or spine, blunt force trauma, closed head injury, open head injury, exposure to a concussive and/or explosive force, a penetrating injury to the CNS, increased intraocular pressure, or damage from a force which causes axons to deform, stretch, crush or sheer.

636. The method of embodiment 633, wherein the viral encephalitis comprises enterovirus encephalitis, arbovirus encephalitis, herpes simplex virus (HSV) encephalitis, West Nile virus encephalitis, La Crosse encephalitis, Bunyavirus encephalitis, pediatric viral encephalitis, or HIV encephalopathy (HIV-associated dementia).

637. The method of any one of embodiments 597-6070, wherein the neurodegenerative disease or disorder results from blood clotting issues, inflammation, obesity, aging, stress, cancer, or diabetes.

638. The method of any one of embodiments 596-637, wherein the subject is a human.

639. The method of any one of embodiments 596-638, wherein the subject is a patient with one or more risk factors for developing a condition involving axonal degeneration.

640. The method of embodiments 639, wherein the one or more risk factors for developing a condition involving axonal degeneration comprise age, one or more genetic risk factors for neurodegeneration, family history, engaging in one or more high-risk activities, one or more biomarkers of neurodegeneration, or a combination thereof.

641. The method of embodiment 640, wherein the one or more genetic risk factors for neurodegeneration comprise one or more copies of a known genetic risk factor, a hexanucleotide repeat expansion in chromosome 9 open reading frame 72, one or more copies of the ApoE4 allele, or a combination thereof.

642. The method of embodiment 640, wherein engaging in one or more high-risk activities comprises participating in an activity comprising American football, basketball, boxing, diving, field hockey, football, ice hockey, lacrosse, martial arts, rodeo, rugby, ski jumping, water polo, wrestling, baseball, cycling, cheerleading, fencing, track and field, gymnastics, handball, horseback riding, skating, skiing, skateboarding, softball, squash, ultimate Frisbee, volleyball, or windsurfing.

643. The method of embodiment 640, wherein the one or more biomarkers of neurodegeneration comprises:
  concentration of neurofilament light chain protein (NF-L) in one or more of: a cerebrospinal fluid (CSF) sample, a blood sample, and a plasma sample from the subject;
  concentration of neurofilament heavy chain protein (NF-H) in one or more of: a cerebrospinal fluid (CSF) sample, a blood sample, and a plasma sample from the subject;
  concentration of Ubiquitin C-terminal Hydrolase L1 (UCH-L1) in one or more of: a cerebrospinal fluid (CSF) sample, a blood sample, and a plasma sample from the subject;
  concentration of alpha-synuclein in one or more of: a cerebrospinal fluid (CSF) sample, a blood sample, and a plasma sample from the subject;
  constitutive NAD+ levels in neurons and/or axons of the subject;
  constitutive cADPR levels in neurons and/or axons of the subject;
  levels of albumin, amyloid-$\beta$ (A$\beta$)38, A$\beta$40, A$\beta$42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)$\alpha$, sAPP$\beta$, soluble triggering receptor expressed on myeloid cells (sTREM) 2, phospho-tau, or total-tau in one or more of: a cerebrospinal fluid (CSF) sample, a blood sample, a plasma sample, skin biopsy sample, a nerve biopsy sample, and a brain biopsy sample from the subject; and
  levels of C—C Motif Chemokine Ligand (CCL)2, CCL7, CCL12, colony stimulating factor (CSF)1, or Interleukin (IL)6 in one or more of: a cerebrospinal fluid (CSF) sample, a blood sample, a plasma sample, skin biopsy sample, a nerve biopsy sample, and a brain biopsy sample from the subject.

644. The antisense oligonucleotide, pharmaceutical composition, or method of any one of embodiments 1-643, wherein the antisense oligonucleotide is complementary to a target region of a nucleic acid encoding Sterile Alpha and TIR motif-containing 1 (SARM1).

645. The antisense oligonucleotide, pharmaceutical composition, or method of any one of embodiments 1-644, wherein the antisense oligonucleotide comprises internucleotide linkages of the pattern $R_S R_O R_S R_O R_S D_S D_S D_S D_S D_S D_S D_S D_S D_S R_O R_S R_O R_S$, wherein $R_S$ is an RNA (2'-MOE) phosphorothioate bond, $R_O$ is an RNA (2'-MOE) phosphodiester bond and $D_S$ is a DNA phosophorothioate bond.

EXAMPLES

The present teachings, including descriptions provided in the Examples, are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1: Antisense Modulation of SARM1 Transcript in Human Neuroblastoma Cell Line This Example illustrates an in vitro assay used to characterize oligonucleotides. Antisense oligonucleotides complementary to different regions the SARM1 transcript were synthesized and tested for their ability to inhibit the SARM1 transcript in vitro in a human neuroblastoma cell line.

Human Neuroblastoma Cell Line

The human neuroblastoma cell line SH-SY5Y (ATCC-CRL-2266) was cultured in DMEM medium (Sigma-Aldrich) supplemented with 10% fetal bovine serum (Gibco) and 1 mM penicillin-streptomycin (Sigma). Cultures were plated at a density of 100,000 cells/well in a 24-well tissue culture plate coated with poly-D-Lysine (0.1 mg/ml; Sigma) and laminin (3 mg/mL; Invitrogen). Cells were allowed to adhere to the plates in a humidified tissue culture incubator (5% $CO_2$). Cells were transfected at 70% confluence with an antisense oligonucleotide comprising sequences selected from SEQ ID NO: 3-26 at a final concentration of 10-500 nM using Lipofectamine RNAiMAX diluted in Opti-MEM (ThermoFisher). The antisense oligonucleotides contained non-complementary 5-mer sequences 5' and 3' of nucleotide sequences selected from SEQ ID NO: 3-26 and internucleotide linkages of the following pattern (5' to 3'): $R_S R_O R_S$-$R_O R_S D_S D_S D_S D_S D_S D_S D_S D_S D_S D_S R_O R_S R_O R_S$, wherein $R_S$ is an RNA (2'-MOE) phosphorothioate bond, $R_O$ is an RNA (2'-MOE) phosphodiester bond and $D_S$ is a DNA phosophorothioate bond. SARM1 siRNA (20 nM, Dharmacon) was used a positive control. All conditions were run in triplicate. Transfected cells were incubated for 24 to 72 hours and then harvested for RNA analysis. SARM1 transcript levels were evaluated using quantitative PCR carried out using TaqMan Real-Time PCR system (Thermo Fisher). SARM1 RNA levels were normalized to GAPDH (deltaCt) and plate-matched control transfected samples (delta-delta Ct), generating fold-change over control quantitation (2-(delta-deltaCt).

Results

Figure 2:
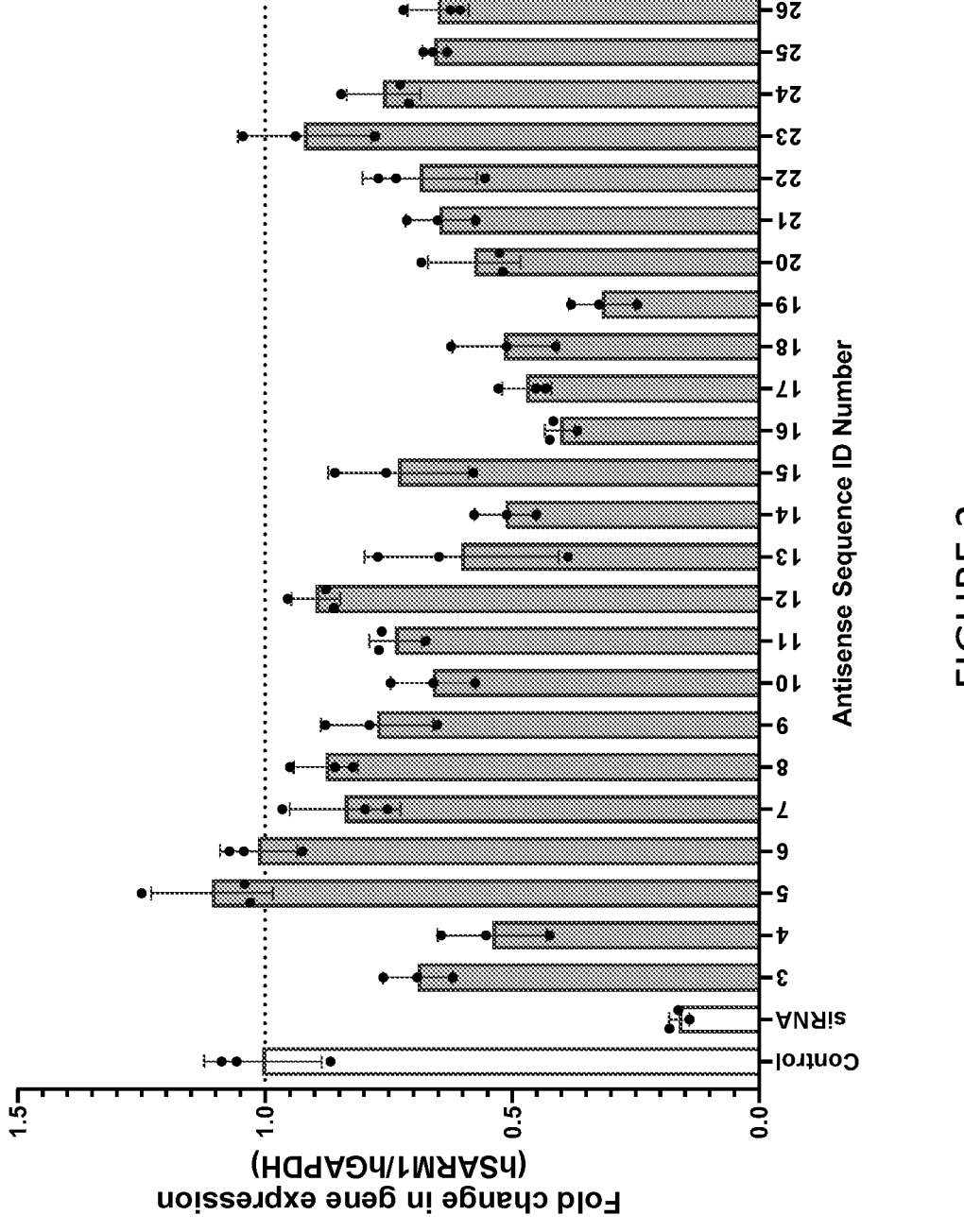
FIG. 2 shows a graph illustrating average fold-change in SARM1 gene expression in cells after transfection with SARM1 antisense oligonucleotides.

The average fold-change over the control transfected cells is plotted in FIG. 2 and a summary over the overall percent knockdown of SARM1 transcript is listed in Table 2.

TABLE 2

Percent knockdown of SARM1 transcript

| SEQ ID NO: | Average Percent Knockdown |
|---|---|
| 3 | 31 |
| 4 | 46 |
| 5 | 0 |
| 6 | 0 |
| 7 | 16 |
| 8 | 12 |
| 9 | 23 |
| 10 | 34 |
| 11 | 26 |

TABLE 2-continued

Percent knockdown of SARM1 transcript

| SEQ ID NO: | Average Percent Knockdown |
|---|---|
| 12 | 11 |
| 13 | 40 |
| 14 | 50 |
| 15 | 27 |
| 16 | 60 |
| 17 | 53 |
| 18 | 59 |
| 19 | 69 |
| 20 | 43 |
| 21 | 35 |
| 22 | 31 |
| 23 | 8 |
| 24 | 24 |
| 25 | 34 |
| 26 | 35 |

Specifically, SEQ ID NO:5 targeted the 5'UTR region, SEQ ID NOs: 4, 17, 18, 20 and 26 targeted the coding region and SEQ ID NOs: 13, 14, 16 and 19 targeted the 3'UTR. Surprisingly, some antisense oligonucleotide (ASO) sequences targeting different regions of the SARM1 transcript produced a robust knockdown of SARM1 expression compared to control, while other ASO sequences had little or no effect. Together, these results confirm that measurable knockdown of the SARM1 transcript can be produced by antisense targeting particular regions of the SARM1 mRNA sequence.

Example 2: Antisense Modulation of SARM1 Transcript in Human Neuroblastoma Cell Line This Example illustrates an in vitro assay used to characterize oligonucleotides. Antisense oligonucleotides complementary to different regions the SARM1 transcript were synthesized and tested for their ability to inhibit the SARM1 transcript in vitro in a human neuroblastoma cell line.

Human Neuroblastoma Cell Line

The human neuroblastoma cell line SH-SY5Y (ATCC-CRL-2266) was cultured in DMEM medium (Sigma-Aldrich) supplemented with 10% fetal bovine serum (Gibco) and 1 mM penicillin-streptomycin (Sigma). Cultures were plated at a density of 100,000 cells/well in a 24-well tissue culture plate coated with poly-D-Lysine (0.1 mg/ml; Sigma) and laminin (3 mg/ml; Invitrogen). Cells were allowed to adhere to the plates in a humidified tissue culture incubator (5% $CO_2$). Cells were transfected at 70% confluence with an antisense oligonucleotide selected from SEQ ID NO: 3-26 at a final concentration of 10-500 nM using Lipofectamine RNAiMAX diluted in Opti-MEM (ThermoFisher). The antisense oligonucleotides contained internucleotide linkages of the following pattern (5' to 3'): $R_S R_O R_S R_O R_S D_S D_S D_S$ $D_S D_S D_S D_S D_S D_S D_S R_O R_S R_O R_S$, wherein $R_S$ is an RNA (2'-MOE) phosphorothioate bond, $R_O$ is an RNA (2'-MOE) phosphodiester bond and $D_S$ is a DNA phosophorothioate bond. SARM1 siRNA (20 nM, Dharmacon) was used a positive control. All conditions were run in triplicate. Transfected cells were incubated for 24 to 72 hours and then harvested for RNA analysis. SARM1 transcript levels were evaluated using quantitative PCR carried out using TaqMan Real-Time PCR system (Thermo Fisher). SARM1 RNA levels were normalized to GAPDH (deltaCt) and plate-matched control transfected samples (delta-delta Ct), generating fold-change over control quantitation (2-(delta-deltaCt).

Results

Figure 3:
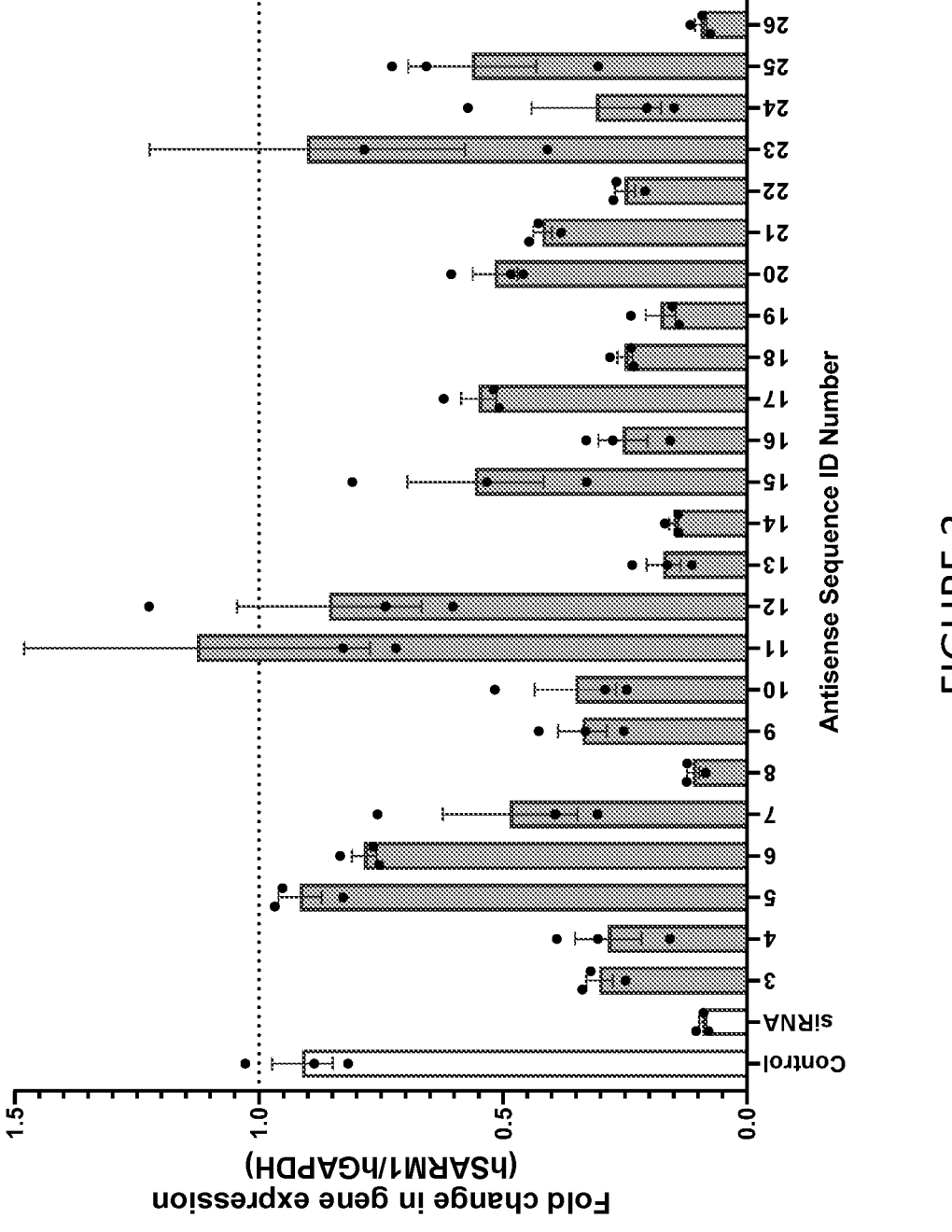
FIG. 3 shows a graph illustrating average fold-change in SARM1 gene expression in cells after transfection with SARM1 antisense oligonucleotides.

The average fold-change over the control transfected cells is plotted in FIG. 3. Specifically, SEQ ID NO:5 targeted the 5'UTR region, SEQ ID NOs: 4, 17, 18, 20 and 26 targeted the coding region and SEQ ID NOs: 13, 14, 16 and 19 targeted the 3'UTR. Surprisingly, some antisense oligonucleotide (ASO) sequences targeting different regions of the SARM1 transcript produced a robust knockdown of SARM1 expression compared to control, while other ASO sequences had little or no effect. Together, these results confirm that measurable knockdown of the SARM1 transcript can be produced by antisense targeting particular regions of the SARM1 mRNA sequence.

Example 3: Antisense Modulation of SARM1
Transcript in Human Motor Neurons

This Example illustrates robust concentration-dependent knockdown of SARM1 gene expression levels in vitro in human induced pluripotent stem cells (IPSC)-derived motor neurons following transfection with antisense oligonucleotides targeting the SARM1 transcript.

Human iPSC-derived motor neurons (Cellular Dynamics-R1049) were cultured and maintained according to the manufacturer's instructions for 14 days using iCell Complete Maintenance Medium plus DAPT (Cellular Dynamics). Motor neuron dispersed cultures were created by seeding 80,000 cells/well in a 24-well tissue culture plate coated with poly-D-Lysine (0.1 mg/ml; Sigma) and laminin (3 mg/ml; Invitrogen). Cells were transfected with 0.1, 0.3, 1, 3 or 10 nM of antisense oligonucleotides comprising SEQ ID NO: 9, 13, 22 or 38 using Lipofectamine RNAiMAX diluted in Opti-MEM (ThermoFisher). The antisense oligonucleotides contained internucleotide linkages of the following pattern (5' to 3'): $R_SR_OR_SR_OR_SD_SD_SD_SD_SD_SD_SD_SD_SD_SD_SR_OR_SR_OR_S$, wherein $R_S$ is an RNA (2'-MOE) phosphorothioate bond, $R_O$ is an RNA (2'-MOE) phosphodiester bond and $D_S$ is a DNA phosophorothioate bond. After 24 hours, a three-quarter medium change was performed to wash and remove the transfection solutions. At 48 hours, the cells were harvested and lysed for TaqMan RT-PCR analysis of SARM1 gene expression levels and normalized to Glyceraldehyde-3-Phosphate Dehydrogenase (GAPDH) gene expression levels. Results are shown in FIG. 4 and data (n=3) are expressed as mean±SEM and normalized to control-treated cells. FIG. 4 illustrates that for all four antisense oligonucleotides, as concentration increased, SARM1 expression in IPSC-derived motor neurons decreased.

Example 4: Antisense Modulation of SARM1
Transcript in Human Motor Neurons after Free
Uptake Delivery This Example illustrates robust concentration-dependent knockdown of SARM1 gene expression levels in vitro in human induced pluripotent stem cells (IPSC)-derived motor neurons following delivery by free uptake (i.e. in the absence of a lipid carrier) with antisense oligonucleotides targeting the SARM1 transcript.

Figure 5:
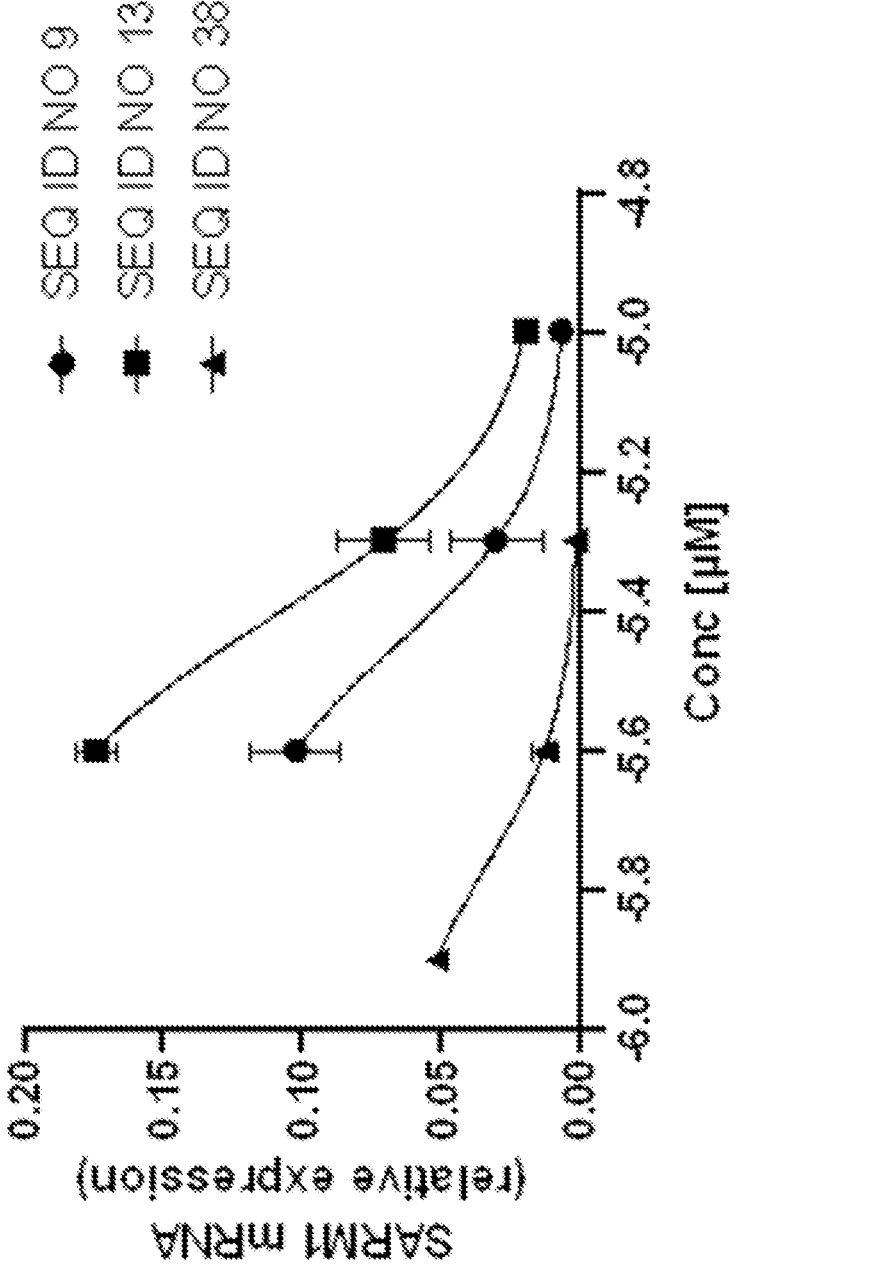
FIG. 5 shows a graph illustrating relative SARM1 mRNA expression in human induced pluripotent stem cells (IPSC)-derived motor neurons following delivery by free uptake (i.e. in the absence of a lipid carrier) with antisense oligonucleotides targeting the SARM1 transcript.

Human iPSC-derived motor neurons (Cellular Dynamics-R1049) were cultured and maintained according to the manufacturer's instructions for 14 days using iCell Complete Maintenance Medium plus DAPT (Cellular Dynamics). Motor neuron cultures were created by seeding 10,000 cells/well in a 96-well tissue culture plate coated with poly-D-Lysine (0.1 mg/ml; Sigma) and laminin (3 mg/ml; Invitrogen). Cells were allowed to adhere to the plates in a humidified tissue culture incubator (5% CO2) and then tissue culture wells were filled with 1 ml of cell culture media. Antisense oligonucleotides comprising SEQ ID NO: 9, 13 or 38 were diluted in Opti-MEM (ThermoFisher) at a concentration range of 1.25 to 10 UM and added to the cell culture media. The antisense oligonucleotides contained internucleotide linkages of the following pattern (5' to 3'): $R_SR_OR_SR_OR_SD_SD_SD_SD_SD_SD_SD_SD_SD_SD_SR_OR_SR_OR_S$, wherein $R_S$ is an RNA (2'-MOE) phosphorothioate bond, $R_O$ is an RNA (2'-MOE) phosphodiester bond and $D_S$ is a DNA phosophorothioate bond. After 9 days, cells were harvested and lysed for TaqMan RT-PCR analysis of SARM1 gene expression levels and normalized to Glyceraldehyde-3-Phosphate Dehydrogenase (GAPDH) gene expression levels. Results are shown in FIG. 5 and data (n=2) are expressed as mean±SEM and normalized to control-treated cells. FIG. 5 illustrates that for all three antisense oligonucleotides, as concentration increased, SARM1 expression in IPSC-derived motor neurons decreased.

Example 5: Time-Dependent Antisense Modulation
of SARM1 Transcript in Human Motor Neurons
After Free Uptake Delivery This Example illustrates time-dependent knockdown of SARM1 gene expression levels in vitro in human induced pluripotent stem cells (IPSC)-derived motor neurons following free uptake (no lipid carrier) delivery with antisense oligonucleotides targeting the SARM1 transcript.

Figure 6:
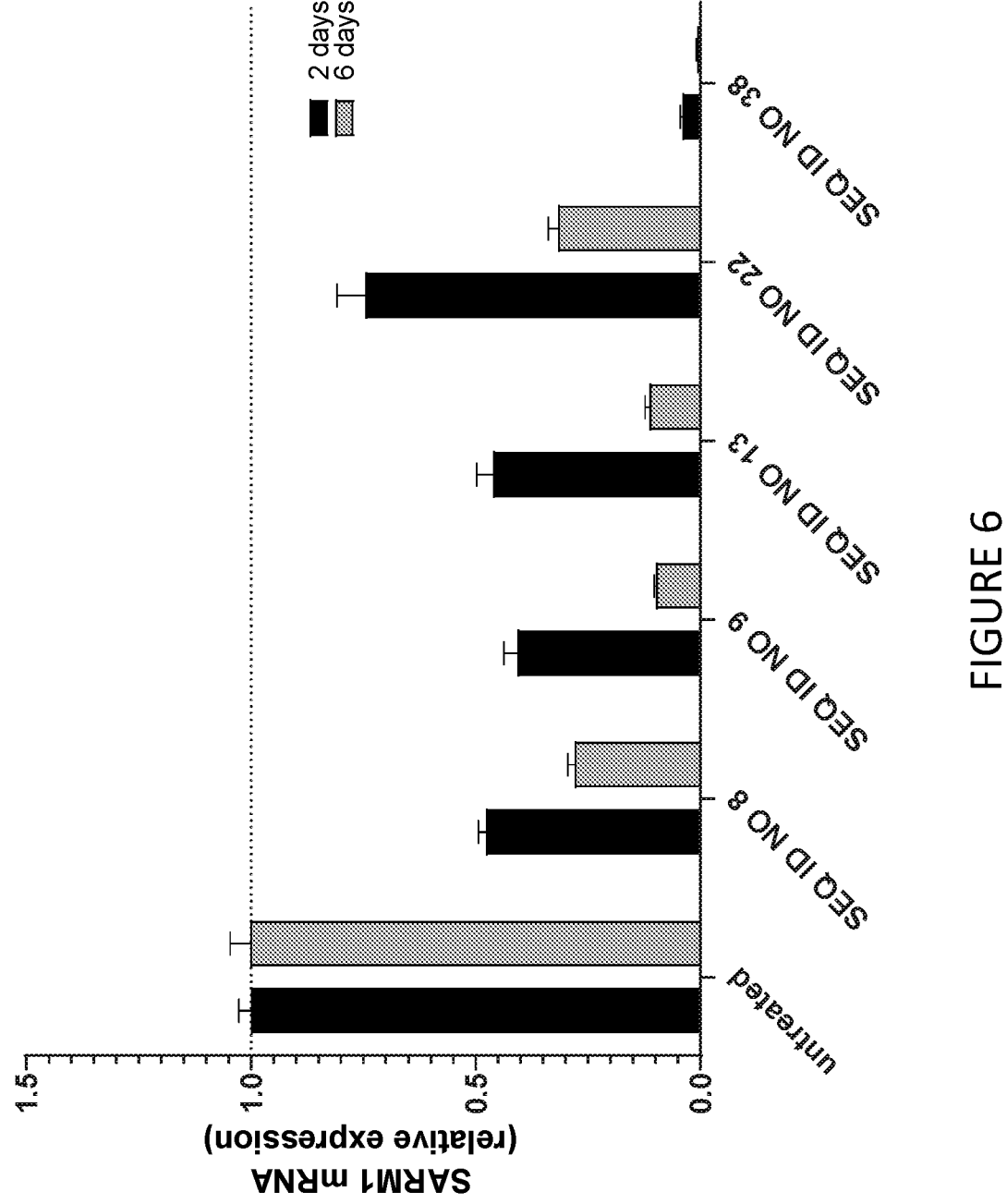
FIG. 6 shows a graph illustrating relative SARM1 mRNA expression in human induced pluripotent stem cells (IPSC)-derived motor neurons 2 days and 6 days following delivery by free uptake (i.e. in the absence of a lipid carrier) with antisense oligonucleotides targeting the SARM1 transcript.

Human iPSC-derived motor neurons (Cellular Dynamics-R1049) were cultured and maintained according to the manufacturer's instructions for 14 days using iCell Complete Maintenance Medium plus DAPT (Cellular Dynamics). Motor neuron cultures were created by seeding 80,000 cells/well as a spot in the center of each well of a 24-well tissue culture plate coated with poly-D-Lysine (0.1 mg/ml; Sigma) and laminin (3 mg/ml; Invitrogen). Cells were allowed to adhere to the plates in a humidified tissue culture incubator (5% CO2) and then tissue culture wells were filled with 1 ml of cell culture media. Antisense oligonucleotides comprising SEQ ID NO: 8, 9, 13, 22 or 38 were diluted in Opti-MEM (ThermoFisher) to a concentration of 10 UM and added to the cell culture media for free uptake delivery. The antisense oligonucleotides contained internucleotide linkages of the following pattern (5' to 3'): $R_SR_OR_SR_OR_S$ $D_SD_SD_SD_SD_SD_SD_SD_SD_SD_SR_OR_SR_OR_S$, wherein $R_S$ is an RNA (2'-MOE) phosphorothioate bond, Rois an RNA (2'-MOE) phosphodiester bond and $D_S$ is a DNA phosophorothioate bond. After 2- or 6-days, cells were harvested and lysed for TaqMan RT-PCR analysis of SARM1 gene expression levels and normalized to Glyceraldehyde-3-Phosphate Dehydrogenase (GAPDH) gene expression levels. Results are shown in FIG. 6 and data (n=3) expressed as mean±SEM and normalized to control-treated cells. FIG. 6 illustrates that for motor neurons treated with any of the five antisense oligonucleotides, SARM1 expression decreased at both time-points relative to the untreated control.

Example 6: SARM1 Antisense Prevents Axonal
Degeneration Following Axotomy in Human
iPSC-Derived Motor Neurons This Example illustrates that treatment with SARM1 antisense oligonucleotides prevented axonal degeneration following axotomy. Specifically, an in vitro axon degeneration assay was used to test the efficacy of oligonucleotides complementary to different regions the SARM1 transcript to prevent axonal degeneration in a human induced pluripotent stem cell (iPSC)-derived motor neuron drop culture.

Human Motor Neuron Drop Culture

Human iPSC-derived motor neurons (Cellular Dynamics-R1049) were cultured and maintained according to the manufacturer's instructions for 14 days using iCell Complete Maintenance Medium plus DAPT (Cellular Dynamics). Motor neuron drop cultures were created by seeding 10,000 cells/well as a spot in the center of each well of a 24-well tissue culture plate coated with poly-D-Lysine (0.1 mg/mL; Sigma) and laminin (3 mg/mL; Invitrogen). Cells were allowed to adhere to the plates in a humidified tissue culture incubator (5% CO2) and then tissue culture wells were filled with 1 ml of cell culture media. Antisense oligonucleotides comprising SEQ ID NO: 9, 22, 38 or 39 were diluted in Opti-MEM (ThermoFisher) to a 5 µM concentration and added to the cell culture media for free uptake delivery. The antisense oligonucleotides contained internucleotide linkages of the following pattern (5' to 3'): $R_S R_O R_S R_O R_S D_S D_S D_S D_S D_S D_S D_S D_S D_S D_S R_O R_S R_O R_S$, wherein $R_S$ is an RNA (2'-MOE) phosphorothioate bond, Rois an RNA (2'-MOE) phosphodiester bond and $D_S$ is a DNA phosophorothioate bond. 10 days post-transfection, the axonal degeneration assay was performed.

Axon Degeneration Assay

Figure 7:
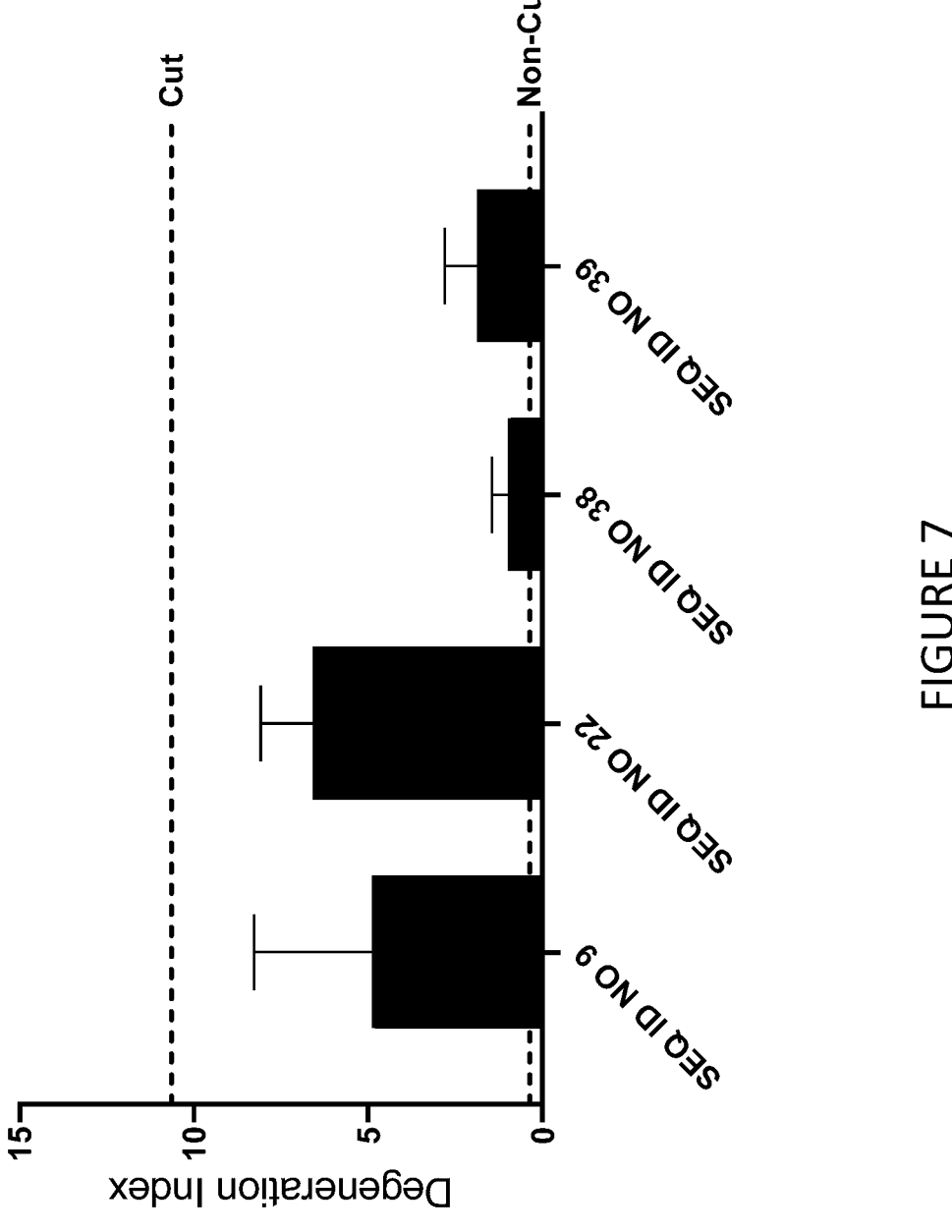
FIG. 7 shows a graph illustrating that SARM1 antisense oligonucleotides prevent axonal degeneration following axotomy in human iPSC-derived motor neurons treated using free uptake delivery.

Axonal degeneration was stimulated by manual axonal transection using a scalpel blade. After 16 hours, motor neuron cultures were fixed in 1% PFA plus sucrose and kept in the refrigerator prior to imaging. Cells were immuno-stained for beta-3 Tubulin (Clone TuJ1, R&D systems), images of motor neuron axons and cell bodies were collected using the 20× water immersion lens of a Phenix automated confocal microscope (PerkinElmer) and quantitation of axons was performed using in-house developed scripts (Acapella, PerkinElmer). The degeneration index reflects the integrity of the axon such that a higher value indicates a greater level of axonal fragmentation and a lower value indicates a lower level of axonal fragmentation. As shown in FIG. 7, ASOs that knock-down SARM1 expression reduced axonal degeneration in this assay. The data in FIG. 7 is expressed as mean±SEM (n=3-4). The dashed line labeled 'Cut' denotes mean level of degeneration observed in control-cut axons and dashed line labeled 'Non-Cut' denotes mean level of degeneration observed in intact control axons.

EXEMPLARY SEQUENCES

Wild-Type Human SARM1 Protein Sequence

```
MVLTLLLSAYKLCRFFAMSGPRPGAERLAVPGPDGGGGTGPWWAAGGRGPREVSPGAGTEVQDALERALPELQQAL
SALKQAGGARAVGAGLAEVFQLVEEAWLLPAVGREVAQGLCDAIRLDGGLDLLLRLLQAPELETRVQAARLLEQILVAE
NRDRVARIGLGVILNLAKEREPVELARSVAGILEHMFKHSEETCQRLVAAGGLDAVLYWCRRTDPALLRHCALALGNCA
LHGGQAVQRRMVEKRAAEWLFPLAFSKEDELLRLHACLAVAVLATNKEVEREVERSGTLALVEPLVASLDPGRFARCLV
DASDTSQGRGPDDLQRLVPLLDSNRLEAQCIGAFYLCAEAAIKSLOGKTKVFSDIGAIQSLKRLVSYSTNGTKSALAKRAL
RLLGEEVPRPILPSVPSWKEAEVQTWLQQIGFSKYCESFREQQVDGDLLLRLTEEELQTDLGMKSGITRKRFFRELTELKT
FANYSTCDRSNLADWLGSLDPRFRQYTYGLVSCGLDRSLLHRVSEQQLLEDCGIHLGVHRARILTAAREMLHSPLPCTG
GKPSGDTPDVFISYRRNSGSQLASLLKVHLQLHGFSVFIDVEKLEAGKFEDKLIQSVMGARNFVLVLSPGALDKCMQDH
DCKDWVHKEIVTALSCGKNIVPIIDGFEWPEPQVLPEDMQAVLTFNGIKWSHEYQEATIEKIIRFLOGRSSRDSSAGSDT
SLEGAAPMGPT (SEQ ID NO: 1).
```

Wild-type human SARM1 cDNA sequence (corresponding to mRNA sequence) (NCBI Accession Number: NM_15077.4) The target sequences of exemplary ASOs are denoted in bold capital letters and in the case where the sequences overlap it is denoted by underline. In the one instance where there is an overlap in ASO targeting, the sequence is denoted in both bold and underlined capital letters.

```
  1    atctcccagctcagccgagcccgtgcccaggccacgctttgttccagccgccgcctcctc 61    taccctacggcgtccggagccatccctcgcctgctcgctctctcctttcgcccactccct 121    gcatctgggcctgcatcacctttgccaaccgctccccgatcctgccgacactcctcccc 181    caaacttctgaccggcacccttgcctggtacccttctctccattcctccccctccatctt 241    ctttccccgacccctctcgggtccctcttttcccaaaacccgggtctctccgcgtggccc 301    cgcctccaggccggggatgtcccccgcggccccgcGCCCATGGTCCTGACGCTGCttctc 361    tccgcctacaagctgtgtcgcttcttcgccatgtcgggcccacggccgggcgccgagcgg 421    ctggcggtgcctgggccagatggggcggtggcacgggcccatggtgggctgcgggtggc 481    cgcgggccccgcgaagtgtcgccggggcaggcaccgaggtgcaggacgccctggagcgc 541    gcgctgccggagctgcagcaggccttgtccgcgctgaagcaggcgggcggcgcgcgggcc 601    gtgggcgccggcctggccgaggtctTCCAACTGGTGGAGGAGGCCtggctgctgccggcc 661    gtgggccgcgaggtagcccagggtctgtgcgacgccatccgcctcgatggcggcctcgac 721    ctgctgttgcggctgctgcaggcgccggagtTGGAGACGCGTGTGCAGGCCgcgcgcctg 781    ctggaGCAGATCCTGGTGGCTGAGAaccgagaccgcgtggcgcgcattgggctgggcgtg 841    atcctgaacctggcgaaggaacgcgaacccgtagagctggcgcgggagcgtggcaggcatc 901    ttggagcacatgttcaagcattcggaggagacatgccagaggctggtggcggccggcggc
```

```
 961  ctggacgcggtgctgtattggtgccgccgcacggaccccgcgctgctgcgccactgcgcg 1021  ctggcgctgggcaactgcgcgctgcacgggggccaggcggtgcagcgacgcatggtagag 1081  aagcgcgcagccgagtggctcttcccgctcgccttctccaaggaggacgagctgcttcgg 1141  ctgcacgcctgcctcgcagtagcggtgttggcgactaacaaggaggtggagcgcgaggtg 1201  gagcgctcgggcacgctggcgctcgtggagccgcttgtggcctcgctggaccctggccgc 1261  ttcgcccgctgtctggtggacgccagcgacacaagccagggccgcgggcccgacgacctg 1321  cagcgcctcgtgccgttgctcgactctaaccgcttggaggcgcagtgcatcggggctttc 1381  tacctctgcgccgaGGCTGCCATCAAGAGCCTGCaaggcaagaccaaggtgttcagcgac 1441  atcggcgccatcCAGAGCCTGAAACGCCTGGTttcctactctaccaatggcactaagtcg 1501  gcgctggccaagcgcgcgctgcGCCTGCTGGGCGAGGAGGTGccacggcccatcctgccc 1561  tccgtgcccagctggaaggaggccgaggttcagacgtggctgcagcagatcggtttctcc 1621  aagtactgcgagagcttccGGGAGCAGCAGGTGGATGGCgacctgcttctgcggctcACG 1681  GAGGAGGAACTCCAGACcgacctgggcatgaaatcgggcatcacccgcaAGAGGTTCTTT 1741  AGGGAGCTCacggagctcaagaccttcgccaactattctacgtgcgaccgcagcaacctg 1801  gcggactggctgggcagcctggacccgcgcttccgccagtacacctacggcctggtcagc 1861  tgcggcctGGACCGCTCCCTGCTGCACCgcgtgtctgagcagcagctgctggaagactgc 1921  ggcatccacctgggcgtgcaccgcgcccgcatcctcacggcggccagagaaatgctacac 1981  tccccgctgccctgtactGGTGGCAAACCCAGTGGGGAcactccagatgtcttcatcagc 2041  taccgccggaactcaggttcccagctggccagtctcctgaaggtgcacctgcagctgcat 2101  ggcttcagtgtcttcattgatgtggaGAAGCTGGAAGCAGGCAAGTtcgaggacaaactc 2161  atccagagtgtcatgggtgcccgcaactttgtgttggtgctatCACCTGGAGCACTGGAC 2221  AAGtgcatgcaagaccatgactgcaaggattgggtgcataaggagattgtgactgcttta 2281  agctgcggcaagaacattgtgcccatcattgatggcttcgagtggcctgagccccaggtc 2341  ctgccTGAGGACATGCAGGCTGTGCttactttcaacggtatcaagtggtcccacgaatac 2401  caggaggccaccattgagaagatcatccgcttcctgcagggccgctcctcccgggactca 2461  tctgcaggctctgacaccagtttggagggtgctgcacccatgggtccaacctaaccagtc 2521  cccagttccccagccctgctgtgacttccatttccatcgtcctttctgaaggaacagctc 2581  ctgaaaccagtc*TCCCTGGGCTGAGACAACCTGGG*ctcttcttaggaaatggctctccct 2641  cccccgtcccccaccctcatggcccacctccaacccactttcctcaGTATCTGGAGAGG 2701  GAAGGGAagtcaggcttgggcacgggaggttagaactcccccaggccctgccattgggtt 2761  gtctgtctccgtcatgggagggtccctgctcagttctggagacactggagtGGGGGTGG 2821  GGGTGGTTCTGCAttcccttctcctgctgatagcagtcagcttgaggaggatgacggaag 2881  gcagcctcagacaggaattaaggcaatgcccaggcgggcctgggcactgtaTTCTGAGCA 2941  AGGGCCTGGGCccaggaGCCAGCCAGGGATGAGTGCCatcatggctctccactcagactg 3001  tgcctggcccctgcacttacaacttcctgccgctctgtggccttgccctgtaatcactca 3061  gtgcccttagctagcctgactaagtcccagatcccctacagcttccttcggtgtggtatc 3121  tttTGCCACATCCAGGGCGAGGGttgaggcaaaccagccctccctctgacttccttgtca 3181  ctgcagccagctttgctgcacttgctggtgcacaggagcctcctgtttggGCCTGGGTCT 3241  GGGCATGGGGaggccgtgcctcaaagcccaccctacccatgccttggtgctgtgcctca
```

-continued

```
3301   ggctccttcctggtctggcccagctggcttccccagcccctcagccatccagggctaccc 3361   actgcttactcagggaccaggcagcccccatggcagtaaaagcagcctagacagaacctG 3421   CAGCTCTGTGGAAAGAGgcaaagtcctgaaaaggcaaagggttgtcacttagggcagctt 3481   ctccaactttaacatgcatccaagtcacctgggaatgttgttaaaatcaggagatctggg 3541   gtggggcctaggactctgcatttcttacagattcccaggtgagctgatgctggtggttaa 3601   gggtagcaaatctctaaagcacgaagccctcacaaatctttgccatttcccaaacactcc 3661   gctccatggtctccagtcatcagagcaactctacctggtattatcatccccattttacag 3721   ataatgacactgaggctcagaaaggttgaggataagcccactttcctgtcattagtggca 3781   gccccagatccagacctaggcctcctggcacccagtccactggcagtggaattgctttcc 3841   tgagaatcattctgaggctgggctattgcttctcccttgcttcaaagaatctagcagcgg 3901   gggataggattttgcaacaaaaagctgacccagaggccatacagagcaggaatatcccat 3961   tgccccctcctccactgggttcagagggtaagaaagcaccctccaataaacccaggctcc 4021   aggccgtgggggctgctgaaggctctttccccgcaagggccaggtgttgacaccttaaag 4081   ctggctgcgccccagccccactcttggctgtgctggccaggtgactcctagttcttggc 4141   cacatcatcagaaagtcaaaggtctcactccaggtttggggctccttccttccactcccc 4201   tccctgccagagtctgtcttggccagtgccagcctcgatgctttggttttgaccccacct 4261   gatcctcctttcctcatgcagcacaagtgctcaccggggccagagccagggcatggatat 4321   gacaagcagggcagcctggacactgccctcacaggacagcgccaataacaatacagtgtc 4381   tgagtatctccaggggatgatttctggctctttgtctccaatcagtcccactccctcctg 4441   aggtccccaagggcagtattcagagaggtttcctgcgttttatttctatttggtataccc 4501   tccactgttgtccactgccctgtgtggccttctggttgacctctgcccgatcttctgtct 4561   ctctgagggaatcagagtccagcatccagccccagctggaacagctgaagtcacaagcct 4621   cctctaagccaaggccagtgtgttcagaggtgactgccacccatactaggacaaacacag 4681   ctcagatcaccaggtcaagcacctaggcctggcttctcctgagacagaggactcagaagt 4741   ggcctttcctccaaagcctgctcagacacaggtctgtagggccaggtgttctgcttggc 4801   tgggctgcagctgctacccctcggttggggctgagtcagccagatcctcccctacttct 4861   ccccaagggccaagaactgctcagggacattaaaggtcaaaagtccagccacactcattc 4921   atcctttccccaggcccatgaagagaggcatctcattgtagaatgtatgaggaagtggga 4981   agtatctcagagaatcagctaagtttcctaacttgtccatccaaatgtgatcaccacgat 5041   tcaacaatttggggcattgctgatctagccgttcctagtggggcttgctcaaggttgcac 5101   agcgagtcagtagaagccctggctggccccacttggtaccaatccaccaggcagctcagg 5161   gctcctgcccagcccagcagcttctgttgtctaacgtatggcaggcagactgggagcagg 5221   aaaacagagggccccaaagcccaaggcaccagaaggtttgtttcagtttgctgaagctga 5281   tttgtaatgattggcactcttcagccaggggagtgggtaggccatagccaaggatcgatt 5341   ccccaaccacagcaaaggcaacactcttcctccagagatcaccaagcccctcttacctcc 5401   ctccctccttcccaaggctggcactaaccaggtaccacattcattgttaaggaatggctg 5461   atgactgctacacgtgttgggaacctggttggggctgtgcagtttgggctggaaggagag 5521   atgccagccctcgtgctgcctctggtccctgaagtgtcacctctctcaggacctctcctc 5581   tggcctgtggggttataagtgatggatagcagaaagggagaactgactcctgtcccaaat 5641   agctcctctgccacctgtcctgcagtgggcctgtgtgggttatgattctagatcctagac
```

-continued

```
5701   agaggctgggtcagctgtggatggggtggtgccttggtctctcttgactacctcgtccaa 5761   agagagcactgcccttagacaagagttgcttgtcctgctgtgggctgggcttccagctgc 5821   agacctccagttgcttggtgttcactttgctcctcttgccctctgtcttctggtccaggc 5881   agatcaggggctctggggaaactgctggaactcgaggtgaggatcagccttttccagcat 5941   cctgtgagagaccagagagagagtttggatttcatgtggggaaccctcaaggcctgtctg 6001   gagaagtgacacaggatttactggggtgggctggtccaggtagctctcctgaacctcctc 6061   cttccccaagctgagaagctgagagctggaggacaatatccagggacatggctctggaaa 6121   ataacttttttttttttaagagacagggtcttgctctgttgtccaggctggagggcagtg 6181   acataatcatagctcactgtacccttgaactcctgggctcaagtgatcctcctgcctcag 6241   cctccttagtagctgggactaccagtgcataccaccatgcctgggtgattttttaaattt 6301   tttatacagacaaggtcttgctatgttgcccaggctgatcttgaattcccgggctcaagt 6361   ggtcctcctgcctcagcctcccacaggatcgggattacaggcaagagcctccacgcccgg 6421   ccatgaaatataattcttaatatcatacaggaaaaagtcagcgggtcaagctagcctgtg 6481   gcccagccacaactagctgacaaagcttcctggccttcccttta acacagttctgctgcc 6541   atagttccatctataaaatgggaatggaggga aatagg ggaactgggagagagaacacag 6601   ccttgccaagcagcaatgttagcctgatccttcctccacctagctcgccatctcgccctt 6661   ggaaaatggctcctggaggattaggcagccatctgcaaggagaggggcaacctgggacaa 6721   gacacccagagggtaaggattccaggaatgaagctgccatttctggttgggaggagaaga 6781   ggaaacttttaagagaaagggctccattatgagcatgggttcagggccctgcattacccca 6841   atcagaacagccgggatgagcaggaggccagctcccaggaggaaggggaaccccttcata 6901   aagttcagagtggctgggtagagtgagttgaagatgccggaggccgtcagcatggccagg 6961   ctattcacacaggccacagcagaaaagagagcacctgtgaagaaataaataccatactct 7021   ggagtccgaaagggccatattccaactctggcaccaccacctcacagctgtgtgaccggg 7081   agtagtcacttaacctatgtctccccttcctcaccagtaaatcctgctacatcatgtact 7141   gtgacaaggattcagtaaggtcatatgtggacagtagctggcacagagggggctactaaac 7201   aaatggctgctattaaatccacattaaaagtacatgtgatctgacagaacccagcacata 7261   aaagaaaaaaaaagtacatgtgatattgtctgatgaaagcttgatggaaatggctttttt 7321   ctggtttatcctctttggaatcatctcctgtttgggattaactgctggtctgatcagttc 7381   caatattcatagcggtgtcaccactgaatagcttcttatcctttgggttcctgttcctcc 7441   ttctgctaaataaggataatacctatttcctagattgtgagcaacattaagttcacatgg 7501   aaatcacccatcactgggcctggtcccctggaagtagctagttagtaagggctgttcttt 7561   tctcctgtttctcttgacatctctgggcacagagaaagtgctgggaaaaaaagtttaggt 7621   gaatgaatgaagacacatggattctggggacaccagaacccacagtgggctctgtatggc 7681   accagagtctctgtcatcatcagatcctcattccaggacagatggaaaaagatgaatgtt 7741   tccagactggggcataaagacccagaggctggagaagctgttctttatagatataccagg 7801   agaacccacagtttacaaaatgtgcaacaacccaacagaagttgagattaaattctgtca 7861   catctagaggggtctgtgatgtcatcaaaagcaaaccacccacatcacagatgaagaaac 7921   aggcctgtggcagggctcggactaaaacccagatcctgagaccagctgcttttaaacaca 4981   gacgtaggtttgcatcctagctccaccatttactgagtaaccttgggtgagccaatgtaa
```

-continued

```
 8041   cccccctgggtctctgtttctttatctgtcaactgtggaaaatgaaacccatgtcacaagg 8101   ttgttcacttctgggcttgtacacgctgaccccagagaaacagggaactctggcatcacc 8161   acacccatcttacagacggaaaagctgaggtctgcagagagtaaatcctctgctctggtt 8221   atctagaaagaacataattgtgctctgctgactgcaaatcccaactctgcggtttgaaaa 8281   tccaaggtggcatgatcctctgcccattgtgggcaatttcacagaaatgtgtttgttttg 8341   gccacttacttctccagggtgagagggggggaaggcaagctgttcccccagccatggctgc 8401   ccatcagcccgtttcgggcagcactggacatgaggaaccagacacaggtgggttctgaca 8461   ctcaccctgctctgtctctctcaccagcttggagagtttagcccggatgacaggtgtgat 8521   gactaatgacaggaaaagcaacccatatcctgtggagaaacaaacactcatcaggaaaat 8581   ggggctggggagaggggcgtccaagggaaaggcagcagagctcctatccataccccacgt 8641   ggggcttaggttagacccaggaagaacttccttgatggtgagggtgggaagacagtagtc 8701   aaggaggaatggagactgcccttgtctgggcttggccacctgctagctctcatgaatgaa 8761   tgctaattcccattgattgctttcttgtctgaacctcttgtggtcacagcaggcatcacc 8821   cacccacttggcacttagtagggatatggcagggcacagaaaacaagcatgggctttgga 8881   gtcagccctgagttcaaaacctgatgccattacatattatctgtgtggcctggggtactt 8941   accctctctgatcctgactccctgtatgaggaagataataaggccttcatcacaggatgg 9001   ttctgaggcataggaggctgaataatggtgcccaatggcatcagattcatagccctggaa 9061   cctgtaaatactaccttatttggaaaatgagtctatgcaggtgtgcagttaagcctcctg 9121   agagagcagagttatcctggattaggttgggccctaaatgccgtcacacatatctttata 9181   agaggaaagcagacggagatttggcaccgacagaattgagaaggcacaaagaggaggaga 9241   gtcaatgtgagcacagaggcagagactggtgatggccgccccaagccaaggaatgccagc 9301   agccccagaagctggaagaaatgagaaacacgttctctcctggaggcttgcaagggagca 9361   ctgcctgctgactgcttccattcagcccggtggtactgactttggacttctggcctccag 9421   aactgtgagagaatatgtttctgttgtgttaagcccccaagtttgtggtatgtcattaca 9481   gcaatctcagggaaccaatacatgaggtaaaaaggtaacatctatgaagagcatggcata 9541   gggacacagcaaatgggagttcctttcccctttgcattcagttacttacaggcttcctgt 9601   tttcttcataaccatttctctccctgtgcgactgctgactcctcagcaaaactgcaaact 9661   cctacaggacagtggatcctccaaagaaggtatacgatgaggcatccagggaccctagca 9721   gtgtcaggcccctcaaatcccactctgttgagacctccccccgacccagagcaatgacag 9781   catctttatcatctctgcatcccccagggccatcagcaggagggaaaggttcccttctgc 9841   ttaattgtcagacaagcagttgagttaagaaatctgtgattattgtattgttgactatac 9901   acagcacattttagggctctatcaaaataaatctgtccctttaaaaaaagttaactaaag 9961   ccgggcacggtggctcatgcctgtaatcccaacactttgggaggctgaggcaggcggatc 10021   cttgagctcaggagttagagacctggactgggcaaaatggtgaggaccccatctctataa 10081   aaaatacaaaaattagcaaggtgtggtaatgtgcaccagtggtcccagctactagagagg 10141   ccaaggtgggaggatcatctgggcccgggggatgaggctgcagtgagccatgatcgtgcc 10201   actgcactctagcctgggtaacaaagcgagaccctgtctctaaatacatcaatcaaataa 10261   aaattttaaaaagttaa (SEQ ID NO: 2)
```

-continued

| Table 3-SARM1 antisense oligonucleotide sequences | |
|---|---|
| Antisense Oligonucleotide Sequence | SEQ ID NO: |
| GGCCTCCTCCACCAGTTGGA | 3 |
| GCAGGCTCTTGATGGCAGCC | 4 |
| GCCATCCACCTGCTGCTCCC | 5 |
| TCCCCACTGGGTTTGCCACC | 6 |
| ACTTGCCTGCTTCCAGCTTC | 7 |
| CTTGTCCAGTGCTCCAGGTG | 8 |
| GCACAGCCTGCATGTCCTCA | 9 |
| CCCAGGTTGTCTCAGCCCAG | 10 |
| TCCCTTCCCTCTCCAGATAC | 11 |
| TGCAGAACCACCCCCACCCC | 12 |
| GCCCAGGCCCTTGCTCAGAA | 13 |
| GGCACTCATCCCTGGCTGGC | 14 |
| CCCCATGCCCAGACCCAGGC | 15 |
| GCCTCTTTCCACAGAGCTGC | 16 |
| TCTCAGCCACCAGGATCTGC | 17 |
| GAGCTCCCTAAAGAACCTCT | 18 |
| CCAGGTTGTCTCAGCCCAGG | 19 |
| GGTGCAGCAGGGAGCGGTCC | 20 |
| GCAGCGTCAGGACCATGGGC | 21 |
| ACCAGGCGTTTCAGGCTCTG | 22 |
| CACCTCCTCGCCCAGCAGGC | 23 |
| GTCTGGAGTTCCTCCTCCGT | 24 |
| CCCTCGCCCTGGATGTGGCA | 25 |
| GGCCTGCACACGCGTCTCCA | 26 |
| ACTTGTCCAGTGCTCCAGGT | 27 |
| AGCACAGCCTGCATGTCCTC | 28 |
| GCCCAGGTTGTCTCAGCCCA | 29 |
| GCACTCATCCCTGGCTGGCT | 30 |
| ATGCCCAGACCCAGGCCCAA | 31 |
| AGGCTCTTGATGGCAGCCTC | 32 |
| TTCTCAGCCACCAGGATCTG | 33 |
| GGTTCTCAGCCACCAGGATC | 34 |
| GTGAGCTCCCTAAAGAACCT | 35 |
| TTGTCCAGTGCTCCAGGTGA | 36 |
| GGTTGTCTCAGCCCAGGGAG | 37 |
| AGGTTGTCTCAGCCCAGGGA | 38 |
| CAGGTTGTCTCAGCCCAGGG | 39 |
| CACTCATCCCTGGCTGGCTC | 40 |

-continued

```
TGGCACTCATCCCTGGCTGG                                       41

AGCTCCCTAAAGAACCTCTT                                       42

CTCCCTAAAGAACCTCTTGC                                       43

GCTCCCTAAAGAACCTCTTG                                       44

TGAGCTCCCTAAAGAACCTC                                       45

GTGCAGCAGGGAGCGGTCCA                                       46

CCAGGCGTTTCAGGCTCTGG                                       47

CAGGCGTTTCAGGCTCTGGA                                       48

CGGTTCTCAGCCACCAGGAT                                       49

AGGCGTTTCAGGCTCTGGAT                                       50

AACCAGGCGTTTCAGGCTCT                                       51

CCATCCACCTGCTGCTCCCG                                       52

TGGCACCTCCTCGCCCAGCA                                       53

GGTCGCCATCCACCTGCTGC                                       54

GTCGCCATCCACCTGCTGCT                                       55

CGCCATCCACCTGCTGCTCC                                       56

ATCCACCTGCTGCTCCCGGA                                       57

TCGCCATCCACCTGCTGCTC                                       58

CATCCACCTGCTGCTCCCGG                                       59

GTGGCACCTCCTCGCCCAGC                                       60

GGTCGGTCTGGAGTTCCTCC                                       61

GTCGGTCTGGAGTTCCTCCT                                       62

ACCCTCGCCCTGGATGTGGC                                       63

GAGTTCCTCCTCCGTGAGCC                                       64

GGTCTGGAGTTCCTCCTCCG                                       65

CGGTCTGGAGTTCCTCCTCC                                       66

GGAGTTCCTCCTCCGTGAGC                                       67

TGCAGCAGGGAGCGGTCCAG                                       68

AGCAGCGTCAGGACCATGGG                                       69

GAACCTCTTGCGGGTGATGC                                       70

AAACCAGGCGTTTCAGGCTC                                       71

GAAACCAGGCGTTTCAGGCT                                       72

AGAACCTCTTGCGGGTGATG                                       73

AAGAACCTCTTGCGGGTGAT                                       74

CCCTAAAGAACCTCTTGCGG                                       75

TCCCTAAAGAACCTCTTGCG                                       76

CCTAAAGAACCTCTTGCGGG                                       77

CTAAAGAACCTCTTGCGGGT                                       78

TAAAGAACCTCTTGCGGGTG                                       79
```

-continued

| | |
|---|---|
| GCCCACGGCCGGCAGCAGCC | 80 |
| GCGGTGCAGCAGGGAGCGGT | 81 |
| CCACGGCCGGCAGCAGCCAG | 82 |
| CACGGCCGGCAGCAGCCAGG | 83 |
| CGGTGCAGCAGGGAGCGGTC | 84 |
| CACGCGGTGCAGCAGGGAGC | 85 |
| AGCGTCAGGACCATGGGCGC | 86 |
| GACACGCGGTGCAGCAGGGA | 87 |
| GCCCCGATGCACTGCGCCTC | 88 |
| CCCCGATGCACTGCGCCTCC | 89 |
| GCCCGTGCCACCGCCCCCAT | 90 |
| TTCCTCCTCCGTGAGCCGCA | 91 |
| TCCTCCTCCGTGAGCCGCAG | 92 |
| AGCCCCGATGCACTGCGCCT | 93 |
| CCTCCTCCGTGAGCCGCAGA | 94 |
| CCCACGGCCGGCAGCAGCCA | 95 |
| ACGGCCGGCAGCAGCCAGGC | 96 |
| CAGCGTCAGGACCATGGGCG | 97 |
| ACACGCGGTGCAGCAGGGAG | 98 |
| TAGGTGTACTGGCGGAAGCG | 99 |
| GGGTCCAGGCTGCCCAGCCA | 100 |
| GTCCAGGCTGCCCAGCCAGT | 101 |
| GGTCCAGGCTGCCCAGCCAG | 102 |
| GTCCAGGCTGCCCTGCTTGT | 103 |
| TCCAGGCTGCCCTGCTTGTC | 104 |
| CCATGGGTGCAGCACCCTCC | 105 |
| GGTCTTGCCTTGCAGGCTCT | 106 |
| CCTGTCTGAGGCTGCCTTCC | 107 |
| AGGCCTCCTCCACCAGTTGG | 108 |
| ACTGAGCAGGGACCCTCCCC | 109 |
| CCCCACTGGGTTTGCCACCA | 110 |
| CAGCCTGCATGTCCTCAGGC | 111 |
| TCCTGTCTGAGGCTGCCTTC | 112 |
| TGGTCTTGCCTTGCAGGCTC | 113 |
| GTCTTGCCTTGCAGGCTCTT | 114 |
| CAGGCTGCCCTGCTTGTCAT | 115 |
| GGGTACCAGGCAAGGGTGCC | 116 |
| GCATGTCCTCAGGCAGGACC | 117 |
| CAGGAGGCTCCTGTGCACCA | 118 |
| GCACAGACCCTGGGCTACCT | 119 |

-continued

| | |
|---|---|
| ACAGGAGGCTCCTGTGCACC | 120 |
| TTCCTGTCTGAGGCTGCCTT | 121 |
| TTGGTCTTGCCTTGCAGGCT | 122 |
| CTTGGTCTTGCCTTGCAGGC | 123 |
| AGGAGGCTCCTGTGCACCAG | 124 |
| GCACTTGTCCAGTGCTCCAG | 125 |
| GCTCCTGTGCACCAGCAAGT | 126 |
| CCCACTGGGTTTGCCACCAG | 127 |
| GAGGTGGGCCATGAGGGTGG | 128 |
| GGAGGTGGGCCATGAGGGTG | 129 |
| TGGAGGTGGGCCATGAGGGT | 130 |
| CCACTGGGTTTGCCACCAGT | 131 |
| TGCACTTGTCCAGTGCTCCA | 132 |
| CCTTGGTCTTGCCTTGCAGG | 133 |
| GATGGCACTCATCCCTGGCT | 134 |
| GCCCAGACCCAGGCCCAAAC | 135 |
| CAGGCTCTTGATGGCAGCCT | 136 |
| GGCTCCTGTGCACCAGCAAG | 137 |
| AGGCTCCTGTGCACCAGCAA | 138 |
| ACAGCCTGCATGTCCTCAGG | 139 |
| TGCCCAGACCCAGGCCCAAA | 140 |
| GCATGCACTTGTCCAGTGCT | 141 |
| CATGTCCTCAGGCAGGACCT | 142 |
| ATGCACTTGTCCAGTGCTCC | 143 |
| CCCAGGCCCTTGCTCAGAAT | 144 |
| GGCCAGACCAGGAAGGAGCC | 145 |
| CACAGACCCTGGGCTACCTC | 146 |
| CTGGTGTCAGAGCCTGCAGA | 147 |
| AGGGTACCAGGCAAGGGTGC | 148 |
| GGCCCAAACAGGAGGCTCCT | 149 |
| AGAGCCTGCAGATGAGTCCC | 150 |
| ATGGCACTCATCCCTGGCTG | 151 |
| TCTTGCCTTGCAGGCTCTTG | 152 |
| AACTGAGCAGGGACCCTCCC | 153 |
| CCTTGCAGGCTCTTGATGGC | 154 |
| GCCTTGCAGGCTCTTGATGG | 155 |
| TCCTGTGCACCAGCAAGTGC | 156 |
| TGCAGGCTCTTGATGGCAGC | 157 |
| GCCATGATGGCACTCATCCC | 158 |

-continued

| | |
|---|---|
| GCCAGACCAGGAAGGAGCCT | 159 |
| CTTGCCTTGCAGGCTCTTGA | 160 |
| GTGCACCAGCAAGTGCAGCA | 161 |
| TCCACAGAGCTGCAGGTTCT | 162 |
| ACTGGTGTCAGAGCCTGCAG | 163 |
| TGATGGCACTCATCCCTGGC | 164 |
| CACAGCCTGCATGTCCTCAG | 165 |
| GGGCCAGACCAGGAAGGAGC | 166 |
| TGCATGTCCTCAGGCAGGAC | 167 |
| CCTGTGCACCAGCAAGTGCA | 168 |
| GCCTGGGTTTATTGGAGGGT | 169 |
| CCTCTTTCCACAGAGCTGCA | 170 |
| GGGTGCAGCACCCTCCAAAC | 171 |
| GGTTTGCCACCAGTACAGGG | 172 |
| GGGTTTGCCACCAGTACAGG | 173 |
| GCCAGCACAGCCAAGAGTGG | 174 |
| GGCCAGCACAGCCAAGAGTG | 175 |
| TGGCCAGCACAGCCAAGAGT | 176 |
| AGGCCCAAACAGGAGGCTCC | 177 |
| GAACTTGCCTGCTTCCAGCT | 178 |
| GGGCACCCATGACACTCTGG | 179 |
| AAGCACAGCCTGCATGTCCT | 180 |
| GCAGCACCCTCCAAACTGGT | 181 |
| GGTGCAGCACCCTCCAAACT | 182 |
| CCCTCTGAACCCAGTGGAGG | 183 |
| TGTGCACCAGCAAGTGCAGC | 184 |
| CTTTCCACAGAGCTGCAGGT | 185 |
| GGTGTCAGAGCCTGCAGATG | 186 |
| TGGTGTCAGAGCCTGCAGAT | 187 |
| CCAGGCCCAAACAGGAGGCT | 188 |
| AGTGTAGCATTTCTCTGGCC | 189 |
| ACAGAGCTGCAGGTTCTGTC | 190 |
| CATGCACTTGTCCAGTGCTC | 191 |
| TTCCACAGAGCTGCAGGTTC | 192 |
| GAACTGAGCAGGGACCCTCC | 193 |
| CTGGGTTTGCCACCAGTACA | 194 |
| CACTGGGTTTGCCACCAGTA | 195 |
| GTGCAGCAAAGCTGGCTGCA | 196 |
| AACTTGCCTGCTTCCAGCTT | 197 |
| TTGCCTTGCAGGCTCTTGAT | 198 |

-continued

| | |
|---|---|
| GCACCCTCCAAACTGGTGTC | 199 |
| CCACAGAGCTGCAGGTTCTG | 200 |
| GCCTGAGGCACAGCACCAAG | 201 |
| GCCCAAACAGGAGGCTCCTG | 202 |
| CAGAGCCTGCAGATGAGTCC | 203 |
| CCATGATGGCACTCATCCCT | 204 |
| CTCCTGTGCACCAGCAAGTG | 205 |
| GAAGAGCCCAGGTTGTCTCA | 206 |
| CTTGCAGGCTCTTGATGGCA | 207 |
| GGCACCCATGACACTCTGGA | 208 |
| GTCAGAGCCTGCAGATGAGT | 209 |
| TCAGGACTTTGCCTCTTTCC | 210 |
| ACAGACTCTGGCAGGGAGGG | 211 |
| ACTGGGTTTGCCACCAGTAC | 212 |
| GGAAGTCACAGCAGGGCTGG | 213 |
| TGCCTTGCAGGCTCTTGATG | 214 |
| CCAGCACAGCCAAGAGTGGG | 215 |
| GGACTTTGCCTCTTTCCACA | 216 |
| GCTGCTTTTACTGCCATGGG | 217 |
| AGTGCAGCAAAGCTGGCTGC | 218 |
| GTGTCAGAGCCTGCAGATGA | 219 |
| CAGGACTTTGCCTCTTTCCA | 220 |
| GGCACAGCACCAAGGCATGG | 221 |
| GGGAATGCAGAACCACCCCC | 222 |
| CCAGGCCCTTGCTCAGAATA | 223 |
| CTGAGGCACAGCACCAAGGC | 224 |
| AACAGGAGGCTCCTGTGCAC | 225 |
| AGAAGAGCCCAGGTTGTCTC | 226 |
| TTTCCACAGAGCTGCAGGTT | 227 |
| TGCCTTTTCAGGACTTTGCC | 228 |
| AGCCATGATGGCACTCATCC | 229 |
| TCTTTCCACAGAGCTGCAGG | 230 |
| AGCACCCTCCAAACTGGTGT | 231 |
| AAGAGCCCAGGTTGTCTCAG | 232 |
| CAGGCCCAAACAGGAGGCTC | 233 |
| CCTCCACCAGTTGGAAGACC | 234 |
| ACCCAGGCCCAAACAGGAGG | 235 |
| CCTCTGAACCCAGTGGAGGA | 236 |
| AGGACTTTGCCTCTTTCCAC | 237 |

-continued

| | |
|---|---|
| TCCCTCTCCAGATACTGAGG | 238 |
| TGGGTTTGCCACCAGTACAG | 239 |
| CAGAATACAGTGCCCAGGCC | 240 |
| TAAGCACAGCCTGCATGTCC | 241 |
| CCTGAGGCACAGCACCAAGG | 242 |
| CCTTTTCAGGACTTTGCCTC | 243 |
| AGCCTGGGTTTATTGGAGGG | 244 |
| CTGTGCACCAGCAAGTGCAG | 245 |
| GAGGCACAGCACCAAGGCAT | 246 |
| CCAGACCCAGGCCCAAACAG | 247 |
| GGCCAAGACAGACTCTGGCA | 248 |
| GTGCAGCACCTCCAAACTG | 249 |
| CCCTCTCCAGATACTGAGGA | 250 |
| GCCTGGGCATTGCCTTAATT | 251 |
| TGAGGCACAGCACCAAGGCA | 252 |
| CTCTTTCCACAGAGCTGCAG | 253 |
| GTAAGCACAGCCTGCATGTC | 254 |
| CTCCTTATGCACCCAATCCT | 255 |
| AATGCAGAACCACCCCCACC | 256 |
| GCCCAGCCTCAGAATGATTC | 257 |
| TTGCAGGCTCTTGATGGCAG | 258 |
| GCCCCAAACCTGGAGTGAGA | 259 |
| GAGTGGAAGGAAGGAGCCCC | 260 |
| GAGTGTAGCATTTCTCTGGC | 261 |
| TCAGAGCCTGCAGATGAGTC | 262 |
| TCTCCTTATGCACCCAATCC | 263 |
| GGAATGCAGAACCACCCCCA | 264 |
| AGTGGAAGGAAGGAGCCCCA | 265 |
| CCCAATCCTTGCAGTCATGG | 266 |
| ATGATGGCACTCATCCCTGG | 267 |
| TGCAGCACCTCCAAACTGG | 268 |
| GACCCAGGCCCAAACAGGAG | 269 |
| AGACCCAGGCCCAAACAGGA | 270 |
| GTCTCCAGAACTGAGCAGGG | 271 |
| TGGTTAGGTTGGACCCATGG | 272 |
| GAAGGGTACCAGGCAAGGGT | 273 |
| CAGACCCAGGCCCAAACAGG | 274 |
| GCACCCATGACACTCTGGAT | 275 |
| ACTTTGCCTCTTTCCACAGA | 276 |
| GACTTTGCCTCTTTCCACAG | 277 |

-continued

| AGCCCCAAACCTGGAGTGAG | 278 |
| CACCCAATCCTTGCAGTCAT | 279 |
| CTCCACCAGTTGGAAGACCT | 280 |
| CACCCTCCAAACTGGTGTCA | 281 |
| AGAACTGAGCAGGGACCCTC | 282 |
| TGGCCAAGACAGACTCTGGC | 283 |
| GGAGTGGAAGGAAGGAGCCC | 284 |
| CTGAACCCAGTGGAGGAGGG | 285 |
| CCCTCCAAACTGGTGTCAGA | 286 |
| AGGCACAGCACCAAGGCATG | 287 |
| CTTTGCCTCTTTCCACAGAG | 288 |
| GCCCTTGCTCAGAATACAGT | 289 |
| CTGGTTAGGTTGGACCCATG | 290 |
| TGGAAGTCACAGCAGGGCTG | 291 |
| AGCCCAGCCTCAGAATGATT | 292 |
| AGTAAGCACAGCCTGCATGT | 293 |
| TCCACCAGTTGGAAGACCTC | 294 |
| TCCTCCACCAGTTGGAAGAC | 295 |
| CAGCACCCTCCAAACTGGTG | 296 |
| TGGCAAAGGTGATGCAGGCC | 297 |
| GTGCCATTGGTAGAGTAGGA | 298 |
| TCCTTATGCACCCAATCCTT | 299 |
| GAGCCATGATGGCACTCATC | 300 |
| CAGAACTGAGCAGGGACCCT | 301 |
| GGAAGGAGCCCCAAACCTGG | 302 |
| GTGATTACAGGGCAAGGCCA | 303 |
| TCAGAATACAGTGCCCAGGC | 304 |
| GGCATTGCCTTAATTCCTGT | 305 |
| TGCACCAGCAAGTGCAGCAA | 306 |
| TTCCCTCTCCAGATACTGAG | 307 |
| TTCAGGACTTTGCCTCTTTC | 308 |
| GCAAGTGCAGCAAAGCTGGC | 309 |
| TCCAGAACTGAGCAGGGACC | 310 |
| CATGATGGCACTCATCCCTG | 311 |
| ACCCTCCAAACTGGTGTCAG | 312 |
| CCAAACTGGTGTCAGAGCCT | 313 |
| AGGGAATGCAGAACCACCCC | 314 |
| GGCCCTTGCTCAGAATACAG | 315 |
| AGGCCCTTGCTCAGAATACA | 316 |

-continued

| | |
|---|---|
| CAGGCCCTTGCTCAGAATAC | 317 |
| AAACAGGAGGCTCCTGTGCA | 318 |
| GGAGTGTAGCATTTCTCTGG | 319 |
| GGGAGTGTAGCATTTCTCTG | 320 |
| GAATGCAGAACCACCCCCAC | 321 |
| TGTCAGAGCCTGCAGATGAG | 322 |
| TCTGAACCCAGTGGAGGAGG | 323 |
| AGACAGACTCTGGCAGGGAG | 324 |
| GCCAAGACAGACTCTGGCAG | 325 |
| GCTCAGAATACAGTGCCCAG | 326 |
| GGGAGTGGAAGGAAGGAGCC | 327 |
| TAGCCCAGCCTCAGAATGAT | 328 |
| ATAGCCCAGCCTCAGAATGA | 329 |
| TCCAAACTGGTGTCAGAGCC | 330 |
| ACCCAATCCTTGCAGTCATG | 331 |
| CCCAGCCTCAGAATGATTCT | 332 |
| CCTTAATTCCTGTCTGAGGC | 333 |
| GCCTTAATTCCTGTCTGAGG | 334 |
| AGTGATTACAGGGCAAGGCC | 335 |
| CCTGGGCATTGCCTTAATTC | 336 |
| TTGCCTTTTCAGGACTTTGC | 337 |
| CTTATGCACCCAATCCTTGC | 338 |
| AGTGCCATTGGTAGAGTAGG | 339 |
| CCAAACAGGAGGCTCCTGTG | 340 |
| AAACTGGTGTCAGAGCCTGC | 341 |
| TCTCCAGAACTGAGCAGGGA | 342 |
| AGACAACCCAATGGCAGGGC | 343 |
| GAAGGAGCCCCAAACCTGGA | 344 |
| GTGGAAGGAAGGAGCCCCAA | 345 |
| GCATTGCCTTAATTCCTGTC | 346 |
| CTCTGAACCCAGTGGAGGAG | 347 |
| AGAGCCATGATGGCACTCAT | 348 |
| GATTACAGGGCAAGGCCACA | 349 |
| GCACTGAGTGATTACAGGGC | 350 |
| CCTTATGCACCCAATCCTTG | 351 |
| TTTCAGGACTTTGCCTCTTT | 352 |
| CTTAGTGCCATTGGTAGAGT | 353 |
| AAGAAGAGCCCAGGTTGTCT | 354 |
| TTATGCACCCAATCCTTGCA | 355 |
| CTGGCCAAGACAGACTCTGG | 356 |

-continued

| | |
|---|---|
| TTGCTCAGAATACAGTGCCC | 357 |
| TATGCACCCAATCCTTGCAG | 358 |
| TGTCTCCAGAACTGAGCAGG | 359 |
| CCAGCAAGTGCAGCAAAGCT | 360 |
| CTCCAGAACTGAGCAGGGAC | 361 |
| AAGGAGCCCCAAACCTGGAG | 362 |
| AGGAAGGAGCCCCAAACCTG | 363 |
| ACAATCTCCTTATGCACCCA | 364 |
| CACAATCTCCTTATGCACCC | 365 |
| AGAAGGGTACCAGGCAAGGG | 366 |
| CCAAGACAGACTCTGGCAGG | 367 |
| CTCAGAATACAGTGCCCAGG | 368 |
| ATCTCCTTATGCACCCAATC | 369 |
| GCACCAGCAAGTGCAGCAAA | 370 |
| CTCCAAACTGGTGTCAGAGC | 371 |
| CAAGTGCAGCAAAGCTGGCT | 372 |
| AAGGAAGTCAGAGGGAGGGC | 373 |
| CTTAATTCCTGTCTGAGGCT | 374 |
| TGATTACAGGGCAAGGCCAC | 375 |
| GCTTTAGAGATTTGCTACCC | 376 |
| CCAGCTTCTCCACATCAATG | 377 |
| CCAGCCTCAGAATGATTCTC | 378 |
| CCTCCAAACTGGTGTCAGAG | 379 |
| GGCACTGAGTGATTACAGGG | 380 |
| GGGCACTGAGTGATTACAGG | 381 |
| TTGGCAAAGGTGATGCAGGC | 382 |
| AAGACAGACTCTGGCAGGGA | 383 |
| ACCAGCAAGTGCAGCAAAGC | 384 |
| GCCCTGGATGTGGCAAAAGA | 385 |
| GAGTGATTACAGGGCAAGGC | 386 |
| GACTTAGTGCCATTGGTAGA | 387 |
| CAAGACAGACTCTGGCAGGG | 388 |
| ACCCATGACACTCTGGATGA | 389 |
| GAGAAGGGTACCAGGCAAGG | 390 |
| CACCCATGACACTCTGGATG | 391 |
| CATTGCCTTAATTCCTGTCT | 392 |
| CTTGCTCAGAATACAGTGCC | 393 |
| CCTTGCTCAGAATACAGTGC | 394 |
| CCCATGACACTCTGGATGAG | 395 |

-continued

```
ACTGGCCAAGACAGACTCTG                                     396

AAGTGCAGCAAAGCTGGCTG                                     397

CAGACAACCCAATGGCAGGG                                     398

AAGGAAGGAGCCCCAAACCT                                     399

GCCTCAGAATGATTCTCAGG                                     400

CCCTTGCTCAGAATACAGTG                                     401

CAAACTGGTGTCAGAGCCTG                                     402

GTTGGCAAAGGTGATGCAGG                                     403

GGTTGGCAAAGGTGATGCAG                                     404

TAAGAAGAGCCCAGGTTGTC                                     405

TCACAATCTCCTTATGCACC                                     406

CCTCTCCAGATACTGAGGAA                                     407

AGCAAGTGCAGCAAAGCTGG                                     408

TTAGTGCCATTGGTAGAGTA                                     409

ACTTAGTGCCATTGGTAGAG                                     410

TAGTGCCATTGGTAGAGTAG                                     411

GAAGGAAGGAGCCCCAAACC                                     412

GGTAGAGTAGGAAACCAGGC                                     413

CACTGAGTGATTACAGGGCA                                     414

GAGAGAAGGGTACCAGGCAA                                     415

CAATCTCCTTATGCACCCAA                                     416

GCTGTTCCTTCAGAAAGGAC                                     417

GTCACAATCTCCTTATGCAC                                     418

TTTGCCTTTTCAGGACTTTG                                     419

ACACTCTGGATGAGTTTGTC                                     420

AGCTGTTCCTTCAGAAAGGA                                     421

CTTTAGAGATTTGCTACCCT                                     422

CAGCTTCTCCACATCAATGA                                     423

GACACTCTGGATGAGTTTGT                                     424

AAGTAAGCACAGCCTGCATG                                     425

CAGCCTCAGAATGATTCTCA                                     426

GGAAGGAAGGAGCCCCAAAC                                     427

AGGGCACTGAGTGATTACAG                                     428

TGCCATTGGTAGAGTAGGAA                                     429

CAAGGAAGTCAGAGGGAGGG                                     430

AGAGAAGGGTACCAGGCAAG                                     431

ACAGACAACCCAATGGCAGG                                     432

AAGGGAATGCAGAACCACCC                                     433

AATCTCCTTATGCACCCAAT                                     434

GCAGGAAGTTGTAAGTGCAG                                     435
```

AGGAAGTTGTAAGTGCAGGG                                                436

AGCCTCAGAATGATTCTCAG                                                437

TTTAGAGATTTGCTACCCTT                                                438

TGCTTTAGAGATTTGCTACC                                                439

GAGACAGACAACCCAATGGC                                                440

GACAGACAACCCAATGGCAG                                                441

AGACAGACAACCCAATGGCA                                                442

AAAGTAAGCACAGCCTGCAT                                                443

CATGACACTCTGGATGAGTT                                                444

TGAGTGATTACAGGGCAAGG                                                445

GCCATTGGTAGAGTAGGAAA                                                446

CAGGAAGTTGTAAGTGCAGG                                                447

ACTGAGTGATTACAGGGCAA                                                448

GGTAGCTGATGAAGACATCT                                                449

GAAGGGAATGCAGAACCACC                                                450

GCTTCTCCACATCAATGAAG                                                451

AGCTTCTCCACATCAATGAA                                                452

ATGACACTCTGGATGAGTTT                                                453

TGACACTCTGGATGAGTTTG                                                454

TGGTAGAGTAGGAAACCAGG                                                455

TTTTGGGAAAGAGGGACCC                                                 456

GTTTTGGGAAAGAGGGACC                                                 457

CTCTCCAGATACTGAGGAAA                                                458

CTCCAGATACTGAGGAAAGT                                                459

GCTTAAAGCAGTCACAATCT                                                460

GTAGCTGATGAAGACATCTG                                                461

GGTTTTGGGAAAGAGGGAC                                                 462

TTGAAAGTAAGCACAGCCTG                                                463

CCAGATACTGAGGAAAGTGG                                                464

TTGGTAGAGTAGGAAACCAG                                                465

CCTGGATGTGGCAAAAGATA                                                466

GGATGTGGCAAAAGATACCA                                                467

TAGCTGATGAAGACATCTGG                                                468

ATTGGTAGAGTAGGAAACCA                                                469

CATTGGTAGAGTAGGAAACC                                                470

CCATTGGTAGAGTAGGAAAC                                                471

TCTCCACATCAATGAAGACA                                                472

TCTCCAGATACTGAGGAAAG                                                473

AGCTTAAAGCAGTCACAATC                                                474

-continued

| | |
|---|---|
| CAGCTTAAAGCAGTCACAAT | 475 |
| TCCAGATACTGAGGAAAGTG | 476 |
| CAGATACTGAGGAAAGTGGG | 477 |
| TGGATGTGGCAAAAGATACC | 478 |
| TCCACATCAATGAAGACACT | 479 |
| CTCCACATCAATGAAGACAC | 480 |
| TTCTCCACATCAATGAAGAC | 481 |
| TGTGGCAAAAGATACCACAC | 482 |
| GATGTGGCAAAAGATACCAC | 483 |
| ATGTGGCAAAAGATACCACA | 484 |
| TCTTTGAAGCAAGGGAGAAG | 485 |
| CCACATCAATGAAGACACTG | 486 |
| CACATCAATGAAGACACTGA | 487 |
| ACATCAATGAAGACACTGAA | 488 |
| AGCCATCAATGATGGGCACA | 489 |
| GATGGGCACAATGTTCTTGC | 490 |
| GCCATCAATGATGGGCACAA | 491 |
| ATGATGGGCACAATGTTCTT | 492 |
| TGATGGGCACAATGTTCTTG | 493 |
| CCATCAATGATGGGCACAAT | 494 |
| AATGATGGGCACAATGTTCT | 495 |
| CAATGATGGGCACAATGTTC | 496 |
| TCAATGATGGGCACAATGTT | 497 |
| ATCAATGATGGGCACAATGT | 498 |
| CATCAATGATGGGCACAATG | 499 |
| ATGGGCACAATGTTCTTGCC | 500 |
| CTCAATGGTGGCCTCCTGGT | 501 |
| ATGGTGGCCTCCTGGTATTC | 502 |
| TCAATGGTGGCCTCCTGGTA | 503 |
| CACCTTCAGGAGACTGGCCA | 504 |
| TGCACCTTCAGGAGACTGGC | 505 |
| GTGCACCTTCAGGAGACTGG | 506 |
| GAAGCCATCAATGATGGGCA | 507 |
| ACATCTGGAGTGTCCCCACT | 508 |
| CCTTGCAGTCATGGTCTTGC | 509 |
| GACATCTGGAGTGTCCCCAC | 510 |
| CATCTGGAGTGTCCCCACTG | 511 |
| AGACATCTGGAGTGTCCCCA | 512 |
| GCAGTCATGGTCTTGCATGC | 513 |
| TCCTTGCAGTCATGGTCTTG | 514 |

-continued

| | |
|---|---|
| AAGACATCTGGAGTGTCCCC | 515 |
| GCTGAACACCTTGGTCTTGC | 516 |
| CTGAACACCTTGGTCTTGCC | 517 |
| ATGATCTTCTCAATGGTGGC | 518 |
| GATGATCTTCTCAATGGTGG | 519 |
| GGATGATCTTCTCAATGGTG | 520 |
| GCAGCTTAAAGCAGTCACAA | 521 |
| TCTGGAGTGTCCCCACTGGG | 522 |
| ATCTGGAGTGTCCCCACTGG | 523 |
| CAATGGTGGCCTCCTGGTAT | 524 |
| AATGGTGGCCTCCTGGTATT | 525 |
| CTGATGAAGACATCTGGAGT | 526 |
| ATCCTTGCAGTCATGGTCTT | 527 |
| GAACACCTTGGTCTTGCCTT | 528 |
| TGAACACCTTGGTCTTGCCT | 529 |
| AATCCTTGCAGTCATGGTCT | 530 |
| AACACCTTGGTCTTGCCTTG | 531 |
| GAAGACATCTGGAGTGTCCC | 532 |
| TCAGACACTGTATTGTTATT | 533 |
| CAGACACTGTATTGTTATTG | 534 |
| GACACTGAAGCCATGCAGCT | 535 |
| ACACTGAAGCCATGCAGCTG | 536 |
| AGACACTGAAGCCATGCAGC | 537 |
| CTCTGGATGAGTTTGTCCTC | 538 |
| CTGGAGTGTCCCCACTGGGT | 539 |
| GGAGTGTCCCCACTGGGTTT | 540 |
| TGGAGTGTCCCCACTGGGTT | 541 |
| GAGTGTCCCCACTGGGTTTG | 542 |
| CACCTTGGTCTTGCCTTGCA | 543 |
| ACACCTTGGTCTTGCCTTGC | 544 |
| TTGACTTTCTGATGATGTGG | 545 |
| ACTCTGGATGAGTTTGTCCT | 546 |
| CACTCTGGATGAGTTTGTCC | 547 |
| GCAGGTTCTGTCTAGGCTGC | 548 |
| GCTGCAGGTTCTGTCTAGGC | 549 |
| CAGGTTCTGTCTAGGCTGCT | 550 |
| CTGCAGGTTCTGTCTAGGCT | 551 |
| TGCAGGTTCTGTCTAGGCTG | 552 |
| AACCCAATGGCAGGGCCTGG | 553 |

-continued

| | |
|---|---|
| CAACCCAATGGCAGGGCCTG | 554 |
| GTGTCTCCAGAACTGAGCAG | 555 |
| GGGCTGCCTGGTCCCTGAGT | 556 |
| GGCTGCCTGGTCCCTGAGTA | 557 |
| GCCTGACTTCCCTTCCCTCT | 558 |
| GTCCTGTGAGGGCAGTGTCC | 559 |
| ACTCATCCCTGGCTGGCTCC | 560 |
| GTGAGGGCAGTGTCCAGGCT | 561 |
| GTGGGTAGCCCTGGATGGCT | 562 |
| GTATGGCCTCTGGGTCAGCT | 563 |
| AGTGGGTTGGAGGTGGGCCA | 564 |
| GTGGGTTGGAGGTGGGCCAT | 565 |
| TGTGAGGGCAGTGTCCAGGC | 566 |
| GGGTAGCCCTGGATGGCTGA | 567 |
| CCCCAACTCCAGTGTCTCCA | 568 |
| GTTGTCTCAGCCCAGGGAGA | 569 |
| CTGTCCTGTGAGGGCAGTGT | 570 |
| CCCAGATGCAGGGAGTGGGC | 571 |
| TGTCCTGTGAGGGCAGTGTC | 572 |
| CCTGTGAGGGCAGTGTCCAG | 573 |
| ATGGCCTCTGGGTCAGCTTT | 574 |
| GCTGCCTGGTCCCTGAGTAA | 575 |
| TGCAGGCCCAGATGCAGGGA | 576 |
| GGGTTGGAGGTGGGCCATGA | 577 |
| GGCTGCCCTGCTTGTCATAT | 578 |
| TGGGTAGCCCTGGATGGCTG | 579 |
| CTGTGAGGGCAGTGTCCAGG | 580 |
| AAGCCTGACTTCCCTTCCCT | 581 |
| GGTGATGCAGGCCCAGATGC | 582 |
| TATGGCCTCTGGGTCAGCTT | 583 |
| TGTCCAGTGCTCCAGGTGAT | 584 |
| GCTGCCCTGCTTGTCATATC | 585 |
| AAGTGGGTTGGAGGTGGGCC | 586 |
| GTAGCCCTGGATGGCTGAGG | 587 |
| ATGCAGGCCCAGATGCAGGG | 588 |
| GTCCAGTGCTCCAGGTGATA | 589 |
| CAAGCCTGACTTCCCTTCCC | 590 |
| CCAAGCCTGACTTCCCTTCC | 591 |
| TGCCTGGTCCCTGAGTAAGC | 592 |
| GCCTGGAGCCTGGGTTTATT | 593 |

-continued

| | |
|---|---|
| AGGCCCAGATGCAGGGAGTG | 594 |
| GTGCTCCAGGTGATAGCACC | 595 |
| TGGGTTGGAGGTGGGCCATG | 596 |
| GGTTCTGTCTAGGCTGCTTT | 597 |
| AGGTTCTGTCTAGGCTGCTT | 598 |
| CTGCCCTGCTTGTCATATCC | 599 |
| AAGCAGTGGGTAGCCCTGGA | 600 |
| GTGATGCAGGCCCAGATGCA | 601 |
| TTGTCTCAGCCCAGGGAGAC | 602 |
| CCCAACTCCAGTGTCTCCAG | 603 |
| GTTGGAGGTGGGCCATGAGG | 604 |
| GGTTGGAGGTGGGCCATGAG | 605 |
| CAGAGCTGCAGGTTCTGTCT | 606 |
| GATGCAGGCCCAGATGCAGG | 607 |
| GCTTGTCATATCCATGCCCT | 608 |
| GCCCTGCTTGTCATATCCAT | 609 |
| GGCTGGCACTGGCCAAGACA | 610 |
| TGCCCTGCTTGTCATATCCA | 611 |
| AGCTGCAGGTTCTGTCTAGG | 612 |
| TTGGAGGTGGGCCATGAGGG | 613 |
| AGAATACAGTGCCCAGGCCC | 614 |
| AGGCTGGCACTGGCCAAGAC | 615 |
| GTTTCAGGAGCTGTTCCTTC | 616 |
| CTGCCTGGTCCCTGAGTAAG | 617 |
| TGCTCCAGGTGATAGCACCA | 618 |
| CCCTTTGCCTTTTCAGGACT | 619 |
| GCAGCCAGCTTTAAGGTGTC | 620 |
| GGCAAAGGTGATGCAGGCCC | 621 |
| GTTCTGTCTAGGCTGCTTTT | 622 |
| GAGCTGCAGGTTCTGTCTAG | 623 |
| AGAGCTGCAGGTTCTGTCTA | 624 |
| GTCAGGCTAGCTAAGGGCAC | 625 |
| CCAACTCCAGTGTCTCCAGA | 626 |
| AGGTGATGCAGGCCCAGATG | 627 |
| TGCTTGTCATATCCATGCCC | 628 |
| AGTCAGGCTAGCTAAGGGCA | 629 |
| GCTGGCACTGGCCAAGACAG | 630 |
| AGTGCTCCAGGTGATAGCAC | 631 |
| TCAGGAGCTGTTCCTTCAGA | 632 |

-continued

| | |
|---|---|
| TCTAGGCTGCTTTTACTGCC | 633 |
| TGATGCAGGCCCAGATGCAG | 634 |
| ACAACCCAATGGCAGGGCCT | 635 |
| ACCCTTTGCCTTTTCAGGAC | 636 |
| ACCCTCTGAACCCAGTGGAG | 637 |
| GCAAAGGTGATGCAGGCCCA | 638 |
| GACTGGTTAGGTTGGACCCA | 639 |
| GTCTAGGCTGCTTTTACTGC | 640 |
| ACAGTCTGAGTGGAGAGCCA | 641 |
| CACAGTCTGAGTGGAGAGCC | 642 |
| GACAACCCAATGGCAGGGCC | 643 |
| AGGAAGTCAGAGGGAGGGCT | 644 |
| TCAGGCTAGCTAAGGGCACT | 645 |
| CCTGGAGCCTGGGTTTATTG | 646 |
| TCTTACCCTCTGAACCCAGT | 647 |
| GCACTTGTGCTGCATGAGGA | 648 |
| GGGTTTATTGGAGGGTGCTT | 649 |
| TTCAGGAGCTGTTCCTTCAG | 650 |
| TACCCTCTGAACCCAGTGGA | 651 |
| GGAGAGCCATGATGGCACTC | 652 |
| CTGCTTGTCATATCCATGCC | 653 |
| CCTGCTTGTCATATCCATGC | 654 |
| CAGTCTGAGTGGAGAGCCAT | 655 |
| ATCTGGGACTTAGTCAGGCT | 656 |
| TAGTCAGGCTAGCTAAGGGC | 657 |
| GTGGAGAGCCATGATGGCAC | 658 |
| GTCTGAGTGGAGAGCCATGA | 659 |
| GAGTGGAGAGCCATGATGGC | 660 |
| TGGGTTTATTGGAGGGTGCT | 661 |
| CTGGGTTTATTGGAGGGTGC | 662 |
| GTGAGCACTTGTGCTGCATG | 663 |
| AAGGTGATGCAGGCCCAGAT | 664 |
| GCTAGCTAAGGGCACTGAGT | 665 |
| GGCACAGTCTGAGTGGAGAG | 666 |
| AGGCACAGTCTGAGTGGAGA | 667 |
| AGTGGAGAGCCATGATGGCA | 668 |
| CCCTGCTTGTCATATCCATG | 669 |
| CTGGAGCCTGGGTTTATTGG | 670 |
| GGCACTGGCCAAGACAGACT | 671 |
| CAGGCACAGTCTGAGTGGAG | 672 |

-continued

| | |
|---|---|
| TTACCCTCTGAACCCAGTGG | 673 |
| AGCACTTGTGCTGCATGAGG | 674 |
| GATCTGGGACTTAGTCAGGC | 675 |
| GAGCCTGGGTTTATTGGAGG | 676 |
| GGAGCCTGGGTTTATTGGAG | 677 |
| CAGCCAGCTTTAAGGTGTCA | 678 |
| CCTGGGTTTATTGGAGGGTG | 679 |
| ATGGAAGTCACAGCAGGGCT | 680 |
| CTCCAGTGTCTCCAGAACTG | 681 |
| GGCTAGCTAAGGGCACTGAG | 682 |
| AGGCTAGCTAAGGGCACTGA | 683 |
| GGAGAGAAGGGTACCAGGCA | 684 |
| TGGAGCCTGGGTTTATTGGA | 685 |
| GAGAGCCATGATGGCACTCA | 686 |
| CTTACCCTCTGAACCCAGTG | 687 |
| GCAAAGCTGGCTGCAGTGAC | 688 |
| CAGGCTAGCTAAGGGCACTG | 689 |
| AGTCTGAGTGGAGAGCCATG | 690 |
| CTGGCACTGGCCAAGACAGA | 691 |
| CTGTCTAGGCTGCTTTTACT | 692 |
| TGGAGAGCCATGATGGCACT | 693 |
| AGCAAAGCTGGCTGCAGTGA | 694 |
| GCACTGGCCAAGACAGACTC | 695 |
| AACCCTTTGCCTTTTCAGGA | 696 |
| CAGCAAAGCTGGCTGCAGTG | 697 |
| CAACCCTTTGCCTTTTCAGG | 698 |
| TCTGTCTAGGCTGCTTTTAC | 699 |
| GAGCACTTGTGCTGCATGAG | 700 |
| GGGCAATGGGATATTCCTGC | 701 |
| GGTTTATTGGAGGGTGCTTT | 702 |
| TTCTGTCTAGGCTGCTTTTA | 703 |
| TGAGCACTTGTGCTGCATGA | 704 |
| GTGACAACCCTTTGCCTTTT | 705 |
| TTCTTACCCTCTGAACCCAG | 706 |
| TGGAGAGAAGGGTACCAGGC | 707 |
| AGTGTCTCCAGAACTGAGCA | 708 |
| CAGTGTCTCCAGAACTGAGC | 709 |
| AAAGGTGATGCAGGCCCAGA | 710 |
| TGGCACTGGCCAAGACAGAC | 711 |

-continued

| | |
|---|---|
| GGCAATGGGATATTCCTGCT | 712 |
| CAAAGGTGATGCAGGCCCAG | 713 |
| GACAACCCTTTGCCTTTTCA | 714 |
| GTTGCAAAATCCTATCCCCC | 715 |
| CAGGAGCTGTTCCTTCAGAA | 716 |
| TCCTAAGAAGAGCCCAGGTT | 717 |
| TTCCTAAGAAGAGCCCAGGT | 718 |
| CCAGTGTCTCCAGAACTGAG | 719 |
| CCCAAACCTGGAGTGAGACC | 720 |
| GTTTATTGGAGGGTGCTTTC | 721 |
| CCTGGAGTGAGACCTTTGAC | 722 |
| GAGGGAGAGCCATTTCCTAA | 723 |
| TCTGAGTGGAGAGCCATGAT | 724 |
| GCAATGGGATATTCCTGCTC | 725 |
| TGTCTAGGCTGCTTTTACTG | 726 |
| ACAACCCTTTGCCTTTTCAG | 727 |
| GACTTTCTGATGATGTGGCC | 728 |
| CACTGGCCAAGACAGACTCT | 729 |
| TGACAACCCTTTGCCTTTTC | 730 |
| CAACTCCAGTGTCTCCAGAA | 731 |
| GCCAGCTTTAAGGTGTCAAC | 732 |
| CAAAGCTGGCTGCAGTGACA | 733 |
| AGCCAGCTTTAAGGTGTCAA | 734 |
| GCCATTTCCTAAGAAGAGCC | 735 |
| CCTAAGAAGAGCCCAGGTTG | 736 |
| TTATTGGAGGGTGCTTTCTT | 737 |
| TGAGTGGAGAGCCATGATGG | 738 |
| CCAAACCTGGAGTGAGACCT | 739 |
| CCATTTCCTAAGAAGAGCCC | 740 |
| CTGGAGTGAGACCTTTGACT | 741 |
| GCTGCAGTGACAAGGAAGTC | 742 |
| AAGCTGGCTGCAGTGACAAG | 743 |
| CTGAGTGGAGAGCCATGATG | 744 |
| TTTCCTAAGAAGAGCCCAGG | 745 |
| GGCAAAGATTTGTGAGGGCT | 746 |
| CACTTGTGCTGCATGAGGAA | 747 |
| CCTGGAGATACTCAGACACT | 748 |
| TGTTGCAAAATCCTATCCCC | 749 |
| TGGAGTGAGACCTTTGACTT | 750 |
| AGTGAGACCTTTGACTTTCT | 751 |

-continued

| | |
|---|---|
| AACCTGGAGTGAGACCTTTG | 752 |
| GCTGCATGAGGAAAGGAGGA | 753 |
| GTGAGACCTTTGACTTTCTG | 754 |
| CATTTCCTAAGAAGAGCCCA | 755 |
| AAAGCTGGCTGCAGTGACAA | 756 |
| TGACTTTCTGATGATGTGGC | 757 |
| AGCCATTTCCTAAGAAGAGC | 758 |
| CAAACCTGGAGTGAGACCTT | 759 |
| TGGCAAAGATTTGTGAGGGC | 760 |
| TGTGCTGCATGAGGAAAGGA | 761 |
| ATTTCCTAAGAAGAGCCCAG | 762 |
| CTGCAGTGACAAGGAAGTCA | 763 |
| GCAAAGATTTGTGAGGGCTT | 764 |
| GCAGTGACAAGGAAGTCAGA | 765 |
| GTGCTTTAGAGATTTGCTAC | 766 |
| AAACCTGGAGTGAGACCTTT | 767 |
| GGAATGGAGAGAAGGGTACC | 768 |
| TGAGACCTTTGACTTTCTGA | 769 |
| TGGAGATACTCAGACACTGT | 770 |
| TTGTGCTGCATGAGGAAAGG | 771 |
| TTGTTGCAAAATCCTATCCC | 772 |
| ACTTGTGCTGCATGAGGAAA | 773 |
| GGAGATACTCAGACACTGTA | 774 |
| GGAGACAGACAACCCAATGG | 775 |
| CTGCTAGATTCTTTGAAGCA | 776 |
| CTTGTGCTGCATGAGGAAAG | 777 |
| TGAGGAAAGGAGGATCAGGT | 778 |
| TGCAGTGACAAGGAAGTCAG | 779 |
| GTGGCAAAGATACCACACC | 780 |
| GCATGAGGAAAGGAGGATCA | 781 |
| GAGCCATTTCCTAAGAAGAG | 782 |
| AGAGCCATTTCCTAAGAAGA | 783 |
| GGAGAAGGGAATGCAGAACC | 784 |
| TCTCAGGAAAGCAATTCCAC | 785 |
| CAAAGATTTGTGAGGGCTTC | 786 |
| CTGCATGAGGAAAGGAGGAT | 787 |
| AATGGAGAGAAGGGTACCAG | 788 |
| AAATGGAAGTCACAGCAGGG | 789 |
| GATACTGAGGAAAGTGGGTT | 790 |

-continued

```
TGCATGAGGAAAGGAGGATC                              791

AGATACTGAGGAAAGTGGGT                              792

GAGATACTCAGACACTGTAT                              793

ATGGCAAAGATTTGTGAGGG                              794

ATTCTCAGGAAAGCAATTCC                              795

AGGAATGGAGAGAAGGGTAC                              796

GATTCTTTGAAGCAAGGGAG                              797

AGATTCTTTGAAGCAAGGGA                              798

GAAATGGAAGTCACAGCAGG                              799

GGAAATGGAAGTCACAGCAG                              800

TTTGTTGCAAAATCCTATCC                              801

ATGAGGAAAGGAGGATCAGG                              802

TGGAAATGGAAGTCACAGCA                              803

AGATACTCAGACACTGTATT                              804

GCTAGATTCTTTGAAGCAAG                              805

TGCTAGATTCTTTGAAGCAA                              806

AGGAGAAGGGAATGCAGAAC                              807

ATGGAAATGGAAGTCACAGC                              808

CATGAGGAAAGGAGGATCAG                              809

TAGATTCTTTGAAGCAAGGG                              810

TTCTTTGAAGCAAGGGAGAA                              811

GATTCTCAGGAAAGCAATTC                              812

CTAGATTCTTTGAAGCAAGG                              813

GAATGATTCTCAGGAAAGCA                              814

TTTTGTTGCAAAATCCTATC                              815

TGATTCTCAGGAAAGCAATT                              816

AGAATGATTCTCAGGAAAGC                              817

ATGATTCTCAGGAAAGCAAT                              818

AATGGCAAAGATTTGTGAGG                              819

GATGGAAATGGAAGTCACAG                              820

AATGATTCTCAGGAAAGCAA                              821

AAATGGCAAAGATTTGTGAG                              822

CTCAAGCTGACTGCTATCAG                              823

TCCTCAAGCTGACTGCTATC                              824

CCTCAAGCTGACTGCTATCA                              825

AGACACTGTATTGTTATTGG                              826

ATGGGATATTCCTGCTCTGT                              827

GATAGCACCAACACAAAGTT                              828

GCCCCCATCTGGCCCAGGCA                              829

AAGAGCCTTCAGCAGCCCCC                              830
```

-continued

| | |
|---|---|
| GCTGTCCTGTGAGGGCAGTG | 831 |
| AGTGGGTAGCCCTGGATGGC | 832 |
| TGTATGGCCTCTGGGTCAGC | 833 |
| GCCTGGTCCCTGAGTAAGCA | 834 |
| TGTCTCAGCCCAGGGAGACT | 835 |
| GGAGGGTGCTTTCTTACCCT | 836 |
| AGGGTGCTTTCTTACCCTCT | 837 |
| GGGTGCTTTCTTACCCTCTG | 838 |
| GAGGGTGCTTTCTTACCCTC | 839 |
| CCTCTGGGTCAGCTTTTTGT | 840 |
| AGTAAGCAGTGGGTAGCCCT | 841 |
| GGTTTCAGGAGCTGTTCCTT | 842 |
| GTAAGCAGTGGGTAGCCCTG | 843 |
| GAGTAAGCAGTGGGTAGCCC | 844 |
| GGTGCTTTCTTACCCTCTGA | 845 |
| TCCCTGAGTAAGCAGTGGGT | 846 |
| GTCCCTGAGTAAGCAGTGGG | 847 |
| GGTCCCTGAGTAAGCAGTGG | 848 |
| GGGACTTAGTCAGGCTAGCT | 849 |
| TAAGCAGTGGGTAGCCCTGG | 850 |
| GGTGAGCACTTGTGCTGCAT | 851 |
| CCTGGTCCCTGAGTAAGCAG | 852 |
| CTGGTCCCTGAGTAAGCAGT | 853 |
| GGGACTGGTTAGGTTGGACC | 854 |
| GGAGGGAGAGCCATTTCCTA | 855 |
| CCCTGAGTAAGCAGTGGGTA | 856 |
| TGGGACTTAGTCAGGCTAGC | 857 |
| GCTCCAGGTGATAGCACCAA | 858 |
| GGAAAGAGCCTTCAGCAGCC | 859 |
| TGGTCCCTGAGTAAGCAGTG | 860 |
| TGAGTAAGCAGTGGGTAGCC | 861 |
| TCTGGGACTTAGTCAGGCTA | 862 |
| GGACTTAGTCAGGCTAGCTA | 863 |
| GGGAAAGAGCCTTCAGCAGC | 864 |
| GTGCTTTCTTACCCTCTGAA | 865 |
| CTGGGACTTAGTCAGGCTAG | 866 |
| CTGAGTAAGCAGTGGGTAGC | 867 |
| AGTGACAACCCTTTGCCTTT | 868 |
| CCTGAGTAAGCAGTGGGTAG | 869 |

-continued

| | |
|---|---|
| AGAACTAGGAGTCACCTGGC | 870 |
| CTCCAGGTGATAGCACCAAC | 871 |
| ACTTTCTGATGATGTGGCCA | 872 |
| TCCAGGTGATAGCACCAACA | 873 |
| TTAGTCAGGCTAGCTAAGGG | 874 |
| ATTGGAGGGTGCTTTCTTAC | 875 |
| GTGGCCAAGAACTAGGAGTC | 876 |
| TGCTTTCTTACCCTCTGAAC | 877 |
| AAGTGACAACCCTTTGCCTT | 878 |
| CTTAGTCAGGCTAGCTAAGG | 879 |
| TATTGGAGGGTGCTTTCTTA | 880 |
| TAAGTGACAACCCTTTGCCT | 881 |
| CAATGGGATATTCCTGCTCT | 882 |
| GACTTAGTCAGGCTAGCTAA | 883 |
| TGTGGCCAAGAACTAGGAGT | 884 |
| GCTGCTAGATTCTTTGAAGC | 885 |
| CTTTCTGATGATGTGGCCAA | 886 |
| CCAGCTTTAAGGTGTCAACA | 887 |
| ACTTAGTCAGGCTAGCTAAG | 888 |
| AATGGGATATTCCTGCTCTG | 889 |
| TTCTGATGATGTGGCCAAGA | 890 |
| AGCTTTAAGGTGTCAACACC | 891 |
| GTGCTGCATGAGGAAAGGAG | 892 |
| GATGTGGCCAAGAACTAGGA | 893 |
| TTTCTGATGATGTGGCCAAG | 894 |
| GAGACCTTTGACTTTCTGAT | 895 |
| GACCTTTGACTTTCTGATGA | 896 |
| ATGTGGCCAAGAACTAGGAG | 897 |
| GACACTGTATTGTTATTGGC | 898 |
| AGACCTTTGACTTTCTGATG | 899 |
| CAGCTTTAAGGTGTCAACAC | 900 |
| ACCTTTGACTTTCTGATGAT | 901 |
| TAGCACCAACACAAAGTTGC | 902 |
| GGTGATAGCACCAACACAAA | 903 |
| TGATAGCACCAACACAAAGT | 904 |
| GTGATAGCACCAACACAAAG | 905 |
| CTTTTTGTTGCAAAATCCTA | 906 |
| ATAGCACCAACACAAAGTTG | 907 |
| TCAAGCTGACTGCTATCAGC | 908 |
| TCCATGCCCTGGCTCTGGCC | 909 |

-continued

| | |
|---|---|
| CTCAGCCCAGGGAGACTGGT | 910 |
| GTCTCAGCCCAGGGAGACTG | 911 |
| GGTGTCAACACCTGGCCCTT | 912 |
| TCAGCCCAGGGAGACTGGTT | 913 |
| TCTCAGCCCAGGGAGACTGG | 914 |
| TGTCATATCCATGCCCTGGC | 915 |
| CAGCCCAGGGAGACTGGTTT | 916 |
| TCCTCCTCAAGCTGACTGCT | 917 |
| AAAGAGCCTTCAGCAGCCCC | 918 |
| CTGGTTTCAGGAGCTGTTCC | 919 |
| AAGTCAGAGGGAGGGCTGGT | 920 |
| GAAAGAGCCTTCAGCAGCCC | 921 |
| CCTCCTCAAGCTGACTGCTA | 922 |
| CTGGGTCAGCTTTTTGTTGC | 923 |
| TTGTCATATCCATGCCCTGG | 924 |
| TCTGGGTCAGCTTTTTGTTG | 925 |
| GCCCTAAGTGACAACCCTTT | 926 |
| TGGGATATTCCTGCTCTGTA | 927 |
| CTCCTCAAGCTGACTGCTAT | 928 |
| GCCAAGAACTAGGAGTCACC | 929 |
| CTAAGTGACAACCCTTTGCC | 930 |
| CCTAAGTGACAACCCTTTGC | 931 |
| GCTTTAAGGTGTCAACACCT | 932 |
| GGCCAAGAACTAGGAGTCAC | 933 |
| CCCTAAGTGACAACCCTTTG | 934 |
| TGGCCAAGAACTAGGAGTCA | 935 |
| CCAAGAACTAGGAGTCACCT | 936 |
| GCAGGAGAAGGGAATGCAGA | 937 |
| AAGAACTAGGAGTCACCTGG | 938 |
| TTTAAGGTGTCAACACCTGG | 939 |
| TGATGTGGCCAAGAACTAGG | 940 |
| TCTGATGATGTGGCCAAGAA | 941 |
| CTTTAAGGTGTCAACACCTG | 942 |
| GCTTTTTGTTGCAAAATCCT | 943 |
| TGATGATGTGGCCAAGAACT | 944 |
| CTGATGATGTGGCCAAGAAC | 945 |
| CAAGAACTAGGAGTCACCTG | 946 |
| GATGATGTGGCCAAGAACTA | 947 |
| ATGATGTGGCCAAGAACTAG | 948 |

-continued

| | |
|---|---|
| TTAATGTCCCTGAGCAGTTC | 949 |
| CCAGAAGGCCACACAGGGCA | 950 |
| TCCTTCCAGCCCAAACTGCA | 951 |
| TAATGTCCCTGAGCAGTTCT | 952 |
| TAGAGGAGGCTTGTGACTTC | 953 |
| TTTAATGTCCCTGAGCAGTT | 954 |
| TTAGAGGAGGCTTGTGACTT | 955 |
| GTCCCAGGTTGCCCCTCTCC | 956 |
| CCTCCTGGGAGCTGGCCTCC | 957 |
| CTGCTCCCAGTCTGCCTGCC | 958 |
| GTCTTGTCCCAGGTTGCCCC | 959 |
| TGTCCCAGGTTGCCCCTCTC | 960 |
| GCTCCCAGTCTGCCTGCCAT | 961 |
| TGCTCCCAGTCTGCCTGCCA | 962 |
| GGTTCCCCTTCCTCCTGGGA | 963 |
| CTCCTGGGAGCTGGCCTCCT | 964 |
| TCCTCCTGGGAGCTGGCCTC | 965 |
| CTGGGCTGGGCAGGAGCCCT | 966 |
| GGAGCCCTGAGCTGCCTGGT | 967 |
| CCCTCTGGGTGTCTTGTCCC | 968 |
| TTCCTGCTCCCAGTCTGCCT | 969 |
| TTGTCCCAGGTTGCCCCTCT | 970 |
| CTTGTCCCAGGTTGCCCCTC | 971 |
| TCTTGTCCCAGGTTGCCCCT | 972 |
| GCTGGGCAGGAGCCCTGAGC | 973 |
| AGCAGTTTCCCCAGAGCCCC | 974 |
| GCCCTCTGTTTTCCTGCTCC | 975 |
| GGGCCCTCTGTTTTCCTGCT | 976 |
| TTCCTCCTGGGAGCTGGCCT | 977 |
| GGTTGCCCCTCTCCTTGCAG | 978 |
| AGGTTGCCCCTCTCCTTGCA | 979 |
| CAGGTTGCCCCTCTCCTTGC | 980 |
| GGCTGGGCCACAGGCTAGCT | 981 |
| CTGTGGGTTCTGGTGTCCCC | 982 |
| GGCCCTCTGTTTTCCTGCTC | 983 |
| TGGGCTGGGCAGGAGCCCTG | 984 |
| TTTCCTGCTCCCAGTCTGCC | 985 |
| CTGGACCAGCCCACCCCAGT | 986 |
| CCCAGAGCCCCTGATCTGCC | 987 |
| CCCCAGAGCCCCTGATCTGC | 988 |

-continued

| | |
|---|---|
| CCTGGACCAGCCCACCCCAG | 989 |
| CCAGGTTGCCCCTCTCCTTG | 990 |
| GCCCCTGATCTGCCTGGACC | 991 |
| GTGTCTTGTCCCAGGTTGCC | 992 |
| GTTGCCCCTCTCCTTGCAGA | 993 |
| TGTCTTGTCCCAGGTTGCCC | 994 |
| GCAGCTGGAAGCCCAGCCCA | 995 |
| ATCCATGCCCTGGCTCTGGC | 996 |
| CCTCTGGGTGTCTTGTCCCA | 997 |
| GCCCAGCCCACAGCAGGACA | 998 |
| GGCCTTGAGGGTTCCCCACA | 999 |
| CCAGCAGTTTCCCCAGAGCC | 1000 |
| GAGCCCTGAGCTGCCTGGTG | 1001 |
| GTGTTCTCTCTCCCAGTTCC | 1002 |
| CCCTGAGCAGTTCTTGGCCC | 1003 |
| ACCCTCTGGGTGTCTTGTCC | 1004 |
| TACCTGGACCAGCCCACCCC | 1005 |
| GGTGTCTTGTCCCAGGTTGC | 1006 |
| AGTTTCCCCAGAGCCCCTGA | 1007 |
| GGCACCACCCCATCCACAGC | 1008 |
| AGCCCAGCCCACAGCAGGAC | 1009 |
| TCCTCCAGCTCTCAGCTTCT | 1010 |
| AGGAGCCCTGAGCTGCCTGG | 1011 |
| GCCTCTCTTCATGGGCCTGG | 1012 |
| TGGCTGGGCCACAGGCTAGC | 1013 |
| CTGGGTGTCTTGTCCCAGGT | 1014 |
| GTTTCCCCAGAGCCCCTGAT | 1015 |
| AGGCTGTGTTCTCTCTCCCA | 1016 |
| ACCTTCTGGTGCCTTGGGCT | 1017 |
| GCTACCTGGACCAGCCCACC | 1018 |
| TGCAGCTGGAAGCCCAGCCC | 1019 |
| TTCCCCAGAGCCCCTGATCT | 1020 |
| GCTATGGCCTACCCACTCCC | 1021 |
| AGCCCACTGTGGGTTCTGGT | 1022 |
| CCTTCTGGTGCCTTGGGCTT | 1023 |
| GCCTCTGGGTCTTTATGCCC | 1024 |
| CTCTCTCCCAGTTCCCCTAT | 1025 |
| CTCCCAGTCTGCCTGCCATA | 1026 |
| TGGACCAGCCCACCCCAGTA | 1027 |

-continued

| | |
|---|---|
| ATGGCCTACCCACTCCCCTG | 1028 |
| CCCTGGCCCTACAGACCTGT | 1029 |
| TCCCCAGAGCCCCTGATCTG | 1030 |
| GCCCACTGTGGGTTCTGGTG | 1031 |
| GAGCCCCTGATCTGCCTGGA | 1032 |
| CTACCTGGACCAGCCCACCC | 1033 |
| GCTAGTTGTGGCTGGGCCAC | 1034 |
| ACTGTGGGTTCTGGTGTCCC | 1035 |
| CAGCCCCAACCAGGTTCCCA | 1036 |
| TCCAGCAGTTTCCCCAGAGC | 1037 |
| CCTGAGCAGTTCTTGGCCCT | 1038 |
| GGCTATGGCCTACCCACTCC | 1039 |
| TATGGCCTACCCACTCCCCT | 1040 |
| CTATGGCCTACCCACTCCCC | 1041 |
| TCCACAGCTGACCCAGCCTC | 1042 |
| GTCCCTGAGCAGTTCTTGGC | 1043 |
| AGCTAGTTGTGGCTGGGCCA | 1044 |
| CAGCTAGTTGTGGCTGGGCC | 1045 |
| TCCCTGAGCAGTTCTTGGCC | 1046 |
| CCTCTGGGTCTTTATGCCCC | 1047 |
| CAGGAGCCCTGAGCTGCCTG | 1048 |
| TTTTCCTGCTCCCAGTCTGC | 1049 |
| ACAGCCCCAACCAGGTTCCC | 1050 |
| GAGGGCTGGCATCTCTCCTT | 1051 |
| CCCTGAGCTGCCTGGTGGAT | 1052 |
| CTGCAGCTGGAAGCCCAGCC | 1053 |
| GGGTGTCTTGTCCCAGGTTG | 1054 |
| TGGGTGTCTTGTCCCAGGTT | 1055 |
| AGCCCCTGATCTGCCTGGAC | 1056 |
| CCCCATCCACAGCTGACCCA | 1057 |
| GGGTCTTTATGCCCCAGTCT | 1058 |
| TTTCCCCAGAGCCCCTGATC | 1059 |
| GCCAGGCCTAGGTGCTTGAC | 1060 |
| CCCACTGTGGGTTCTGGTGT | 1061 |
| TCCCAGTCTGCCTGCCATAC | 1062 |
| CCCCTGATCTGCCTGGACCA | 1063 |
| TCTGGGTGTCTTGTCCCAGG | 1064 |
| TCCTGCTCTGTATGGCCTCT | 1065 |
| GCCTTGAGGGTTCCCCACAT | 1066 |
| GTCAGTTCTCCCTTTCTGCT | 1067 |

-continued

| | |
|---|---|
| GGGCTGGTTTGCCTCAACCC | 1068 |
| AGAGCCCCTGATCTGCCTGG | 1069 |
| GAGTTCCAGCAGTTTCCCCA | 1070 |
| GGTCTGCAGCTGGAAGCCCA | 1071 |
| TCTCTCCCAGTTCCCCTATT | 1072 |
| AGCCAGGCCTAGGTGCTTGA | 1073 |
| GTACCTGGTTAGTGCCAGCC | 1074 |
| AGGCCCACTGCAGGACAGGT | 1075 |
| GACAGGCCTTGAGGGTTCCC | 1076 |
| GATCTGGCTGACTCAGCCCC | 1077 |
| GGTTAGTGCCAGCCTTGGGA | 1078 |
| GCCTAGGTGCTTGACCTGGT | 1079 |
| GTTTTCCTGCTCCCAGTCTG | 1080 |
| TGTTTTCCTGCTCCCAGTCT | 1081 |
| CTGTTTTCCTGCTCCCAGTC | 1082 |
| TCTGTTTTCCTGCTCCCAGT | 1083 |
| AGCAGTTCTTGGCCCTTGGG | 1084 |
| CACCCTGGCCCTACAGACCT | 1085 |
| ACCCACACAGGCCCACTGCA | 1086 |
| GAGCTACCTGGACCAGCCCA | 1087 |
| ATTGTCCTCCAGCTCTCAGC | 1088 |
| GGCCCTACAGACCTGTGTCT | 1089 |
| GCCACAGGCTAGCTTGACCC | 1090 |
| GGCTGGTTTGCCTCAACCCT | 1091 |
| CTCTGGGTGTCTTGTCCCAG | 1092 |
| ACAGCTTCTCCAGCCTCTGG | 1093 |
| TCCAGAGCCATGTCCCTGGA | 1094 |
| ATGCCTCTCTTCATGGGCCT | 1095 |
| TCCTTGGCTATGGCCTACCC | 1096 |
| GGCCCACTGCAGGACAGGTG | 1097 |
| CCAGGCCTAGGTGCTTGACC | 1098 |
| CTGGTGCCTTGGGCTTTGGG | 1099 |
| ACCTGGTTAGTGCCAGCCTT | 1100 |
| TGCCTCTCTTCATGGGCCTG | 1101 |
| AAGCTGCTGGGCTGGGCAGG | 1102 |
| GCCACTTCTGAGTCCTCTGT | 1103 |
| GGACCAGCCCACCCCAGTAA | 1104 |
| GCTCTCTTTTCTGCTGTGGC | 1105 |
| TCCCCTGGCTGAAGAGTGCC | 1106 |

-continued

| | |
|---|---|
| AGTTGTGGCTGGGCCACAGG | 1107 |
| TCCTCTTCTCCTCCCAACCA | 1108 |
| AAGCCCAGCCCACAGCAGGA | 1109 |
| GAAGCCCAGCCCACAGCAGG | 1110 |
| TGCCCCTCTCCTTGCAGATG | 1111 |
| AGTTCCAGCAGTTTCCCCAG | 1112 |
| GCACAGCCCCAACCAGGTTC | 1113 |
| GACCCAGCCTCTGTCTAGGA | 1114 |
| GGTACCTGGTTAGTGCCAGC | 1115 |
| GGATCTGGCTGACTCAGCCC | 1116 |
| CTCCAGCCTCTGGGTCTTTA | 1117 |
| GGCCTTGGCTTAGAGGAGGC | 1118 |
| AGCTACCTGGACCAGCCCAC | 1119 |
| AGAGCTACCTGGACCAGCCC | 1120 |
| TCAGCTAGTTGTGGCTGGGC | 1121 |
| GGGTTCTGGTGTCCCCAGAA | 1122 |
| GGCCTAGGTGCTTGACCTGG | 1123 |
| CCCAGCCTCTGTCTAGGATC | 1124 |
| CCTTGGCTATGGCCTACCCA | 1125 |
| GCTGGTTTGCCTCAACCCTC | 1126 |
| CTGCACAGCCCCAACCAGGT | 1127 |
| GGCCACAGGCTAGCTTGACC | 1128 |
| CTGCAGCCCAGCCAAGCAGA | 1129 |
| CAGGCCAGAGGAGAGGTCCT | 1130 |
| TTCCTGCTCTGTATGGCCTC | 1131 |
| AGGCACCACCCCATCCACAG | 1132 |
| TCTGGTGCCTTGGGCTTTGG | 1133 |
| CCCCTGGCTGAAGAGTGCCA | 1134 |
| ACCCTGGCCCTACAGACCTG | 1135 |
| CCACACAGGCCCACTGCAGG | 1136 |
| CTTCTGGTGCCTTGGGCTTT | 1137 |
| TACCTGGTTAGTGCCAGCCT | 1138 |
| CAGAGCCCACTGTGGGTTCT | 1139 |
| GAGCAGTTCTTGGCCCTTGG | 1140 |
| AGTCAGTTCTCCCTTTCTGC | 1141 |
| CACTGTGGGTTCTGGTGTCC | 1142 |
| CTGGGTCTTTATGCCCCAGT | 1143 |
| GGCCAGAGGAGAGGTCCTGA | 1144 |
| TCTCTTTTCTGCTGTGGCCT | 1145 |
| CTCTCTTTTCTGCTGTGGCC | 1146 |

-continued

| | |
|---|---|
| AGCCTCTGGGTCTTTATGCC | 1147 |
| TGTGTTCTCTCTCCCAGTTC | 1148 |
| GGCCACTTCTGAGTCCTCTG | 1149 |
| GTCATATCCATGCCCTGGCT | 1150 |
| GTTTCCTCTTCTCCTCCCAA | 1151 |
| CACAGCCCCAACCAGGTTCC | 1152 |
| GGTGCTCTCTTTTCTGCTGT | 1153 |
| TGGTTAGTGCCAGCCTTGGG | 1154 |
| GCCTAATCCTCCAGGAGCCA | 1155 |
| TCCCAGCACTTTCTCTGTGC | 1156 |
| CTCTGGGTCTTTATGCCCCA | 1157 |
| ACCAAGGCACCACCCCATCC | 1158 |
| TGGGTCTTTATGCCCCAGTC | 1159 |
| CCTGCTCTGTATGGCCTCTG | 1160 |
| TATCCATGCCCTGGCTCTGG | 1161 |
| GGAGTCAGTTCTCCCTTTCT | 1162 |
| TACCCTCTGGGTGTCTTGTC | 1163 |
| GTATGGGTGGCAGTCACCTC | 1164 |
| GAAGCTGCTGGGCTGGGCAG | 1165 |
| AGAAGCTGCTGGGCTGGGCA | 1166 |
| GTTCTCCCTTTCTGCTATCC | 1167 |
| AAGGCTGTGTTCTCTCTCCC | 1168 |
| GTCCCTGGATATTGTCCTCC | 1169 |
| GCCCCAACCAGGTTCCCAAC | 1170 |
| GTCAGCTAGTTGTGGCTGGG | 1171 |
| TCTTTTCTGCTGTGGCCTGT | 1172 |
| GTCTCAGGAGAAGCCAGGCC | 1173 |
| GAGCTGCCTGGTGGATTGGT | 1174 |
| ACCCCACAGGCCAGAGGAGA | 1175 |
| TGCTCTGTATGGCCTCTGGG | 1176 |
| GTCACTTCTCCAGACAGGCC | 1177 |
| CCTCTTCTCCTCCCAACCAG | 1178 |
| GTCCTAGTATGGGTGGCAGT | 1179 |
| CAGGCCTAGGTGCTTGACCT | 1180 |
| CCAGAGCCATGTCCCTGGAT | 1181 |
| CTGAGCAGTTCTTGGCCCTT | 1182 |
| CCTGGCCCTACAGACCTGTG | 1183 |
| GGCTGCCTAATCCTCCAGGA | 1184 |
| AGCCCCAACCAGGTTCCCAA | 1185 |

-continued

| | |
|---|---|
| CTCCCCTGGCTGAAGAGTGC | 1186 |
| ACCCAGCCTCTGTCTAGGAT | 1187 |
| GGGCCACAGGCTAGCTTGAC | 1188 |
| GTGTTGCCTTTGCTGTGGTT | 1189 |
| GAAGCCAGGCCTAGGTGCTT | 1190 |
| CTGGCCCTACAGACCTGTGT | 1191 |
| CTAGTTGTGGCTGGGCCACA | 1192 |
| CCCCACAGGCCAGAGGAGAG | 1193 |
| CAGGCCCACTGCAGGACAGG | 1194 |
| GTGGTACCTGGTTAGTGCCA | 1195 |
| AGAAGCCAGGCCTAGGTGCT | 1196 |
| GCCAGCCTTGGGAAGGAGGG | 1197 |
| AAGTTTCCTCTTCTCCTCCC | 1198 |
| TGACCCAGCCTCTGTCTAGG | 1199 |
| GTCTTTATGCCCCAGTCTGG | 1200 |
| GGTCTTTATGCCCCAGTCTG | 1201 |
| TGGCCCTACAGACCTGTGTC | 1202 |
| GGGCAGTGCTCTCTTTGGAC | 1203 |
| GGTGCCATACAGAGCCCACT | 1204 |
| TCCAGACAGGCCTTGAGGGT | 1205 |
| AACCTTCTGGTGCCTTGGGC | 1206 |
| CCTGAGCTGCCTGGTGGATT | 1207 |
| AGGCCAGAGGAGAGGTCCTG | 1208 |
| TGGCTATGGCCTACCCACTC | 1209 |
| TCTGGTGCCATACAGAGCCC | 1210 |
| TGCACAGCCCCAACCAGGTT | 1211 |
| TCTGGCTGACTCAGCCCCAA | 1212 |
| TCACTCTACCCAGCCACTCT | 1213 |
| ACAGGCCAGAGGAGAGGTCC | 1214 |
| CTGCTCTGTATGGCCTCTGG | 1215 |
| CCAGCCTCTGTCTAGGATCT | 1216 |
| GGACCTCAGGAGGGAGTGGG | 1217 |
| AGAGCCCACTGTGGGTTCTG | 1218 |
| AGGGCAGTGCTCTCTTTGGA | 1219 |
| TGCCTAATCCTCCAGGAGCC | 1220 |
| ACAGAGCCCACTGTGGGTTC | 1221 |
| AGGGCTGGTTTGCCTCAACC | 1222 |
| CCACTGCAGGACAGGTGGCA | 1223 |
| GAGAAGCCAGGCCTAGGTGC | 1224 |
| TACCCACTCCCCTGGCTGAA | 1225 |

-continued

| | |
|---|---|
| TTTTCCAGAGCCATGTCCCT | 1226 |
| TTCCAGCAGTTTCCCCAGAG | 1227 |
| TCCAGCCTCTGGGTCTTTAT | 1228 |
| GACAGGAGTCAGTTCTCCCT | 1229 |
| TGGGCCACAGGCTAGCTTGA | 1230 |
| ATGGGTGGCAGTCACCTCTG | 1231 |
| CATATCCATGCCCTGGCTCT | 1232 |
| GGAGGGCTGGTTTGCCTCAA | 1233 |
| GCCCTACAGACCTGTGTCTG | 1234 |
| GTTGCCTTTGCTGTGGTTGG | 1235 |
| ATTCCTGCTCTGTATGGCCT | 1236 |
| CCCACAGGCCAGAGGAGAGG | 1237 |
| AGACAGGCCTTGAGGGTTCC | 1238 |
| CTGGTGCCATACAGAGCCCA | 1239 |
| GGGCAGAGGATCATGCCACC | 1240 |
| TCTGGGTCTTTATGCCCCAG | 1241 |
| TTACCCTCTGGGTGTCTTGT | 1242 |
| GTCTAAGGGCAGTGCTCTCT | 1243 |
| TCATATCCATGCCCTGGCTC | 1244 |
| AGGCCTAGGTGCTTGACCTG | 1245 |
| AGTATGGGTGGCAGTCACCT | 1246 |
| TCTGAGTCCTCTGTCTCAGG | 1247 |
| AGACCTGTGTCTGAGCAGGC | 1248 |
| CCTCAGGAGGGAGTGGGACT | 1249 |
| TATGGGTGGCAGTCACCTCT | 1250 |
| GCAGTCATCAGCCATTCCTT | 1251 |
| CACAGGCCCACTGCAGGACA | 1252 |
| AGCAGTCATCAGCCATTCCT | 1253 |
| AACCCACACAGGCCCACTGC | 1254 |
| CTCTTTTCTGCTGTGGCCTG | 1255 |
| GCAGAACACCCTGGCCCTAC | 1256 |
| AGGAGTCAGTTCTCCCTTTC | 1257 |
| TCACTTCTCCAGACAGGCCT | 1258 |
| CTTCAGGGACCAGAGGCAGC | 1259 |
| TTCTGGTGCCTTGGGCTTTG | 1260 |
| GGTTCTGGTGTCCCCAGAAT | 1261 |
| TGTGGTACCTGGTTAGTGCC | 1262 |
| GACCAAGGCACCACCCCATC | 1263 |
| TGGCTGCCTAATCCTCCAGG | 1264 |

-continued

| | |
|---|---|
| TCTGGTGTCCCCAGAATCCA | 1265 |
| TGTCAACACCTGGCCCTTGC | 1266 |
| GCTGCCTGGTGGATTGGTAC | 1267 |
| GAGACCAAGGCACCACCCCA | 1268 |
| CAGGTGCTCTCTTTTCTGCT | 1269 |
| CTGGCTGACTCAGCCCCAAC | 1270 |
| GCAAGGCTGTGTTCTCTCTC | 1271 |
| AAGCCAGGCCTAGGTGCTTG | 1272 |
| ACTGCACAGCCCCAACCAGG | 1273 |
| CCAGACAGGCCTTGAGGGTT | 1274 |
| AGCAGAACACCCTGGCCCTA | 1275 |
| TTGGCTATGGCCTACCCACT | 1276 |
| CTTGGCTATGGCCTACCCAC | 1277 |
| GGCAGAGGATCATGCCACCT | 1278 |
| ATCCTTGGCTATGGCCTACC | 1279 |
| GCCAGAGGAGAGGTCCTGAG | 1280 |
| TGTCCCTGAGCAGTTCTTGG | 1281 |
| TAGTTGTGGCTGGGCCACAG | 1282 |
| TCCTAGTATGGGTGGCAGTC | 1283 |
| ACACAGGCCCACTGCAGGAC | 1284 |
| AGCTGCCTGGTGGATTGGTA | 1285 |
| CTCCAGACAGGCCTTGAGGG | 1286 |
| CTTTTCTGCTGTGGCCTGTG | 1287 |
| GGGTGGCAGTCACCTCTGAA | 1288 |
| TTGCCTTTGCTGTGGTTGGG | 1289 |
| ACAGGAGTCAGTTCTCCCTT | 1290 |
| GACCTCAGGAGGGAGTGGGA | 1291 |
| CCTTGAGGGTTCCCCACATG | 1292 |
| GGCCAGGAAGCTTTGTCAGC | 1293 |
| GCCTGTGTGAATAGCCTGGC | 1294 |
| GCTGGACTCTGATTCCCTCA | 1295 |
| GTGCTGGGTTCTGTCAGATC | 1296 |
| TCAGTTCTCCCTTTCTGCTA | 1297 |
| CAGCCTCTGGGTCTTTATGC | 1298 |
| CTCTTCTCCTCCCAACCAGA | 1299 |
| AGGATCTGGCTGACTCAGCC | 1300 |
| AGGAGAAGCCAGGCCTAGGT | 1301 |
| GTGCCAGCCTTGGGAAGGAG | 1302 |
| AGTGCCAGCCTTGGGAAGGA | 1303 |
| ACAGGCCCACTGCAGGACAG | 1304 |

-continued

| | |
|---|---|
| CTCTGGTGCCATACAGAGCC | 1305 |
| TCAGGGACCAGAGGCAGCAC | 1306 |
| CAGGAGTCAGTTCTCCCTTT | 1307 |
| TCCCTGGATATTGTCCTCCA | 1308 |
| ACTCTACCCAGCCACTCTGA | 1309 |
| TGAGCAGTTCTTGGCCCTTG | 1310 |
| TTCTGGTGTCCCCAGAATCC | 1311 |
| GGGCTGGATGCTGGACTCTG | 1312 |
| GCAACTGGAGGTCTGCAGCT | 1313 |
| CTGCCTAATCCTCCAGGAGC | 1314 |
| GCTGCCTAATCCTCCAGGAG | 1315 |
| CTGCCTGGTGGATTGGTACC | 1316 |
| TTTCCTCTTCTCCTCCCAAC | 1317 |
| TTCAGGGACCAGAGGCAGCA | 1318 |
| TCTTTATGCCCCAGTCTGGA | 1319 |
| CACTCTACCCAGCCACTCTG | 1320 |
| GTTCTGGTGTCCCCAGAATC | 1321 |
| GTGTCAACACCTGGCCCTTG | 1322 |
| TGGTGCCATACAGAGCCCAC | 1323 |
| CAAGGCTGTGTTCTCTCTCC | 1324 |
| GTGTCTGAGCAGGCTTTGGA | 1325 |
| CCTAGTATGGGTGGCAGTCA | 1326 |
| GGCTAGATCAGCAATGCCCC | 1327 |
| CACTCCCCTGGCTGAAGAGT | 1328 |
| GGAGAAGCCAGGCCTAGGTG | 1329 |
| CCTAGGTGCTTGACCTGGTG | 1330 |
| GCCAGGAAGCTTTGTCAGCT | 1331 |
| GTGCTCTCTTTTCTGCTGTG | 1332 |
| CCTGATCTGCCTGGACCAGA | 1333 |
| ACTGTGGGTTCTCCTGGTAT | 1334 |
| CTCCTTCCAGCCCAAACTGC | 1335 |
| CCCCAACCAGGTTCCCAACA | 1336 |
| CCTGTGTGAATAGCCTGGCC | 1337 |
| ACCTCAGGAGGGAGTGGGAC | 1338 |
| GAGTCAGTTCTCCCTTTCTG | 1339 |
| AGACCAAGGCACCACCCCAT | 1340 |
| TCTCCAGACAGGCCTTGAGG | 1341 |
| ATTTTCCAGAGCCATGTCCC | 1342 |
| CCAGCCTCTGGGTCTTTATG | 1343 |

-continued

| | |
|---|---|
| CACTTCTCCAGACAGGCCTT | 1344 |
| GTCTGAGCAGGCTTTGGAGG | 1345 |
| CCAGCCCAAACTGCACAGCC | 1346 |
| GTGGCCTGTGTGAATAGCCT | 1347 |
| GGTCTCTCACAGGATGCTGG | 1348 |
| TGTCAGCTAGTTGTGGCTGG | 1349 |
| TGCCAGCCTTGGGAAGGAGG | 1350 |
| GGTGCTTGACCTGGTGATCT | 1351 |
| CCTGGTGATCTGAGCTGTGT | 1352 |
| TGGCAAGGCTGTGTTCTCTC | 1353 |
| AGGTGCTCTCTTTTCTGCTG | 1354 |
| GACCAGCCCACCCCAGTAAA | 1355 |
| GAGGGCTGGTTTGCCTCAAC | 1356 |
| GTGTAGCAGTCATCAGCCAT | 1357 |
| GCCATACAGAGCCCACTGTG | 1358 |
| TGCCATACAGAGCCCACTGT | 1359 |
| GTGCCATACAGAGCCCACTG | 1360 |
| GGAATCCTTACCCTCTGGGT | 1361 |
| GATGGCTGCCTAATCCTCCA | 1362 |
| TACAGAGCCCACTGTGGGTT | 1363 |
| ACAGGTGCTCTCTTTTCTGC | 1364 |
| TTTCCCAGCACTTTCTCTGT | 1365 |
| CCAGCCTTGGGAAGGAGGGA | 1366 |
| GTTAGTGCCAGCCTTGGGAA | 1367 |
| CACAGGCCAGAGGAGAGGTC | 1368 |
| CTGGTGTCCCCAGAATCCAT | 1369 |
| GGAGGCTTGTGACTTCAGCT | 1370 |
| GGCTTGGTGATCTCTGGAGG | 1371 |
| GGGCTTGGTGATCTCTGGAG | 1372 |
| CAGCCCACCCCAGTAAATCC | 1373 |
| CCAGCCCACCCCAGTAAATC | 1374 |
| TGCTGGACTCTGATTCCCTC | 1375 |
| CCTGTGTCACTTCTCCAGAC | 1376 |
| ATCCTCCAGGAGCCATTTTC | 1377 |
| AAGCAGAACACCCTGGCCCT | 1378 |
| AACCCCACAGGCCAGAGGAG | 1379 |
| TGGTACCTGGTTAGTGCCAG | 1380 |
| TATTGTCCTCCAGCTCTCAG | 1381 |
| ATACAGAGCCCACTGTGGGT | 1382 |
| AACAGCTTCTCCAGCCTCTG | 1383 |

-continued

| | |
|---|---|
| TGCAGGACAGGTGGCAGAGG | 1384 |
| TGCTCTCTTTTCTGCTGTGG | 1385 |
| TGTCTAAGGGCAGTGCTCTC | 1386 |
| AAGGCCACTTCTGAGTCCTC | 1387 |
| TGAGCTGCCTGGTGGATTGG | 1388 |
| GGCTGGATGCTGGACTCTGA | 1389 |
| GGAGAGGTCCTGAGAGAGGT | 1390 |
| CTGGTCTCTCACAGGATGCT | 1391 |
| GCCAAGCAGAACACCCTGGC | 1392 |
| GATATTGTCCTCCAGCTCTC | 1393 |
| TATTCCTGCTCTGTATGGCC | 1394 |
| TGTCCCTGGATATTGTCCTC | 1395 |
| CTCAGGAGAAGCCAGGCCTA | 1396 |
| CCTAATCCTCCAGGAGCCAT | 1397 |
| ACCAGAAGGCCACACAGGGC | 1398 |
| CAGACAGGCCTTGAGGGTTC | 1399 |
| GGCCTGTGTGAATAGCCTGG | 1400 |
| GCAGATGGCTGCCTAATCCT | 1401 |
| AATCCTTACCCTCTGGGTGT | 1402 |
| ACTCCCCTGGCTGAAGAGTG | 1403 |
| TTGTCCTAGTATGGGTGGCA | 1404 |
| ACTGGCCTTGGCTTAGAGGA | 1405 |
| TGTCTCAGGAGAAGCCAGGC | 1406 |
| GGTTCAGGAGAGCTACCTGG | 1407 |
| TGCTTGGCAAGGCTGTGTTC | 1408 |
| ATATTGTCCTCCAGCTCTCA | 1409 |
| TGTCCTAGTATGGGTGGCAG | 1410 |
| GGGAGGATCTGGCTGACTCA | 1411 |
| AGATGGCTGCCTAATCCTCC | 1412 |
| CAGTTCTCCCTTTCTGCTAT | 1413 |
| GGCTTGTGACTTCAGCTGTT | 1414 |
| TCTGGTCTCTCACAGGATGC | 1415 |
| TGTCACTTCTCCAGACAGGC | 1416 |
| GCTAGATCAGCAATGCCCCA | 1417 |
| CTGTGGGTTCTCCTGGTATA | 1418 |
| TAGTATGGGTGGCAGTCACC | 1419 |
| GGTGGCAGTCACCTCTGAAC | 1420 |
| TGTTGCCTTTGCTGTGGTTG | 1421 |
| GCAGAGGATCATGCCACCTT | 1422 |

-continued

| | |
|---|---|
| GGAGGTTCAGGAGAGCTACC | 1423 |
| AGGCTTGTGACTTCAGCTGT | 1424 |
| TAGTGCCAGCCTTGGGAAGG | 1425 |
| GATTGGGTAATGCAGGGCCC | 1426 |
| CACTGGCCTTGGCTTAGAGG | 1427 |
| CCCTACAGACCTGTGTCTGA | 1428 |
| AGCAACTGGAGGTCTGCAGC | 1429 |
| GATCCTTGGCTATGGCCTAC | 1430 |
| TAGCAGTCATCAGCCATTCC | 1431 |
| CAGAGCCATGTCCCTGGATA | 1432 |
| ATGGCTGCCTAATCCTCCAG | 1433 |
| TGTGCTGGGTTCTGTCAGAT | 1434 |
| ATGTGCTGGGTTCTGTCAGA | 1435 |
| CTGGCCTTGGCTTAGAGGAG | 1436 |
| TGTGTCTGAGCAGGCTTTGG | 1437 |
| GTGAATAGCCTGGCCATGCT | 1438 |
| ACTTCTCCAGACAGGCCTTG | 1439 |
| CTTGAGGGTTCCCCACATGA | 1440 |
| ATCCTCCTCAAGCTGACTGC | 1441 |
| CAAGCAGAACACCCTGGCCC | 1442 |
| CCAAGCAGAACACCCTGGCC | 1443 |
| ACCAGCCCACCCCAGTAAAT | 1444 |
| AGAAGGCCACACAGGGCAGT | 1445 |
| GTCTCTCACAGGATGCTGGA | 1446 |
| TAACCCCACAGGCCAGAGGA | 1447 |
| GTAGCAGTCATCAGCCATTC | 1448 |
| GAGAGACCAAGGCACCACCC | 1449 |
| GACCTGGTGATCTGAGCTGT | 1450 |
| CAGGAGAAGCCAGGCCTAGG | 1451 |
| TTGGCAAGGCTGTGTTCTCT | 1452 |
| ATCTGAGCTGTGTTTGTCCT | 1453 |
| GAGGATCTGGCTGACTCAGC | 1454 |
| CACTTCAGGGACCAGAGGCA | 1455 |
| GTGTCCCCAGAATCCATGTG | 1456 |
| TCTAAGGGCAGTGCTCTCTT | 1457 |
| ATGGCAGCTTCATTCCTGGA | 1458 |
| CTTTCTCTGTGCCCAGAGAT | 1459 |
| GGGAGACTGGTTTCAGGAGC | 1460 |
| TTTGTCCTAGTATGGGTGGC | 1461 |
| TGCTGGGTTCTGTCAGATCA | 1462 |

-continued

CCCTTTCTGCTATCCATCAC                              1463

GCTTGGTGATCTCTGGAGGA                              1464

TCAGGAGAGCTACCTGGACC                              1465

CTGCTGTGGCCTGTGTGAAT                              1466

TCACAGGTGCTCTCTTTTCT                              1467

CAGACCTGTGTCTGAGCAGG                              1468

TCCAGCCCAAACTGCACAGC                              1469

GAGGTTCAGGAGAGCTACCT                              1470

AGGTGCTTGACCTGGTGATC                              1471

CCATACAGAGCCCACTGTGG                              1472

GTGTTTGTCCTAGTATGGGT                              1473

AAGGGCAGTGCTCTCTTTGG                              1474

CATTGCTGCTTGGCAAGGCT                              1475

TTTGTCAGCTAGTTGTGGCT                              1476

CTTTGTCAGCTAGTTGTGGC                              1477

GCTTTGTCAGCTAGTTGTGG                              1478

GCCTCTGTCTAGGATCTAGA                              1479

TGGATATTGTCCTCCAGCTC                              1480

CCCTGGCTGAAGAGTGCCAA                              1481

TGGGCAGAGGATCATGCCAC                              1482

GTGTCACTTCTCCAGACAGG                              1483

TCAACTCACTCTACCCAGCC                              1484

AGGAGCCATTTTCCAAGGGC                              1485

GCTTGTGACTTCAGCTGTTC                              1486

TTGTCTAAGGGCAGTGCTCT                              1487

CTTGTCTAAGGGCAGTGCTC                              1488

TCTTGTCTAAGGGCAGTGCT                              1489

CTCTTGTCTAAGGGCAGTGC                              1490

CTAGGTGCTTGACCTGGTGA                              1491

TGAGCTGTGTTTGTCCTAGT                              1492

ATGCTGGACTCTGATTCCCT                              1493

AGGAGGCTTGTGACTTCAGC                              1494

GGCTTAGAGGAGGCTTGTGA                              1495

ACACTTCAGGGACCAGAGGC                              1496

TGTGGCCTGTGTGAATAGCC                              1497

TCTGAGCAGGCTTTGGAGGA                              1498

TTCTCCAGACAGGCCTTGAG                              1499

CAGCCTCTGTCTAGGATCTA                              1500

GCCCACAATGGGCAGAGGAT                              1501

-continued

| | |
|---|---|
| GTTCAGGAGAGCTACCTGGA | 1502 |
| GAGCCATGTCCCTGGATATT | 1503 |
| GATCTGAGCTGTGTTTGTCC | 1504 |
| CCAGCCAAGCAGAACACCCT | 1505 |
| CAGGAGAGCTACCTGGACCA | 1506 |
| CTGTGTGAATAGCCTGGCCA | 1507 |
| GGATTTGCAGTCAGCAGAGC | 1508 |
| CACACTGGCCTTGGCTTAGA | 1509 |
| GTTGGGATTTGCAGTCAGCA | 1510 |
| AGAGCCATGTCCCTGGATAT | 1511 |
| AACTGTGGGTTCTCCTGGTA | 1512 |
| TGCCCACAATGGGCAGAGGA | 1513 |
| ACTCTGGTGCCATACAGAGC | 1514 |
| GCTGACTGCTATCAGCAGGA | 1515 |
| CTCAGGAGGGAGTGGGACTG | 1516 |
| GTGTGGCTGGACTTTTGACC | 1517 |
| TCAGGAGAAGCCAGGCCTAG | 1518 |
| ACTTCAGGGACCAGAGGCAG | 1519 |
| TTGTCAGCTAGTTGTGGCTG | 1520 |
| CCCCAGAATCCATGTGTCTT | 1521 |
| CCCAACCAGGTTCCCAACAC | 1522 |
| TGGGTCAGCTTTTTGTTGCA | 1523 |
| ATGTCCCTGGATATTGTCCT | 1524 |
| ATGTGGTACCTGGTTAGTGC | 1525 |
| GTGGCAGTCACCTCTGAACA | 1526 |
| GAGCTGTGTTTGTCCTAGTA | 1527 |
| TCTTTTTCCATCTGTCCTGG | 1528 |
| TCATCCTCCTCAAGCTGACT | 1529 |
| GTTTGTCCTAGTATGGGTGG | 1530 |
| ACTGGTTTCAGGAGCTGTTC | 1531 |
| GATGCTGGACTCTGATTCCC | 1532 |
| CTTGTGACTTCAGCTGTTCC | 1533 |
| CATACAGAGCCCACTGTGGG | 1534 |
| GAATCCTTACCCTCTGGGTG | 1535 |
| CTTCTGTTGGGTTGTTGCAC | 1536 |
| ACTTCTGTTGGGTTGTTGCA | 1537 |
| CTAGTATGGGTGGCAGTCAC | 1538 |
| GGTGGAGGAAGGATCAGGCT | 1539 |
| TGCAGATGGCTGCCTAATCC | 1540 |
| CCCAAACTGCACAGCCCCAA | 1541 |

-continued

```
TGTCTGAGCAGGCTTTGGAG                                1542

GTGCTTGACCTGGTGATCTG                                1543

TGGTCTCTCACAGGATGCTG                                1544

GAGGATCATGCCACCTTGGA                                1545

CTAAGGGCAGTGCTCTCTTT                                1546

TCAGGAGGGAGTGGGACTGA                                1547

ACACACTGGCCTTGGCTTAG                                1548

ACCTGGTGATCTGAGCTGTG                                1549

AGGAGAGCTACCTGGACCAG                                1550

AGCCTCTGTCTAGGATCTAG                                1551

TCATCCCCTGGAGATACTCA                                1552

ACACTGGCCTTGGCTTAGAG                                1553

TTGGCTTAGAGGAGGCTTGT                                1554

CTGTGTCACTTCTCCAGACA                                1555

GAATAGCCTGGCCATGCTGA                                1556

CTGGACTCTGATTCCCTCAG                                1557

ACATTGCTGCTTGGCAAGGC                                1558

GGGTTCTCCTGGTATATCTA                                1559

TTGCCCACAATGGGCAGAGG                                1560

GGCTAACATTGCTGCTTGGC                                1561

TGTGAATAGCCTGGCCATGC                                1562

GAGGCTTGTGACTTCAGCTG                                1563

GTGGCTGGACTTTTGACCTT                                1564

TTAGTGCCAGCCTTGGGAAG                                1565

AACTGCACAGCCCCAACCAG                                1566

GAGGTCCTGAGAGAGGTGAC                                1567

AGGTTCAGGAGAGCTACCTG                                1568

TCTTCTCCTCCCAACCAGAA                                1569

GCTGGATGCTGGACTCTGAT                                1570

GGAGGATCTGGCTGACTCAG                                1571

GGACTCTGATTCCCTCAGAG                                1572

TGTAGCAGTCATCAGCCATT                                1573

GCCCACAGCAGGACAAGCAA                                1574

TTTGCAGTCAGCAGAGCACA                                1575

GAGATACTTCCCACTTCCTC                                1576

GACAGAGACTCTGGTGCCAT                                1577

CAGATGGCTGCCTAATCCTC                                1578

AGCTGACTGCTATCAGCAGG                                1579

ACTTCCCACTTCCTCATACA                                1580
```

-continued

| | |
|---|---|
| TGGCCTGTGTGAATAGCCTG | 1581 |
| CTTTATGCCCCAGTCTGGAA | 1582 |
| CAGTCATCAGCCATTCCTTA | 1583 |
| AGGTCCTGAGAGAGGTGACA | 1584 |
| TGACAGAGACTCTGGTGCCA | 1585 |
| CATAACCCACACAGGCCCAC | 1586 |
| TGGAATCCTTACCCTCTGGG | 1587 |
| AGATACTTCCCACTTCCTCA | 1588 |
| AAAGTTTCCTCTTCTCCTCC | 1589 |
| TTGTGACTTCAGCTGTTCCA | 1590 |
| CTGGTGATCTGAGCTGTGTT | 1591 |
| TCCCCTGGAGATACTCAGAC | 1592 |
| GGCAGAGGAGCTATTTGGGA | 1593 |
| AGAGGTCCTGAGAGAGGTGA | 1594 |
| GAGAGGTCCTGAGAGAGGTG | 1595 |
| CCCCAGTAAATCCTGTGTCA | 1596 |
| CACAGGTGCTCTCTTTTCTG | 1597 |
| TGGCTTAGAGGAGGCTTGTG | 1598 |
| GAACACACTGGCCTTGGCTT | 1599 |
| TTCTGTTGGGTTGTTGCACA | 1600 |
| TGGACTCTGATTCCCTCAGA | 1601 |
| GGATGCTGGACTCTGATTCC | 1602 |
| GATTTGCAGTCAGCAGAGCA | 1603 |
| CTGTGGCCTGTGTGAATAGC | 1604 |
| ACAGACCTGTGTCTGAGCAG | 1605 |
| AATAGCCTGGCCATGCTGAC | 1606 |
| GATACTTCCCACTTCCTCAT | 1607 |
| CTAATCCTCCAGGAGCCATT | 1608 |
| CTACAGACCTGTGTCTGAGC | 1609 |
| GAGGAGGTTCAGGAGAGCTA | 1610 |
| TTGGGACAGGAGTCAGTTCT | 1611 |
| CATCTTTTTCCATCTGTCCT | 1612 |
| GGGCAGTGGACAACAGTGGA | 1613 |
| AGGAGAGGTCCTGAGAGAGG | 1614 |
| AGAGGATCATGCCACCTTGG | 1615 |
| TTTATGTGCTGGGTTCTGTC | 1616 |
| GGCAGTCACCTCTGAACACA | 1617 |
| CCAGGAGCCATTTTCCAAGG | 1618 |
| CCCACTTCCTCATACATTCT | 1619 |
| CTTCCCACTTCCTCATACAT | 1620 |

-continued

| | |
|---|---|
| AAACCTTCTGGTGCCTTGGG | 1621 |
| CCCCTGGAGATACTCAGACA | 1622 |
| TAGGTGCTTGACCTGGTGAT | 1623 |
| GCCCCAGTCTGGAAACATTC | 1624 |
| AGCTGTGTTTGTCCTAGTAT | 1625 |
| CCATGCTCATAATGGAGCCC | 1626 |
| CCCATGCTCATAATGGAGCC | 1627 |
| TCTGTTGGGTTGTTGCACAT | 1628 |
| TATTTTCCAGAGCCATGTCC | 1629 |
| AAACTGTGGGTTCTCCTGGT | 1630 |
| GTGTGAATAGCCTGGCCATG | 1631 |
| TGTGTGAATAGCCTGGCCAT | 1632 |
| GGATCATGCCACCTTGGATT | 1633 |
| ACCCCAGTAAATCCTGTGTC | 1634 |
| TGAACACACTGGCCTTGGCT | 1635 |
| ATCCCCTGGAGATACTCAGA | 1636 |
| ATCATCCCCTGGAGATACTC | 1637 |
| GCTTAGAGGAGGCTTGTGAC | 1638 |
| TGCTGTGGCCTGTGTGAATA | 1639 |
| CACCTCTGAACACACTGGCC | 1640 |
| CTGGGTTCTGTCAGATCACA | 1641 |
| AGGATCATGCCACCTTGGAT | 1642 |
| GGGTTCCCCACATGAAATCC | 1643 |
| AAGAGTGTTGCCTTTGCTGT | 1644 |
| TCTGTCTCAGGAGAAGCCAG | 1645 |
| AGCCAAGCAGAACACCCTGG | 1646 |
| CATCCTCCTCAAGCTGACTG | 1647 |
| CATCCCCTGGAGATACTCAG | 1648 |
| TCCCACTTCCTCATACATTC | 1649 |
| GTGGCAGAGGAGCTATTTGG | 1650 |
| CCAAGCAACTGGAGGTCTGC | 1651 |
| CCCAGAATCCATGTGTCTTC | 1652 |
| AGCTTTGTCAGCTAGTTGTG | 1653 |
| GCTCATAATGGAGCCCTTTC | 1654 |
| CCACACAGGGCAGTGGACAA | 1655 |
| CCTACAGACCTGTGTCTGAG | 1656 |
| AATCCTCCAGGAGCCATTTT | 1657 |
| ATTCCTGGAATCCTTACCCT | 1658 |
| GCTGTGTTTGTCCTAGTATG | 1659 |

-continued

| | |
|---|---|
| TTGACCTGGTGATCTGAGCT | 1660 |
| CTTGACCTGGTGATCTGAGC | 1661 |
| GCTTGACCTGGTGATCTGAG | 1662 |
| GTGATCTGAGCTGTGTTTGT | 1663 |
| TGAATAGCCTGGCCATGCTG | 1664 |
| ACTTATAACCCCACAGGCCA | 1665 |
| CACTTATAACCCCACAGGCC | 1666 |
| CTTGGCTTAGAGGAGGCTTG | 1667 |
| AGAGAGACCAAGGCACCACC | 1668 |
| ATATTCCTGCTCTGTATGGC | 1669 |
| CACCCCAGTAAATCCTGTGT | 1670 |
| ATTTGCAGTCAGCAGAGCAC | 1671 |
| GGAAGGCCAGGAAGCTTTGT | 1672 |
| AGCTTCATTCCTGGAATCCT | 1673 |
| GCTAACATTGCTGCTTGGCA | 1674 |
| CAGGAGGGAGTGGGACTGAT | 1675 |
| AAAGGCCACTTCTGAGTCCT | 1676 |
| CCCACAATGGGCAGAGGATC | 1677 |
| AGGAGGTTCAGGAGAGCTAC | 1678 |
| ATGACAGAGACTCTGGTGCC | 1679 |
| TACAGACCTGTGTCTGAGCA | 1680 |
| GCAGGCTTTGGAGGAAAGGC | 1681 |
| GTGACACTTCAGGGACCAGA | 1682 |
| GGGATATTCCTGCTCTGTAT | 1683 |
| GGGTCAGCTTTTTGTTGCAA | 1684 |
| TGATTGGGTAATGCAGGGCC | 1685 |
| CTTATAACCCCACAGGCCAG | 1686 |
| AGGGAAGGCCAGGAAGCTTT | 1687 |
| TGTGTCACTTCTCCAGACAG | 1688 |
| TGCTTGACCTGGTGATCTGA | 1689 |
| TCTTTTATGTGCTGGGTTCT | 1690 |
| GTGTCTTCATTCATTCACCT | 1691 |
| TCCAGGAGCCATTTTCCAAG | 1692 |
| GGCTTTGGAGGAAAGGCCAC | 1693 |
| GCAGAGGTCAACCAGAAGGC | 1694 |
| TGACCTGGTGATCTGAGCTG | 1695 |
| AGGGCAGTGGACAACAGTGG | 1696 |
| TTCAGGAGAGCTACCTGGAC | 1697 |
| CAGGAGCCATTTTCCAAGGG | 1698 |
| TGAGATACTTCCCACTTCCT | 1699 |

-continued

```
CTGAGATACTTCCCACTTCC                                1700

GGTCAACCAGAAGGCCACAC                                1701

GAGTGTGGCTGGACTTTTGA                                1702

TGGCAGAGGAGCTATTTGGG                                1703

TACTTCCCACTTCCTCATAC                                1704

AGAGCCAGAAATCATCCCCT                                1705

TAAGGGCAGTGCTCTCTTTG                                1706

TTCAACTCACTCTACCCAGC                                1707

GAGGTCAACCAGAAGGCCAC                                1708

GAGGAGGCTTGTGACTTCAG                                1709

AGAGGAGGCTTGTGACTTCA                                1710

GACCTTTAATGTCCCTGAGC                                1711

TCTGCCTGGACCAGAAGACA                                1712

GAAAGGCCACTTCTGAGTCC                                1713

AGGCTTTGGAGGAAAGGCCA                                1714

CAGGCTTTGGAGGAAAGGCC                                1715

GGGAAGGCCAGGAAGCTTTG                                1716

AATGGCAGCTTCATTCCTGG                                1717

TGGCAGTCACCTCTGAACAC                                1718

GGTGATCTGAGCTGTGTTTG                                1719

TGGTGATCTGAGCTGTGTTT                                1720

GAGGAGAGGTCCTGAGAGAG                                1721

TTGAGGGTTCCCCACATGAA                                1722

GACTCTGGTGCCATACAGAG                                1723

AGACTCTGGTGCCATACAGA                                1724

GAGACTCTGGTGCCATACAG                                1725

AGAGACTCTGGTGCCATACA                                1726

CAGAGACTCTGGTGCCATAC                                1727

ACAGAGACTCTGGTGCCATA                                1728

TTCCAGCCCAAACTGCACAG                                1729

CAGAGGATCATGCCACCTTG                                1730

TTATAACCCCACAGGCCAGA                                1731

TAATCCTCCAGGAGCCATTT                                1732

AGGTCAACCAGAAGGCCACA                                1733

CCTGGCTGAAGAGTGCCAAT                                1734

CTGTTGGGTTGTTGCACATT                                1735

ACCTTTAATGTCCCTGAGCA                                1736

GGAGGAAGAGTGTTGCCTTT                                1737

AGGAGGGAGTGGGACTGATT                                1738
```

-continued

| | |
|---|---|
| CTGATCTGCCTGGACCAGAA | 1739 |
| TTGGGATTTGCAGTCAGCAG | 1740 |
| AAACTGCACAGCCCCAACCA | 1741 |
| CAAACTGCACAGCCCCAACC | 1742 |
| GAGCCAGAAATCATCCCCTG | 1743 |
| AACACACTGGCCTTGGCTTA | 1744 |
| GCTATTTGGGACAGGAGTCA | 1745 |
| AGAGGTCAACCAGAAGGCCA | 1746 |
| CAGAGGTCAACCAGAAGGCC | 1747 |
| TTCCCACTTCCTCATACATT | 1748 |
| GGTTCCCCACATGAAATCCA | 1749 |
| AAACTCTCTCTCTGGTCTCT | 1750 |
| GAAGGCCAGGAAGCTTTGTC | 1751 |
| TGTTTGTCCTAGTATGGGTG | 1752 |
| TGTGTTTGTCCTAGTATGGG | 1753 |
| TCTCTGAGATACTTCCCACT | 1754 |
| CAGCCAAGCAGAACACCCTG | 1755 |
| GGTTCTGTCAGATCACATGT | 1756 |
| ATTGCCCACAATGGGCAGAG | 1757 |
| TTTGGGACAGGAGTCAGTTC | 1758 |
| TGCCCCAGTCTGGAAACATT | 1759 |
| GCAGAGGAGCTATTTGGGAC | 1760 |
| GATCTGCCTGGACCAGAAGA | 1761 |
| CCTTTAATGTCCCTGAGCAG | 1762 |
| ATACTTCCCACTTCCTCATA | 1763 |
| CATGCTCATAATGGAGCCCT | 1764 |
| ACAGGGCAGTGGACAACAGT | 1765 |
| AAGGCCAGGAAGCTTTGTCA | 1766 |
| AGTGGACAACAGTGGAGGGT | 1767 |
| GTGCCCAGAGATGTCAAGAG | 1768 |
| GGGAGTGGGACTGATTGGAG | 1769 |
| AGGGAGTGGGACTGATTGGA | 1770 |
| GAGGGAGTGGGACTGATTGG | 1771 |
| GGAGGGAGTGGGACTGATTG | 1772 |
| AGGGAGACTGGTTTCAGGAG | 1773 |
| AGTGTGGCTGGACTTTTGAC | 1774 |
| TGGAGGAAGAGTGTTGCCTT | 1775 |
| ACTCTTGTCTAAGGGCAGTG | 1776 |
| AATGGGCAGAGGATCATGCC | 1777 |
| GCAGTCACCTCTGAACACAC | 1778 |

-continued

| | |
|---|---|
| GGTTCTCCTGGTATATCTAT | 1779 |
| GCAGTCAGCAGAGCACAATT | 1780 |
| GAGAGGTGACACTTCAGGGA | 1781 |
| CATGCCACCTTGGATTTTCA | 1782 |
| GTGGAGGAAGGATCAGGCTA | 1783 |
| GCTAGGTGGAGGAAGGATCA | 1784 |
| ACAACAGAAGCTGCTGGGCT | 1785 |
| CTGAGCAGGCTTTGGAGGAA | 1786 |
| TCCTCCCAACCAGAAATGGC | 1787 |
| TGCTCATAATGGAGCCCTTT | 1788 |
| CCATCTGTCCTGGAATGAGG | 1789 |
| CTTTAATGTCCCTGAGCAGT | 1790 |
| GCTATCAGCAGGAGAAGGGA | 1791 |
| TGGCTGGACTTTTGACCTTT | 1792 |
| TCTTCAACTCACTCTACCCA | 1793 |
| TCTCTGAATACTGCCCTTGG | 1794 |
| GCAACTCTTGTCTAAGGGCA | 1795 |
| ATCCAAACTCTCTCTCTGGT | 1796 |
| TGTGCCCAGAGATGTCAAGA | 1797 |
| TCACCTCTGAACACACTGGC | 1798 |
| AGCCATTTCCATCAAGCTTT | 1799 |
| GCAGTGGACAACAGTGGAGG | 1800 |
| GGCAGTGGACAACAGTGGAG | 1801 |
| CTCAACTTCTGTTGGGTTGT | 1802 |
| GATCATGCCACCTTGGATTT | 1803 |
| CTGTGTTTGTCCTAGTATGG | 1804 |
| GAGTTGGGATTTGCAGTCAG | 1805 |
| AGAGTTGGGATTTGCAGTCA | 1806 |
| TCTGATTCCCTCAGAGAGAC | 1807 |
| GGGTTCTGTCAGATCACATG | 1808 |
| TGGGTTCTGTCAGATCACAT | 1809 |
| GGAAAGGCCACTTCTGAGTC | 1810 |
| ATCTGCCTGGACCAGAAGAC | 1811 |
| TGATCTGAGCTGTGTTTGTC | 1812 |
| CTGACTGCTATCAGCAGGAG | 1813 |
| CAAACTCTCTCTCTGGTCTC | 1814 |
| CCTCCCAACCAGAAATGGCA | 1815 |
| CAGGGCAGTGGACAACAGTG | 1816 |
| AGCTATTTGGGACAGGAGTC | 1817 |

-continued

| | |
|---|---|
| TCACTTATAACCCCACAGGC | 1818 |
| ATGCTCATAATGGAGCCCTT | 1819 |
| CTGATTGGGTAATGCAGGGC | 1820 |
| TATGCCCCAGTCTGGAAACA | 1821 |
| AACTTCTGTTGGGTTGTTGC | 1822 |
| TGCAGTCAGCAGAGCACAAT | 1823 |
| GTTGGGTTGTTGCACATTTT | 1824 |
| GGCAGAGGTCAACCAGAAGG | 1825 |
| GGGCAGAGGTCAACCAGAAG | 1826 |
| GGCTGGACTTTTGACCTTTA | 1827 |
| CCCAGTAAATCCTGTGTCAC | 1828 |
| TGAGTGTGGCTGGACTTTTG | 1829 |
| AGACAGAGGGCAAGAGGAGC | 1830 |
| CTTAGAGGAGGCTTGTGACT | 1831 |
| TTCTTTTATGTGCTGGGTTC | 1832 |
| GTCATCAGCCATTCCTTAAC | 1833 |
| CACCAAGCAACTGGAGGTCT | 1834 |
| GAGCTATTTGGGACAGGAGT | 1835 |
| GTGGACAACAGTGGAGGGTA | 1836 |
| CATAATGGAGCCCTTTCTCT | 1837 |
| CTCATAATGGAGCCCTTTCT | 1838 |
| GACAACAGAAGCTGCTGGGC | 1839 |
| CCCACAGCAGGACAAGCAAC | 1840 |
| CTGATTCCCTCAGAGAGACA | 1841 |
| CTTTCTGCTATCCATCACTT | 1842 |
| CAACAGAAGCTGCTGGGCTG | 1843 |
| AAGCTTTGTCAGCTAGTTGT | 1844 |
| CAAGCAACTGGAGGTCTGCA | 1845 |
| TCAGGCTAACATTGCTGCTT | 1846 |
| AACCTCTCTGAATACTGCCC | 1847 |
| CCAGAATCCATGTGTCTTCA | 1848 |
| GATTCCCTCAGAGAGACAGA | 1849 |
| AGTCATCAGCCATTCCTTAA | 1850 |
| ACCCATGCTCATAATGGAGC | 1851 |
| CCCTGGAGATACTCAGACAC | 1852 |
| AGCTAGGTGGAGGAAGGATC | 1853 |
| TTCCATCTGTCCTGGAATGA | 1854 |
| TGGGTTGTTGCACATTTTGT | 1855 |
| TGTTGGGTTGTTGCACATTT | 1856 |
| TGATCTGCCTGGACCAGAAG | 1857 |

-continued

| | |
|---|---|
| TGACTGCTATCAGCAGGAGA | 1858 |
| CCACAATGGGCAGAGGATCA | 1859 |
| TCATAATGGAGCCCTTTCTC | 1860 |
| CTAGATCAGCAATGCCCCAA | 1861 |
| CCCAACCAGAAATGGCAGCT | 1862 |
| GGAGTGGGACTGATTGGAGA | 1863 |
| TCCATCTGTCCTGGAATGAG | 1864 |
| AGAGAGGTGACACTTCAGGG | 1865 |
| AGCAACTCTTGTCTAAGGGC | 1866 |
| AGGCTAACATTGCTGCTTGG | 1867 |
| TGTGTCTTCATTCATTCACC | 1868 |
| GTCACCTCTGAACACACTGG | 1869 |
| TTCTCTGAGATACTTCCCAC | 1870 |
| ATCATGCCACCTTGGATTTT | 1871 |
| CTGGATGCTGGACTCTGATT | 1872 |
| GAGCTAGGTGGAGGAAGGAT | 1873 |
| TCATTCCTGGAATCCTTACC | 1874 |
| TTATGCCCCAGTCTGGAAAC | 1875 |
| ATCAGGCTAACATTGCTGCT | 1876 |
| GTAAACTGTGGGTTCTCCTG | 1877 |
| TGTAAACTGTGGGTTCTCCT | 1878 |
| ATTTGGGACAGGAGTCAGTT | 1879 |
| GGAGCTATTTGGGACAGGAG | 1880 |
| AGGAGCTATTTGGGACAGGA | 1881 |
| GAGGAGCTATTTGGGACAGG | 1882 |
| ATCTTCAACTCACTCTACCC | 1883 |
| AAGGGAAGGCCAGGAAGCTT | 1884 |
| CTATGGCAGCAGAACTGTGT | 1885 |
| GGCATCTTCAACTCACTCTA | 1886 |
| CTTCAACTCACTCTACCCAG | 1887 |
| CAAGCTGACTGCTATCAGCA | 1888 |
| CTGGCTGAAGAGTGCCAATC | 1889 |
| AGGGTTCCCCACATGAAATC | 1890 |
| ACACAGGGCAGTGGACAACA | 1891 |
| CACACAGGGCAGTGGACAAC | 1892 |
| TTTATGCCCCAGTCTGGAAA | 1893 |
| TCCCAACCAGAAATGGCAGC | 1894 |
| ATAATGGAGCCCTTTCTCTT | 1895 |
| TTATTTTCCAGAGCCATGTC | 1896 |

-continued

| | |
|---|---|
| GGGTTGTTGCACATTTTGTA | 1897 |
| TTTTCCATCTGTCCTGGAAT | 1898 |
| GGATATTCCTGCTCTGTATG | 1899 |
| TGCTATCAGCAGGAGAAGGG | 1900 |
| GAGGGTTCCCCACATGAAAT | 1901 |
| AGGAAAGGCCACTTCTGAGT | 1902 |
| GGCTGTTCTGATTGGGTAAT | 1903 |
| TGGATGCTGGACTCTGATTC | 1904 |
| GATTCTCTGAGATACTTCCC | 1905 |
| TGAGGGTTCCCCACATGAAA | 1906 |
| CTGTCCTGGAATGAGGATCT | 1907 |
| TGCCCAGAGATGTCAAGAGA | 1908 |
| CACAGGGCAGTGGACAACAG | 1909 |
| ATTCTCTGAGATACTTCCCA | 1910 |
| GAATGTGGTACCTGGTTAGT | 1911 |
| AATCATCCCCTGGAGATACT | 1912 |
| GATCAGGCTAACATTGCTGC | 1913 |
| ACCAAGCAACTGGAGGTCTG | 1914 |
| AATTGCCCACAATGGGCAGA | 1915 |
| CAGTGGACAACAGTGGAGGG | 1916 |
| TAAACTGTGGGTTCTCCTGG | 1917 |
| ATGAGATGCCTCTCTTCATG | 1918 |
| TCAACTTCTGTTGGGTTGTT | 1919 |
| TTTCCATCTGTCCTGGAATG | 1920 |
| ATCTCAACTTCTGTTGGGTT | 1921 |
| ACACCAAGCAACTGGAGGTC | 1922 |
| TAATGGAGCCCTTTCTCTTA | 1923 |
| TCTCAACTTCTGTTGGGTTG | 1924 |
| GGCTGAAGAGTGCCAATCAT | 1925 |
| GCTGACTTTTTCCTGTATGA | 1926 |
| GCTGGAAAGGCTGATCCTC | 1927 |
| TTGGAGGAAAGGCCACTTCT | 1928 |
| TCCATCACTTATAACCCCAC | 1929 |
| TCTGTCCTGGAATGAGGATC | 1930 |
| AACTCTTGTCTAAGGGCAGT | 1931 |
| GAATGAGTGTGGCTGGACTT | 1932 |
| GAGGAAGAGTGTTGCCTTTG | 1933 |
| ATCCATGTGTCTTCATTCAT | 1934 |
| CAGTCACCTCTGAACACACT | 1935 |
| CCACTTCCTCATACATTCTA | 1936 |

-continued

| | |
|---|---|
| CTGCTATCAGCAGGAGAAGG | 1937 |
| GATCTCTGGAGGAAGAGTGT | 1938 |
| GTGATCTCTGGAGGAAGAGT | 1939 |
| TATTTGGGACAGGAGTCAGT | 1940 |
| GTCCTGGAATGAGGATCTGA | 1941 |
| CCAGTAAATCCTGTGTCACT | 1942 |
| GCAGGACAAGCAACTCTTGT | 1943 |
| AAGCTGACTGCTATCAGCAG | 1944 |
| TGATTCCCTCAGAGAGACAG | 1945 |
| CCATCACTTATAACCCCACA | 1946 |
| CAATGGGCAGAGGATCATGC | 1947 |
| CATCTGTCCTGGAATGAGGA | 1948 |
| GAGAGAGGTGACACTTCAGG | 1949 |
| CTTGGTGATCTCTGGAGGAA | 1950 |
| CAGGCTAACATTGCTGCTTG | 1951 |
| GAAATGGCAGCTTCATTCCT | 1952 |
| TGGAGGAAAGGCCACTTCTG | 1953 |
| GGAAAAGGCTGATCCTCACC | 1954 |
| AGCAGGCTTTGGAGGAAAGG | 1955 |
| TGAATGAGTGTGGCTGGACT | 1956 |
| TCATCAGCCATTCCTTAACA | 1957 |
| ATCCATCACTTATAACCCCA | 1958 |
| AAAGAACAGCTTCTCCAGCC | 1959 |
| CAGAGGAGCTATTTGGGACA | 1960 |
| CCTCTGTCTAGGATCTAGAA | 1961 |
| CAATGAGATGCCTCTCTTCA | 1962 |
| GAAGCTTTGTCAGCTAGTTG | 1963 |
| GGTGATCTCTGGAGGAAGAG | 1964 |
| TTGTAAACTGTGGGTTCTCC | 1965 |
| AAGAGCCAGAAATCATCCCC | 1966 |
| TGTCTTCATTCATTCACCTA | 1967 |
| ATGGCAGCAGAACTGTGTTA | 1968 |
| TATGGCAGCAGAACTGTGTT | 1969 |
| AAAAGGCTGATCCTCACCTC | 1970 |
| GTTCTGTCAGATCACATGTA | 1971 |
| AATGAGTGTGGCTGGACTTT | 1972 |
| AGGATCAGGCTAACATTGCT | 1973 |
| TCTGATTGGGTAATGCAGGG | 1974 |
| CAGAAATCATCCCCTGGAGA | 1975 |

-continued

| | |
|---|---|
| GACTGCTATCAGCAGGAGAA | 1976 |
| GAGTGGGACTGATTGGAGAC | 1977 |
| GAAAAGGCTGATCCTCACCT | 1978 |
| CTTCATTCCTGGAATCCTTA | 1979 |
| ACAGAGGGCAAGAGGAGCAA | 1980 |
| CTTTGGAGGAAAGGCCACTT | 1981 |
| TCAAGAGAGACCAAGGCACC | 1982 |
| TGGTGATCTCTGGAGGAAGA | 1983 |
| TTGACCTTTAATGTCCCTGA | 1984 |
| GTGTTAAAGGGAAGGCCAGG | 1985 |
| ATCTCTGGAGGAAGAGTGTT | 1986 |
| ATGCCACCTTGGATTTTCAA | 1987 |
| TTTCTGCTATCCATCACTTA | 1988 |
| AGTGGGACTGATTGGAGACA | 1989 |
| AATGTGGTACCTGGTTAGTG | 1990 |
| TCCATCAAGCTTTCATCAGA | 1991 |
| TGACCTTTAATGTCCCTGAG | 1992 |
| GTTCTCCTGGTATATCTATA | 1993 |
| GAGGTAGTCAAGAGAGACCA | 1994 |
| ACAATGAGATGCCTCTCTTC | 1995 |
| CTCCCAACCAGAAATGGCAG | 1996 |
| GCATCTTCAACTCACTCTAC | 1997 |
| CTGAGAGAGGTGACACTTCA | 1998 |
| CAAGAGAGACCAAGGCACCA | 1999 |
| GGATCAGGCTAACATTGCTG | 2000 |
| AGTCACCTCTGAACACACTG | 2001 |
| ATGGAGCCCTTTCTCTTAAA | 2002 |
| AATGGAGCCCTTTCTCTTAA | 2003 |
| TGCTGGAAAAGGCTGATCCT | 2004 |
| CAACTTCTGTTGGGTTGTTG | 2005 |
| TTTGGAGGAAAGGCCACTTC | 2006 |
| ATCTGTCCTGGAATGAGGAT | 2007 |
| TTCTGCTATCCATCACTTAT | 2008 |
| GGTCAGCTTTTTGTTGCAAA | 2009 |
| AGAGGAGCTATTTGGGACAG | 2010 |
| GCCCAGAGATGTCAAGAGAA | 2011 |
| TTTTGACCTTTAATGTCCCT | 2012 |
| CTTTTGACCTTTAATGTCCC | 2013 |
| TGTCCTGGAATGAGGATCTG | 2014 |
| GTCAAGAGAGACCAAGGCAC | 2015 |

-continued

| | |
|---|---|
| TCAGCAGGAGAAGGGAATGC | 2016 |
| GCAATGCCCCAAATTGTTGA | 2017 |
| GTTCCCCACATGAAATCCAA | 2018 |
| GAGCAGGCTTTGGAGGAAAG | 2019 |
| CATCTTCAACTCACTCTACC | 2020 |
| TGGACAACAGTGGAGGGTAT | 2021 |
| AAATGGCAGCTTCATTCCTG | 2022 |
| GAGGGCAAGAGGAGCAAAGT | 2023 |
| CAGCAGGACAAGCAACTCTT | 2024 |
| TTGGGTTGTTGCACATTTTG | 2025 |
| ACTATGGCAGCAGAACTGTG | 2026 |
| AATGAGATGCCTCTCTTCAT | 2027 |
| GAAATTGCCCACAATGGGCA | 2028 |
| AAGAGAGACCAAGGCACCAC | 2029 |
| CAGCAGGAGAAGGGAATGCA | 2030 |
| CCAACCAGAAATGGCAGCTT | 2031 |
| TCTGTCAGATCACATGTACT | 2032 |
| TTTGACCTTTAATGTCCCTG | 2033 |
| CAACTCTTGTCTAAGGGCAG | 2034 |
| GATCAGCAATGCCCCAAATT | 2035 |
| CTGTGTTAAAGGGAAGGCCA | 2036 |
| CCTGAACCCATGCTCATAAT | 2037 |
| TTTCCATCAAGCTTTCATCA | 2038 |
| GCTGAAGAGTGCCAATCATT | 2039 |
| GGGCAAGAGGAGCAAAGTGA | 2040 |
| CCATCAAGCTTTCATCAGAC | 2041 |
| TATCCATCACTTATAACCCC | 2042 |
| AGATCAGCAATGCCCCAAAT | 2043 |
| AGGACAAGCAACTCTTGTCT | 2044 |
| GAATCCATGTGTCTTCATTC | 2045 |
| TTCCATCAAGCTTTCATCAG | 2046 |
| ATCACTTATAACCCCACAGG | 2047 |
| GATGGAACTATGGCAGCAGA | 2048 |
| GGACAACAGTGGAGGGTATA | 2049 |
| CTGTTCTGATTGGGTAATGC | 2050 |
| GCTGTTCTGATTGGGTAATG | 2051 |
| CCCAGTCTGGAAACATTCAT | 2052 |
| AATCCATGTGTCTTCATTCA | 2053 |
| ATTCCCTCAGAGAGACAGAA | 2054 |

-continued

| | |
|---|---|
| AGACAACAGAAGCTGCTGGG | 2055 |
| TTCATTCCTGGAATCCTTAC | 2056 |
| AATCTCAACTTCTGTTGGGT | 2057 |
| ATGAATGAGTGTGGCTGGAC | 2058 |
| GCCACCTTGGATTTTCAAAC | 2059 |
| CACAATGGGCAGAGGATCAT | 2060 |
| CAGAATCCATGTGTCTTCAT | 2061 |
| CCCTCAGAGAGACAGAAGAT | 2062 |
| GCTGATTCTCTGAGATACTT | 2063 |
| GAGCCCTTTCTCTTAAAAGT | 2064 |
| AGCAATGCCCCAAATTGTTG | 2065 |
| CTAACATTGCTGCTTGGCAA | 2066 |
| GGAGGAAGGATCAGGCTAAC | 2067 |
| ACTGTGTTAAAGGGAAGGCC | 2068 |
| GTTCTGATTGGGTAATGCAG | 2069 |
| CAGTCAGCAGAGCACAATTA | 2070 |
| AGCTGATTCTCTGAGATACT | 2071 |
| CTGGAAAAGGCTGATCCTCA | 2072 |
| TGTTAAAGGGAAGGCCAGGA | 2073 |
| AAATTGCCCACAATGGGCAG | 2074 |
| GAAATCATCCCCTGGAGATA | 2075 |
| CAGGACAAGCAACTCTTGTC | 2076 |
| AGCAGGAGAAGGGAATGCAG | 2077 |
| GGACAAGCAACTCTTGTCTA | 2078 |
| CTTAGCTGATTCTCTGAGAT | 2079 |
| GTCTTCATTCATTCACCTAA | 2080 |
| TGTTCTGATTGGGTAATGCA | 2081 |
| GGAACTATGGCAGCAGAACT | 2082 |
| TGAATGTGGTACCTGGTTAG | 2083 |
| TTTCTGTGAAATTGCCCACA | 2084 |
| TGAAATTGCCCACAATGGGC | 2085 |
| GAATCATAACCCACACAGGC | 2086 |
| AGCAGGACAAGCAACTCTTG | 2087 |
| GCTGGACTTTTGACCTTTAA | 2088 |
| TGCCACCTTGGATTTTCAAA | 2089 |
| TGAGAGAGGTGACACTTCAG | 2090 |
| GGAGCCCTTTCTCTTAAAAG | 2091 |
| AGGGCAAGAGGAGCAAAGTG | 2092 |
| CTGTCAGATCACATGTACTT | 2093 |
| TTCTGATTGGGTAATGCAGG | 2094 |

-continued

ATGAATGTGGTACCTGGTTA                                              2095

AACACCAAGCAACTGGAGGT                                              2096

ACTTCCTCATACATTCTACA                                              2097

CACTTCCTCATACATTCTAC                                              2098

ATGCTGGAAAAGGCTGATCC                                              2099

AGATGGAACTATGGCAGCAG                                              2100

TGGAGGAAGGATCAGGCTAA                                              2101

TCCTGGAATGAGGATCTGAT                                              2102

AAACAAACCTTCTGGTGCCT                                              2103

ATTTCCATCAAGCTTTCATC                                              2104

AGTAAATCCTGTGTCACTTC                                              2105

AATCCAAACTCTCTCTCTGG                                              2106

GCCCTTTCTCTTAAAAGTTT                                              2107

AGAATCCATGTGTCTTCATT                                              2108

CATCACTTATAACCCCACAG                                              2109

TGGAGCCCTTTCTCTTAAAA                                              2110

GTGGGACTGATTGGAGACAA                                              2111

TGATTCTCTGAGATACTTCC                                              2112

TGATCTCTGGAGGAAGAGTG                                              2113

GCTATCCATCACTTATAACC                                              2114

CATTTCTGTGAAATTGCCCA                                              2115

AAATCATCCCCTGGAGATAC                                              2116

CAGTAAATCCTGTGTCACTT                                              2117

AGCCCTTTCTCTTAAAAGTT                                              2118

CAGAGGGCAAGAGGAGCAAA                                              2119

TGTGTTAAAGGGAAGGCCAG                                              2120

GAACCCATGCTCATAATGGA                                              2121

TTCTGTCAGATCACATGTAC                                              2122

TAGTCAAGAGAGACCAAGGC                                              2123

ACAATGGGCAGAGGATCATG                                              2124

ACAGGATGCTGGAAAAGGCT                                              2125

CTATCCATCACTTATAACCC                                              2126

AACTATGGCAGCAGAACTGT                                              2127

GAAACAAACCTTCTGGTGCC                                              2128

CATCAGCCATTCCTTAACAA                                              2129

GTGAAATTGCCCACAATGGG                                              2130

AGTCAGCAGAGCACAATTAT                                              2131

GAGGAAGGATCAGGCTAACA                                              2132

TAGATGGAACTATGGCAGCA                                              2133

-continued

| | |
|---|---|
| CAACCAGAAATGGCAGCTTC | 2134 |
| ATTTCTGTGAAATTGCCCAC | 2135 |
| CTGACTTTTTCCTGTATGAT | 2136 |
| GGTTGTTGCACATTTTGTAA | 2137 |
| AAACCTCTCTGAATACTGCC | 2138 |
| GACAACAGTGGAGGGTATAC | 2139 |
| TCAGCAGAGCACAATTATGT | 2140 |
| GTCAGCAGAGCACAATTATG | 2141 |
| TTTGTAAACTGTGGGTTCTC | 2142 |
| CTATCAGCAGGAGAAGGGAA | 2143 |
| GTCAGATCACATGTACTTTT | 2144 |
| CACAGGATGCTGGAAAAGGC | 2145 |
| CCAGTCTGGAAACATTCATC | 2146 |
| CTCTGTCTAGGATCTAGAAT | 2147 |
| GTGAACACCAAGCAACTGGA | 2148 |
| ACTTTTGACCTTTAATGTCC | 2149 |
| AACCCATGCTCATAATGGAG | 2150 |
| GTAGTCAAGAGAGACCAAGG | 2151 |
| GGTAGTCAAGAGAGACCAAG | 2152 |
| AGGTAGTCAAGAGAGACCAA | 2153 |
| GAACACCAAGCAACTGGAGG | 2154 |
| CCTCAGAGAGACAGAAGATC | 2155 |
| TGGAACTATGGCAGCAGAAC | 2156 |
| TGAACCCATGCTCATAATGG | 2157 |
| AAGGATCAGGCTAACATTGC | 2158 |
| GCAGGAAACCTCTCTGAATA | 2159 |
| ATCAGCCATTCCTTAACAAT | 2160 |
| GATGATGACAGAGACTCTGG | 2161 |
| GGAAGGATCAGGCTAACATT | 2162 |
| TCAGCCATTCCTTAACAATG | 2163 |
| ATGCCCCAAATTGTTGAATC | 2164 |
| TCTGTCTAGGATCTAGAATC | 2165 |
| CAGCCATTCCTTAACAATGA | 2166 |
| TTCTGTGAAATTGCCCACAA | 2167 |
| ATTCTACAATGAGATGCCTC | 2168 |
| ATAGATGGAACTATGGCAGC | 2169 |
| AGGAAGGATCAGGCTAACAT | 2170 |
| GAGGAGCAAAGTGAACACCA | 2171 |
| AAGCAACTCTTGTCTAAGGG | 2172 |
| TAGCTGATTCTCTGAGATAC | 2173 |

-continued

| | |
|---|---|
| CTGTCTAGGATCTAGAATCA | 2174 |
| TTTTGTAAACTGTGGGTTCT | 2175 |
| CATTCTACAATGAGATGCCT | 2176 |
| CTGATTCTCTGAGATACTTC | 2177 |
| GGAAACTTAGCTGATTCTCT | 2178 |
| ATGGAACTATGGCAGCAGAA | 2179 |
| CCCCACATGAAATCCAAACT | 2180 |
| GAACTATGGCAGCAGAACTG | 2181 |
| CTGAACCCATGCTCATAATG | 2182 |
| TCTGTGAAATTGCCCACAAT | 2183 |
| TTAGCTGATTCTCTGAGATA | 2184 |
| GATGCTGGAAAAGGCTGATC | 2185 |
| AGTGAACACCAAGCAACTGG | 2186 |
| ATCAGCAGGAGAAGGGAATG | 2187 |
| AACTTAGCTGATTCTCTGAG | 2188 |
| TCCCCACATGAAATCCAAAC | 2189 |
| GCCACTCTGAACTTTATGAA | 2190 |
| GGACTTTTGACCTTTAATGT | 2191 |
| AAAGAGCCAGAAATCATCCC | 2192 |
| CCTTTCTCTTAAAAGTTTCC | 2193 |
| CCCTTTCTCTTAAAAGTTTC | 2194 |
| TTCCCCACATGAAATCCAAA | 2195 |
| TAATCTCAACTTCTGTTGGG | 2196 |
| ATTGGAGACAAAGAGCCAGA | 2197 |
| TATCAGCAGGAGAAGGGAAT | 2198 |
| GTCAGCTTTTTGTTGCAAAA | 2199 |
| ACAATGAATGTGGTACCTGG | 2200 |
| AGAGGAGCAAAGTGAACACC | 2201 |
| TCACATTTGGATGGACAAGT | 2202 |
| TGATCACATTTGGATGGACA | 2203 |
| GGATCTGATGATGACAGAGA | 2204 |
| GAGGATCTGATGATGACAGA | 2205 |
| CAGTCTGGAAACATTCATCT | 2206 |
| GGATCTAGAATCATAACCCA | 2207 |
| GAAATCCAAACTCTCTCTCT | 2208 |
| GAAACCTCTCTGAATACTGC | 2209 |
| CTGAAGAGTGCCAATCATTA | 2210 |
| CAAGCAACTCTTGTCTAAGG | 2211 |
| AAAAGCCATTTCCATCAAGC | 2212 |

-continued

| GACTTTTTCCTGTATGATAT | 2213 |
| TTCTCCTGGTATATCTATAA | 2214 |
| AGCTTTTTGTTGCAAAATCC | 2215 |
| GAAGAGTGCCAATCATTACA | 2216 |
| TGACTTTTTCCTGTATGATA | 2217 |
| GCTTTCATCAGACAATATCA | 2218 |
| ACATTCTACAATGAGATGCC | 2219 |
| TTTGGATGGACAAGTTAGGA | 2220 |
| TTCTCTTAAAAGTTTCCTCT | 2221 |
| GAGCAAAGTGAACACCAAGC | 2222 |
| AGCAAAGTGAACACCAAGCA | 2223 |
| CAATGCCCCAAATTGTTGAA | 2224 |
| TGGAGAAGTAAGTGGCCAAA | 2225 |
| ATTACAAATCAGCTTCAGCA | 2226 |
| CATTACAAATCAGCTTCAGC | 2227 |
| GTCTGGAAACATTCATCTTT | 2228 |
| GACTTTTGACCTTTAATGTC | 2229 |
| AGGAAACTTAGCTGATTCTC | 2230 |
| ACATTTTGTAAACTGTGGGT | 2231 |
| CACATTTGGATGGACAAGTT | 2232 |
| ATTTTGTAAACTGTGGGTTC | 2233 |
| AGGATCTAGAATCATAACCC | 2234 |
| CCCAGAGATGTCAAGAGAAA | 2235 |
| AGGATCTGATGATGACAGAG | 2236 |
| CATTTTGTAAACTGTGGGTT | 2237 |
| GCACATTTTGTAAACTGTGG | 2238 |
| GACAAGCAACTCTTGTCTAA | 2239 |
| ACTTTTTCCTGTATGATATT | 2240 |
| GCCAATCATTACAAATCAGC | 2241 |
| GAAGGATCAGGCTAACATTG | 2242 |
| TGAGGATCTGATGATGACAG | 2243 |
| TGATGATGACAGAGACTCTG | 2244 |
| AGGAAACCTCTCTGAATACT | 2245 |
| TTCCTCATACATTCTACAAT | 2246 |
| AGCTTTCATCAGACAATATC | 2247 |
| ATGAGGATCTGATGATGACA | 2248 |
| TGAAGAGTGCCAATCATTAC | 2249 |
| CTTTCTCTTAAAAGTTTCCT | 2250 |
| GGAAACCTCTCTGAATACTG | 2251 |
| TCTTCATTCATTCACCTAAA | 2252 |

-continued

AAACTTAGCTGATTCTCTGA                                          2253

GAAACTTAGCTGATTCTCTG                                          2254

GATCACATTTGGATGGACAA                                          2255

AATGCCCCAAATTGTTGAAT                                          2256

ATTTGGATGGACAAGTTAGG                                          2257

TCCTCATACATTCTACAATG                                          2258

AGCCATTCCTTAACAATGAA                                          2259

CCTCATACATTCTACAATGA                                          2260

AACTGTGTTAAAGGGAAGGC                                          2261

GATCTAGAATCATAACCCAC                                          2262

AGGAGCAAAGTGAACACCAA                                          2263

GATCTGATGATGACAGAGAC                                          2264

GCCATTCCTTAACAATGAAT                                          2265

CAAAGAGCCAGAAATCATCC                                          2266

CAGGAAACCTCTCTGAATAC                                          2267

TTAATCTCAACTTCTGTTGG                                          2268

TTTCTCTTAAAAGTTTCCTC                                          2269

ACAAGCAACTCTTGTCTAAG                                          2270

ATAAAGAACAGCTTCTCCAG                                          2271

GGGAAAGGATGAATGAGTGT                                          2272

CTATAAAGAACAGCTTCTCC                                          2273

ACTGAAACAAACCTTCTGGT                                          2274

CTTTTTCCTGTATGATATTA                                          2275

CTTCATTCATTCACCTAAAC                                          2276

GGAGAAGTAAGTGGCCAAAA                                          2277

GTTGTTGCACATTTTGTAAA                                          2278

GTGCCAATCATTACAAATCA                                          2279

GCAAAGTGAACACCAAGCAA                                          2280

CACATTTTGTAAACTGTGGG                                          2281

ACTGATTGGAGACAAAGAGC                                          2282

TGGACTTTTGACCTTTAATG                                          2283

TCTCCTGGTATATCTATAAA                                          2284

TTACAAATCAGCTTCAGCAA                                          2285

GTTAGGAAACTTAGCTGATT                                          2286

ACATTTGGATGGACAAGTTA                                          2287

TTGGATGGACAAGTTAGGAA                                          2288

TAGGAAACTTAGCTGATTCT                                          2289

CAGCTTTTTGTTGCAAAATC                                          2290

TCAGCTTTTTGTTGCAAAAT                                          2291

-continued

| | |
|---|---|
| AGTTAGGAAACTTAGCTGAT | 2292 |
| CCACATGAAATCCAAACTCT | 2293 |
| CTGAAACAAACCTTCTGGTG | 2294 |
| TATAAAGAACAGCTTCTCCA | 2295 |
| TCCTTAACAATGAATGTGGT | 2296 |
| CATTTGGATGGACAAGTTAG | 2297 |
| GAGATGATTCCAAAGAGGAT | 2298 |
| CCAATCATTACAAATCAGCT | 2299 |
| TTATAGATGGAACTATGGCA | 2300 |
| TTGCACATTTTGTAAACTGT | 2301 |
| GTTGCACATTTTGTAAACTG | 2302 |
| TGTTGCACATTTTGTAAACT | 2303 |
| AGAGTGCCAATCATTACAAA | 2304 |
| AAGAGTGCCAATCATTACAA | 2305 |
| AAGTGAACACCAAGCAACTG | 2306 |
| CAAGCTTTCATCAGACAATA | 2307 |
| TCATTACAAATCAGCTTCAG | 2308 |
| TATAGATGGAACTATGGCAG | 2309 |
| GAGTGCCAATCATTACAAAT | 2310 |
| AGTGCCAATCATTACAAATC | 2311 |
| CATCAGACAATATCACATGT | 2312 |
| ATCATTACAAATCAGCTTCA | 2313 |
| TGCACATTTTGTAAACTGTG | 2314 |
| ACATGTACTTTTAATGTGGA | 2315 |
| CACATGTACTTTTAATGTGG | 2316 |
| GAATGAGGATCTGATGATGA | 2317 |
| CTTTCATCAGACAATATCAC | 2318 |
| AACAATGAATGTGGTACCTG | 2319 |
| ACAAGTTAGGAAACTTAGCT | 2320 |
| CCAGAGATGTCAAGAGAAAC | 2321 |
| TTTATAGATGGAACTATGGC | 2322 |
| CAGACAATATCACATGTACT | 2323 |
| ATTTAATCTCAACTTCTGTT | 2324 |
| TTTAATCTCAACTTCTGTTG | 2325 |
| GGATGGACAAGTTAGGAAAC | 2326 |
| GAGAAGTAAGTGGCCAAAAC | 2327 |
| TTAGGAAACTTAGCTGATTC | 2328 |
| AGAAGTAAGTGGCCAAAACA | 2329 |
| TCCTGGTATATCTATAAAGA | 2330 |
| GAACTGTGTTAAAGGGAAGG | 2331 |

-continued

| | |
|---|---|
| TCCAAAGAGGATAAACCAGA | 2332 |
| TTTCATCAGACAATATCACA | 2333 |
| TAACAATGAATGTGGTACCT | 2334 |
| CAAGAGGAGCAAAGTGAACA | 2335 |
| AATGAGGATCTGATGATGAC | 2336 |
| TACATTCTACAATGAGATGC | 2337 |
| AAGCTTTCATCAGACAATAT | 2338 |
| AAGTTAGGAAACTTAGCTGA | 2339 |
| CAAGTTAGGAAACTTAGCTG | 2340 |
| CCTTAACAATGAATGTGGTA | 2341 |
| GACAAGTTAGGAAACTTAGC | 2342 |
| TGGATGGACAAGTTAGGAAA | 2343 |
| GGAAAGGATGAATGAGTGTG | 2344 |
| TTCATCAGACAATATCACAT | 2345 |
| AGATGATTCCAAAGAGGATA | 2346 |
| TTGTTGCACATTTTGTAAAC | 2347 |
| TCTATAAAGAACAGCTTCTC | 2348 |
| TCAGACAATATCACATGTAC | 2349 |
| ATCACATGTACTTTTAATGT | 2350 |
| AAAGTGAACACCAAGCAACT | 2351 |
| ACAAAGAGCCAGAAATCATC | 2352 |
| TGCCAATCATTACAAATCAG | 2353 |
| TCATCAGACAATATCACATG | 2354 |
| TAGGATCTAGAATCATAACC | 2355 |
| AAGAGGAGCAAAGTGAACAC | 2356 |
| TTCCAAAGAGGATAAACCAG | 2357 |
| ATCAGACAATATCACATGTA | 2358 |
| CTCATACATTCTACAATGAG | 2359 |
| TTCCTTAACAATGAATGTGG | 2360 |
| ATGTCAAGAGAAACAGGAGA | 2361 |
| GATGTCAAGAGAAACAGGAG | 2362 |
| AGATGTCAAGAGAAACAGGA | 2363 |
| GAGATGTCAAGAGAAACAGG | 2364 |
| ATTCCAAAGAGGATAAACCA | 2365 |
| GATTCCAAAGAGGATAAACC | 2366 |
| CAAAGTGAACACCAAGCAAC | 2367 |
| CCATTCCTTAACAATGAATG | 2368 |
| ATGGACAAGTTAGGAAACTT | 2369 |
| TTAACAATGAATGTGGTACC | 2370 |

-continued

| | |
|---|---|
| TCATACATTCTACAATGAGA | 2371 |
| ATCTATAAAGAACAGCTTCT | 2372 |
| GAAGTAAGTGGCCAAAACAA | 2373 |
| GCCAAAACAAACACATTTCT | 2374 |
| GGACAAGTTAGGAAACTTAG | 2375 |
| TGGACAAGTTAGGAAACTTA | 2376 |
| AATTTAATCTCAACTTCTGT | 2377 |
| CATTCCTTAACAATGAATGT | 2378 |
| GATCACATGTACTTTTAATG | 2379 |
| CAATCATTACAAATCAGCTT | 2380 |
| CAGAGATGTCAAGAGAAACA | 2381 |
| AATCATTACAAATCAGCTTC | 2382 |
| GATGATTCCAAAGAGGATAA | 2383 |
| CCAAAGAGGATAAACCAGAA | 2384 |
| CTAGGATCTAGAATCATAAC | 2385 |
| CATACATTCTACAATGAGAT | 2386 |
| CCTGGTATATCTATAAAGAA | 2387 |
| AGAGATGTCAAGAGAAACAG | 2388 |
| ATTCCTTAACAATGAATGTG | 2389 |
| TTTTATAGATGGAACTATGG | 2390 |
| TCCTGTATGATATTAAGAAT | 2391 |
| CTTAACAATGAATGTGGTAC | 2392 |
| TCAGCAAACTGAAACAAACC | 2393 |
| AGCAAACTGAAACAAACCTT | 2394 |
| TATCTATAAAGAACAGCTTC | 2395 |
| ATACATTCTACAATGAGATG | 2396 |
| AAGTAAGTGGCCAAAACAAA | 2397 |
| CATTTTATAGATGGAACTAT | 2398 |
| CAAACACATTTCTGTGAAAT | 2399 |
| GTATATCTATAAAGAACAGC | 2400 |
| CTTCAGCAAACTGAAACAAA | 2401 |
| ATTTTATAGATGGAACTATG | 2402 |
| TATATCTATAAAGAACAGCT | 2403 |
| CTGGTATATCTATAAAGAAC | 2404 |
| GGTATATCTATAAAGAACAG | 2405 |
| TGGTATATCTATAAAGAACA | 2406 |
| TTCAGCAAACTGAAACAAAC | 2407 |
| CTGTATGATATTAAGAATTA | 2408 |
| GATATTAAGAATTATATTTC | 2409 |
| GCACAGCCTGCATGTCCTCA | 2410 |

-continued

```
GCCCAGGCCCTTGCTCAGAA                                          2411

AGGTTGTCTCAGCCCAGGGA                                          2412
```

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA)

or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to, such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

SEQUENCE LISTING

The patent contains a lengthy sequence listing. A copy of the sequence listing is available in electronic form from the USPTO web site (https://seqdata.uspto.gov/docdetail?docId=US12595481B2). An electronic copy of the sequence listing will also be available from the USPTO upon request and payment of the fee set forth in 37 CFR 1.19(b)(3).

The invention claimed is:

1. An antisense oligonucleotide comprising a sequence having at least 95% identity to a sequence selected from a group consisting of SEQ ID NO: 4-10, 12-14, 18-21, 23-26, and 38.

2. The antisense oligonucleotide of claim 1, comprising a sequence selected from the group consisting of SEQ ID NO: 4-10, 12-14, 18-21, 23-26, and 38.

3. The antisense oligonucleotide of claim 2, wherein the antisense oligonucleotide comprises one or more modifications.

4. The antisense oligonucleotide of claim 3, wherein the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof.

5. An antisense oligonucleotide comprising a sequence having at least 95% identity to a sequence selected from a group consisting of SEQ ID NO: 3-21, 23-26, 38 and 39, wherein the antisense oligonucleotide comprises one or more modifications, the one or more modifications comprise methylphosphonothioate internucleotide linkages, phosphorothioate internucleotide linkages, methylphosphonate internucleotide linkages, phosphoramidate internucleotide linkages, a 3' end cap, a 3' hair-pin loop structure, or a combination thereof and the antisense oligonucleotide comprises internucleotide linkages of the pattern $R_S R_O R_S R_O R_S$ $D_S D_S D_S D_S D_S D_S D_S D_S D_S D_S R_O R_S R_O R_S$, wherein $R_S$ is an RNA (2'-MOE) phosphorothioate bond, $R_O$ is an RNA (2'-MOE) phosphodiester bond and $D_S$ is a DNA phosphorothioate bond.

6. An antisense oligonucleotide comprising a sequence selected from the group consisting of SEQ ID NO: 2410-2412, wherein the antisense oligonucleotide comprises internucleotide linkages of the pattern $R_S R_O R_S R_O R_S$ $D_S D_S D_S D_S D_S D_S D_S D_S D_S D_S R_O R_S R_O R_S$, wherein $R_S$ is an RNA (2'-MOE) phosphorothioate bond, $R_O$ is an RNA (2'-MOE) phosphodiester bond and $D_S$ is a DNA phosphorothioate bond.

7. A pharmaceutical composition comprising the antisense oligonucleotide of claim 1.

8. A pharmaceutical composition comprising the antisense oligonucleotide of claim 5.

9. A pharmaceutical composition comprising the antisense oligonucleotide of claim 6.

10. A method of treating or preventing axonal degeneration in a subject, comprising administering to the subject the antisense oligonucleotide of claim 1.

11. A method of treating or preventing axonal degeneration in a subject, comprising administering to the subject the antisense oligonucleotide of claim 5.

12. A method of treating or preventing axonal degeneration in a subject, comprising administering to the subject the antisense oligonucleotide of claim 6.

13. The method of claim 10, wherein administering the antisense oligonucleotide decreases levels of SARM1 mRNA in the subject.

14. The method of claim 11, wherein administering the antisense oligonucleotide decreases levels of SARM1 mRNA in the subject.

15. The method of claim 12, wherein administering the antisense oligonucleotide decreases levels of SARM1 mRNA in the subject.

16. The method of claim 10, wherein administering the antisense oligonucleotide decreases levels of SARM1 protein in the subject.

17. The method of claim 11, wherein administering the antisense oligonucleotide decreases levels of SARM1 protein in the subject.

18. The method of claim 12, wherein administering the antisense oligonucleotide decreases levels of SARM1 protein in the subject.

* * * * *